(12) United States Patent
Liu et al.

(10) Patent No.: US 11,021,462 B2
(45) Date of Patent: Jun. 1, 2021

(54) SULFONE PYRIDINE ALKYL AMIDE-SUBSTITUTED HETEROARYL COMPOUNDS

(71) Applicant: BRISTOL-MYERS SQUIBB COMPANY, Princeton, NJ (US)

(72) Inventors: Chunjian Liu, Pennington, NJ (US); Michael G. Yang, Narberth, PA (US); Zili Xiao, East Windsor, NJ (US); Ling Chen, Doylestown, PA (US); Ryan M. Moslin, Princeton, NJ (US); John S. Tokarski, Princeton, NJ (US); David S. Weinstein, San Diego, CA (US); Stephen T. Wrobleski, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/195,951

(22) Filed: Nov. 20, 2018

(65) Prior Publication Data
US 2019/0152948 A1    May 23, 2019

Related U.S. Application Data

(60) Provisional application No. 62/589,165, filed on Nov. 21, 2017.

(51) Int. Cl.
| | | |
|---|---|---|
| A61K 31/395 | (2006.01) | |
| C07D 401/14 | (2006.01) | |
| C07D 401/12 | (2006.01) | |
| C07D 413/14 | (2006.01) | |
| C07D 471/04 | (2006.01) | |
| C07D 405/14 | (2006.01) | |
| C07F 9/6558 | (2006.01) | |
| C07D 417/14 | (2006.01) | |
| A61P 37/00 | (2006.01) | |
| A61P 29/00 | (2006.01) | |
| A61K 31/501 | (2006.01) | |
| C07D 487/04 | (2006.01) | |

(52) U.S. Cl.
CPC .......... *C07D 401/14* (2013.01); *A61K 31/501* (2013.01); *A61P 29/00* (2018.01); *A61P 37/00* (2018.01); *C07D 401/12* (2013.01); *C07D 405/14* (2013.01); *C07D 413/14* (2013.01); *C07D 417/14* (2013.01); *C07D 471/04* (2013.01); *C07D 487/04* (2013.01); *C07F 9/65583* (2013.01)

(58) Field of Classification Search
CPC .................................................. A61K 31/395
See application file for complete search history.

(56) References Cited

U.S. PATENT DOCUMENTS

| | | |
|---|---|---|
| 9,505,748 B2 | 11/2016 | Moslin et al. |
| 9,663,467 B2 | 5/2017 | Moslin et al. |
| 9,987,266 B2 | 6/2018 | Moslin et al. |
| 10,000,480 B2 | 6/2018 | Moslin et al. |
| 10,294,256 B2 | 5/2019 | Yang et al. |
| 2013/0178478 A1* | 7/2013 | Roche ................. C07D 403/12 514/252.04 |

FOREIGN PATENT DOCUMENTS

| | | |
|---|---|---|
| WO | WO2014/074661 A1 | 5/2014 |
| WO | WO2015/069310 A1 | 5/2015 |
| WO | WO2018/111787 A1 | 6/2018 |

OTHER PUBLICATIONS

U.S. Appl. No. 14/441,183, filed May 7, 2015, Granted U.S. Pat. No. 9,505,748.
U.S. Appl. No. 15/289,437, filed Oct. 10, 2016, Granted U.S. Pat. No. 10,000,480.
PCT/US2013/068846, Filing Date: Nov. 7, 2013, Published WO 2014/074661.
U.S. Appl. No. 15/034,915, filed May 6, 2016, Granted U.S. Pat. No. 9,663,467.
U.S. Appl. No. 15/480,787, filed Apr. 6, 2017, Granted U.S. Pat. No. 9,987,266.
PCT/US2014/011769, Filing Date: Jan. 16, 2014, Published WO 2015/069310.
U.S. Appl. No. 15/838,434, filed Dec. 12, 2017, Granted U.S. Pat. No. 10,294,256.
PCT/US2017/065665, Filing Date: Dec. 12, 2017, Published WO 2018/111787.
Bave, Ullvi, et al., "Activation of the Type I Interferon System in Primary Sjögren's Syndrome a Possible Etiopathogenic Mechanism", Arthritis and Rheumatism, vol. 52, No. 4, Apr. 2005, pp. 1185-1195.
Bengtsson, AA., et al., "Activation of type I interferon system in systemic lupus erythematosus correlates with disease activity but not with antiretroviral antibodies", Lupus, 2000, vol. 9, pp. 664-671.

(Continued)

*Primary Examiner* — John S Kenyon
(74) *Attorney, Agent, or Firm* — Elliott Korsen

(57) ABSTRACT

Compounds having the following formula I:

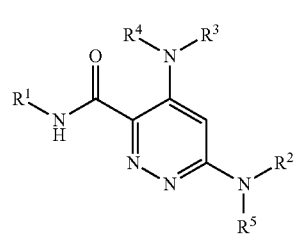

or a stereoisomer or pharmaceutically-acceptable salt thereof, where $R^1$, $R^2$, $R^3$, $R^4$, and $R^5$ are as defined herein, are useful in the modulation of IL-12, IL-23 and/or IFNα, by acting on Tyk-2 to cause signal transduction inhibition.

28 Claims, No Drawings

(56) References Cited

OTHER PUBLICATIONS

Bennett, Lynda, et al., "Interferon and Granulopoiesis Signatures in Systemic Lupus Erythematosus Blood", The Journal of Experimental Medicine, Mar. 17, 2003, vol. 197, No. 6, pp. 711-723.
Bundgaard, H., "Design of Prodrugs", Elsevier, 1985, and Widder, K.,et al., "Methods in Enzymology. vol. 112, Drug and Enzyme Targeting", Part A, Academic Press. 1985. vol. 112, pp. 309-396.
Bundgaard, Hans, "Design and Application of Prodrugs", Korsgaard-Larsen, P., et al., A Textbook of Drug Design and Development, Harwood Academic Publishers, 1991, pp. 113-191.
Bundgaard, Hans, "Means to Enhance Penetration, Prodrugs as a rieans to improve the delivery of peptide drugs", Advanced Drug Delivery Reviews, 1992, vol. 8, pp. 1-38.
Cho, Judy H., et al., "Recent Insights Into the Genetics of Inflammatory Bowel Disease", Gastroenterology, 2011, vol. 140, pp. 1704-1712.
Couturier, Nicolas, et al., "Tyrosine kinase 2 variant influences T lymphocyte polarization and multiple sclerosis susceptibility", Brain 2011, vol. 134, pp. 693-703.
Cua, Daniel J., et al., "Interleukin-23 rather than interleukin-12 is the ciritical cytokine for autoimmune inflammation of the brain", Nature, Feb. 13, 2003, vol. 421, pp. 744-748.
Deng, Yun, et al., "Genetic susceptibility to systemic lupus erythematosus in the genomic era", Nat. Rev. Rheumatol., 2010, vol. 6, pp. 683-692.
Ellinghaus, David, et al., "Combined Analysis of Genome-wide Association Studies for Crohn Disease and Psoriasis Identifies Seven Shared Susceptibility Loci", The American Journal of Human Genetics, Apr. 6, 2012, vol. 90, pp. 636-647.
Eyre, Steve, et al., "High density genetic mapping identifies new susceptibility loci for rheumatoid arthritis", Nat Genet. Dec. 2012 ; vol. 44, No. 12, pp. 1336-1340.
Gottlieb, Alice, et al., "Ustekinumab, a human interleukin 12/23 monoclonal antibody, for psoriatic arthritis: randomised, double-blind, placebo-controlled, crossover trial", Lancet, 2009, vol. 373, pp. 633-640.
Gracie, J. Alastair, et al., "Interleukin-12 induces interferon-gamma-dependent switching of IgG alloantibody subclass", Eur. J. Immunol., 1996, vol. 26, pp. 1217-1221.
Graham, D.S.C., et al., "Association of polymorphisms across the tyrosine kinase gene, TYK2 in UK SLE families", Rheumatology, 2007, vol. 46, pp. 927-930.
Hall, John C., et al., "Type I interferons: crucial participants in disease amplification in autoimmunity", Nat. Rev. Rheumatol., 2010, vol. 6, pp. 40-49.
Hong, Kenneth, et al., "IL-12, independently of IFN-gamma, Plays a Crucial Role in the Pathogenesis of a Murine Psoriasis-Like Skin Disorder", The Journal of Immunology, 1999. vol. 162, pp. 7480-7491.
Huang, Xinfang, et al., "Dysregulated expression of interleukin-23 and interleukin-12 subunits in systemic lupus erythematosus patients", Mod Rheumatol, 2007, vol. 17, pp. 220-223.
Hue, Sophie, et al., "Interleukin-23 drives innate and T cell-mediated intestinal inflammation", The Journal of Experimental Medicine, Oct. 30, 2006, vol. 203, No. 11, pp. 2473-2483.
Ishizaki, Masayuki, et al., "Involvement of Tyrosine Kinase-2 in Both the IL-12/Th1 and IL-23/Yh17 Axes In Vivo", The Journal of Immunology, 2011, vol. 187, pp. 181-189.

Kim, Daniel, et al., "Induction of Interferon-alpha by Scleroderma Sera Containing Autoantibodies to Topoisomerase I Association of Higher Interferon-alpha Activity With Lung Fibrosis", Arthritis and Rheumatism, vol. 58, No. 7, Jul. 2008, pp. 2163-2173.
Kyttaris, Vasileios C., et al., "Cutting Edge: IL-23 Receptor Deficiency Prevents the Development of Lupus Nephritis in C57BL/6-lpr/lpr Mice", The Journal of Immunology, 2010, vol. 184, pp. 4605-4609.
Lee, Edmund, et al., "Increased Expression of Interleukin 23 p19 and p40 in Lesional Skin of Patients with Psoriasis Vulgaris", J. Exp. Med., Jan. 5, 2004, vol. 199, No. 1, pp. 125-130.
Lees, C W. et al., "New IBD genetics: common pathways with other diseases", Gut, 2011, vol. 60, pp. 1739-1753.
Leonardi, Craig L., et al., "Efficacy and safety of ustekinumab, a human interleukin-12/23 monoclonal antibody, in patients with psoriasis: 76-week results from a randomised, double-blind, placebo-controlled trial (PHOENIX 1)", Lancet, 2008, vol. 371, pp. 1665-1674.
McGeachy, Mandy J., et al., "The link between IL-23 and Th17 cell-mediated immune pathologies", Seminars in Immunology, 2007, vol. 19, pp. 372-376.
Minegishi, Yoshiyuki, et al., "Human Tyrosine Kinase 2 Deficiency Reveals Its Requisite Roles in Multiple Cytokine Signals Involved in Innate and Acquired immunity", Immunity, Nov. 2006, vol. 25, pp. 745-755.
Murphy, Craig A., et al., "Divergent Pro- and Antiinflarnmatory Roles for IL-23 and IL-12 in Joint Autoimmune Inflammation", J. Exp. Med., Dec. 15, 2003, vol. 198, No. 12, pp. 1951-1957.
Oyamada, Akiko, et al., "Tyrosine Kinase 2 Plays Critical Roles in the Pathogenic CD4 T Cell Responses for the Development of Experimental Autoimmune Encephalomyelitis1", The Journal of immunology, 2009, vol. 183, pp. 7539-7546.
Peterson, Karin S., et al., "Characterization of heterogeneity in the molecular pathogenesis of lupus nephritis from transcriptional profiles of laser-captured glomeruli", The Journal of Clinical Investigation, 2004, vol. 113, pp. 1722-1733.
Prchal-Murphy, Michaela, et al., "TYK2 Kinase Activity is Required for Functional Type I Interferon Responses In Vivo", PLOs one, Jun. 2012, vol. 7, No. 6, pp. 1-12.
Sandborn, William J., et al., "A Randomized Trial of Ustekinumab, a Human Interleukin-12/23 Monoclonal Antibody, in Patients With Moderate-to-Severe Crohn's Disease", Gastroenterology, 2008, vol. 135, pp. 1130-1141.
Sandling, Johanna K., "A candidate gene study of the type I interferon pathway implicates IKBKE and IL8 as risk loci for SLE", European Journal of Human Genetics, 2011, vol. 19, pp. 479-484.
Santiago-Raber, Marie-Laure, et al., "Type-I interferon Receptor Deficiency Reduces Lupus-like Disease in NZB Mice", J. Exp. Med., Mar. 17, 2003, vol. 197, No. 6, pp. 777-788.
Tao, Jin-Hui, et al., "Meta-analysis of TYK2 gene polymorphisms association with susceptibility to autoimmune and inflammatory diseases", Mol Biol Rep, 2011, vol. 38, pp. 4663-4672.
Tucci, M., et al., "Overexpression of interleukin-12 and T helper 1 predominance in lupus nephritis", Clinical and Experimental Immunology, 2008, vol. 154, pp. 247-254.
Tzartos, John A., et al., "Interleukin-17 Production in Central Nervous System-Infiltrating T Cells and Glial Cells Is Associated with Active Disease in Multiple Sclerosis", The American Journal of Pathology, Jan. 2008, vol. 172. No. 1, pp. 146-155.

* cited by examiner

SULFONE PYRIDINE ALKYL AMIDE-SUBSTITUTED HETEROARYL COMPOUNDS

CROSS-REFERENCE TO RELATED APPLICATIONS

This application claims the benefit of U.S. Provisional Application No. 62/589,165, filed Nov. 21, 2017, the disclosure of which is incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are amide-substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", *Semin. Immunol.*, 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", *Eur. J. Immunol.*, 26:1217-1221 (1996); Schroder, K. et al., "Interferon-gamma: an overview of signals, mechanisms and functions", *J. Leukoc. Biol.*, 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", *J. Immunol.*, 184:4605-4609 (2010); Hong, K. et al., "IL-12, independently of IFN-gamma, plays a crucial role in the pathogenesis of a murine psoriasis like skin disorder", *J. Immunol.*, 162:7480-7491 (1999); Hue, S. et al., "Interleukin-23 drives innate and T cell-mediated intestinal inflammation", *J. Exp. Med.*, 203: 2473-2483 (2006); Cua, D. J. et al., "Interleukin-23 rather than interleukin-12 is the critical cytokine for autoimmune inflammation of the brain", *Nature*, 421:744-748 (2003); Murphy, C. A. et al., "Divergent pro- and anti-inflammatory roles for IL-23 and IL-12 in joint autoimmune inflammation", *J. Exp. Med.*, 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", *J. Exp. Med.*, 199:125-130 (2004); Tzartos, J. S. et al., "Interleukin-17 production in central nervous system infiltrating T cells and glial cells is associated with active disease in multiple sclerosis", *Am. J. Pathol.*, 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", *Mod. Rheumatol.*, 17:220-223 (2007)), and T cells from lupus patients have a predominant Th1 phenotype (Tucci, M. et al., "Overexpression of interleukin-12 and T helper 1 predominance in lupus nephritis", *Clin. Exp. Immunol.*, 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", *Gut*, 60:1739-1753 (2011); Tao, J. H. et al., "Meta-analysis of TYK2 gene polymorphisms association with susceptibility to autoimmune and inflammatory diseases", *Mol. Biol. Rep.*, 38:4663-4672 (2011); Cho, J. H. et al., "Recent insights into the genetics of inflammatory bowel disease", *Gastroenterology*, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", *Lancet*, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", *Gastroenterology*, 135:1130-1141 (2008); Gottlieb, A. et al., "Ustekinumab, a human interleukin 12/23 monoclonal antibody, for psoriatic arthritis: randomized, double-blind, placebo-controlled, crossover trial", *Lancet*, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", *Rheumatology (Oxford)*, 46:927-930 (2007); Eyre, S. et al., "High-density genetic mapping identifies new susceptibility loci for rheumatoid arthritis", *Nat. Genet.*, 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE
EMBODIMENTS OF THE INVENTION

In a first aspect of the present invention, there is provided a compound of formula (I)

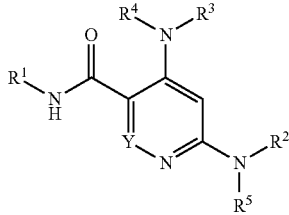

I wherein
Y is N or $CR^6$;
$R^1$ is H, $CD_3$ or $C_{1-3}$ alkyl;
$R^2$ is —C(O)$R^{2a}$; or $C_{1-6}$alkyl, —(CH$_2$)$_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;
$R^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O) NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3$R^a$, —(CH$_2$)$_r$-3-14 membered carbocycle substituted with 0-1 $R^a$ or a —(CH$_2$)$_r$-5-7 membered heterocycle containing 1-4 heteroatoms selected from N, O, and S(O)$_p$ substituted with 0-2 $R^a$;
$R^3$ is

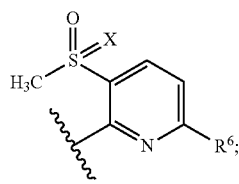

X is absent, O or NH;
$R^4$ and $R^5$ are independently hydrogen, $C_{1-4}$ alkyl substituted with 0-1 $R^f$, (CH$_2$)$_r$-phenyl substituted with 0-3 $R^d$ or a —(CH$_2$)-5-7 membered heterocycle containing 1-4 heteroatoms selected from N, O, and S(O)$_p$;
$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, NO$_2$ or OH;
$R^{11}$ at each occurrence is independently hydrogen, $C_{1-4}$ alkyl substituted with 0-3 $R^f$, CF$_3$, $C_{3-10}$ cycloalkyl substituted with 0-1 $R^f$, (CH$_2$)$_r$-phenyl substituted with 0-3 $R^d$ or —(CH$_2$)$_r$-5-7 membered heterocycle containing 1-4 heteroatoms selected from N, O, and S(O)$_p$ substituted with 0-3 $R^d$;

$R^a$ and $R^{a1}$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O) NR$^{11}$R$^{11}$, —(CH$_2$)$_r$NR$^b$C(O)R$^c$, —(CH$_2$)$_r$NR$^b$ C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 $R^f$;
$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle containing 1-4 heteroatoms selected from N, O, and S(O)$_p$ substituted with 0-3 $R^f$ or (CH$_2$)$_r$-phenyl substituted with 0-3 $R^d$;
$R^c$ is $C_{1-6}$ alkyl substituted with 0-3 $R^f$, (CH$_2$)$_r$—$C_{3-6}$ cycloalkyl substituted with 0-3 $R^f$ or (CH$_2$)$_r$-phenyl substituted with 0-3 $R^f$;
$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;
$R^e$ is independently at each occurrence, hydrogen, $C_{1-6}$ alkyl, $C_{3-6}$ cycloalkyl or (CH$_2$)$_r$-phenyl substituted with 0-3 $R^f$;
$R^f$ is independently at each occurrence, hydrogen, halo, CN, NH$_2$, OH, $C_{3-6}$ cycloalkyl, CF$_3$, O($C_{1-6}$ alkyl) or a —(CH$_2$)$_r$-5-7 membered heterocycle containing 1-4 heteroatoms selected from N, O, and S(O)$_p$;
p is 0, 1, or 2;
r is 0, 1, 2, 3, or 4;
or a stereoisomer or pharmaceutically acceptable salt thereof.

In a second aspect of the invention, there is provided a compound of formula II

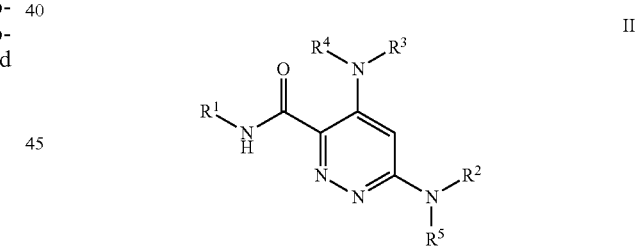

II wherein
$R^1$ is H, $CD_3$ or $C_{1-3}$ alkyl;
$R^2$ is —C(O)$R^{2a}$; or $C_{1-6}$ alkyl, —(CH$_2$)$_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;
$R^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O) NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle containing 1-4 heteroatoms selected from N, O, and S(O)$_p$ substituted with 0-2 $R^a$;

$R^3$ is

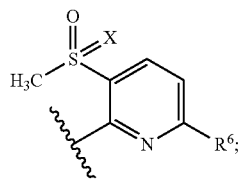

X is absent, O or NH;

$R^4$ and $R^5$ are independently hydrogen, $C_{1-4}$ alkyl substituted with 0-1 $R^f$, $(CH_2)_r$-phenyl substituted with 0-3 $R^d$ or a —$(CH_2)$-5-7 membered heterocycle containing 1-4 heteroatoms selected from N, O, and $S(O)_p$;

$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)NR^{11}R^{11}$, —$(CH_2)_r NR^b C(O)R^c$, —$(CH_2)_r NR^b C(O)_r OR^c$, —$NR^b C(O)NR^{11}R^{11}$, —$S(O)_p NR^{11}R^{11}$, —$NR^b S(O)_p R^c$, —$S(O)_2 R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_r C(O)R^c$, —$NR^e R^e$, —$NR^e C(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically acceptable salt thereof.

In a third aspect of the invention, there is provided a compound of formula III

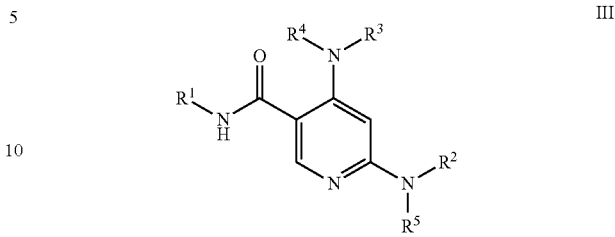

wherein $R^1$ is H, $CD_3$ or $C_{1-3}$ alkyl;

$R^2$ is —$C(O)R^{2a}$; or $C_{1-6}$ alkyl, —$(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, $OCF_3$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, $CH_2)_r NR^{11}R^{11}$, —$(CH_2)_r C(O)NR^{11}R^{11}$, —$(CH_2)_r NR^b C(O) R^c$, —$(CH_2)_r NR^b C(O)OR^c$, —$NR^b C(O)$ $NR^{11}R^{11}$, —$S(O)_p NR^{11}R^{11}$, —$NR^b S(O)_p$—$R^c$, —$S(O)_p R^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is

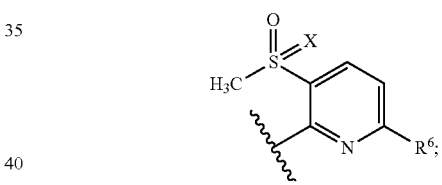

X is absent, O or NH;

$R^4$ and $R^5$ are independently hydrogen, $C_{1-4}$ alkyl substituted with 0-1 $R^f$, $(CH_2)_r$-phenyl substituted with 0-3 $R^d$ or a —$(CH_2)$-5-7 membered heterocycle containing 1-4 heteroatoms selected from N, O, and $S(O)_p$;

$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^{11}R^{11}$, —$(CH_2)_r C(O)$ $NR^{11}R^{11}$, —$(CH_2)_r NR^b C(O)R^c$, —$(CH_2)_r NR^b C(O)OR^c$, —$NR^b C(O)NR^{11}R^{11}$, —$S(O)_p NR^{11}R^{11}$, —$NR^b S(O)_p R^c$, —$S(O)_2 R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle containing 1-4 heteroatoms selected from N, O, and S(O)$_p$ substituted with 0-3 $R^f$ or (CH$_2$)$_r$-phenyl substituted with 0-3 $R^d$;

$R^c$ is $C_{1-6}$ alkyl substituted with 0-3 $R^f$, (CH$_2$)$_r$—$C_{3-6}$ cycloalkyl substituted with 0-3 $R^f$ or (CH$_2$)$_r$-phenyl substituted with 0-3 $R^f$;

$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^e$ is independently at each occurrence, hydrogen, $C_{1-6}$ alkyl, $C_{3-6}$ cycloalkyl or (CH$_2$)$_r$-phenyl substituted with 0-3 $R^f$;

$R^f$ is independently at each occurrence, hydrogen, halo, CN, NH$_2$, OH, $C_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically-acceptable salt thereof.

In a 4th aspect of the invention, there is provided a compound according to the first and second aspects of formula II

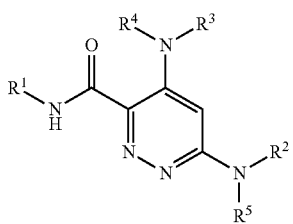

II wherein $R^1$ is H, CD$_3$ or $C_{1-3}$ alkyl;

$R^2$ is —C(O)R$^{2a}$; or $C_{1-6}$ alkyl, —(CH$_2$)$_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O) NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle containing 1-4 heteroatoms selected from N, O, and S(O)$_p$ substituted with 0-2 $R^a$;

$R^3$ is

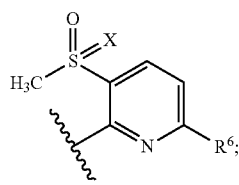

X is O;

$R^4$ and $R^5$ are independently hydrogen, $C_{1-4}$ alkyl substituted with 0-1 $R^f$, (CH$_2$)$_r$-phenyl substituted with 0-3 $R^d$ or a —(CH$_2$)-5-7 membered heterocycle containing 1-4 heteroatoms selected from N, O, and S(O)$_p$;

$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, NO$_2$ or OH;

$R^{11}$ at each occurrence is independently hydrogen, $C_{1-4}$ alkyl substituted with 0-3 $R^f$, CF$_3$, $C_{3-10}$ cycloalkyl substituted with 0-1 $R^f$, (CH$_2$)$_r$-phenyl substituted with 0-3 $R^d$ or —(CH$_2$)$_r$-5-7 membered heterocycle containing 1-4 heteroatoms selected from N, O, and S(O)$_p$ substituted with 0-3 $R^d$;

$R^a$ and $R^{a1}$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O) NR$^{11}$R$^{11}$, —(CH$_2$)$_r$NR$^b$C(O)R$^c$, —(CH$_2$)$_r$NR$^b$ C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle containing 1-4 heteroatoms selected from N, O, and S(O)$_p$ substituted with 0-3 $R^f$ or (CH$_2$)$_r$-phenyl substituted with 0-3 $R^d$;

$R^c$ is $C_{1-6}$ alkyl substituted with 0-3 $R^f$, (CH$_2$)$_r$—$C_{3-6}$ cycloalkyl substituted with 0-3 $R^f$ or (CH$_2$)$_r$-phenyl substituted with 0-3 $R^f$;

$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^e$ is independently at each occurrence, hydrogen, $C_{1-6}$ alkyl, $C_{3-6}$ cycloalkyl or (CH$_2$)$_r$-phenyl substituted with 0-3 $R^f$;

$R^f$ is independently at each occurrence, hydrogen, halo, CN, NH$_2$, OH, $C_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically-acceptable salt thereof.

In a 5th aspect of the invention, there is provided a compound of the formula

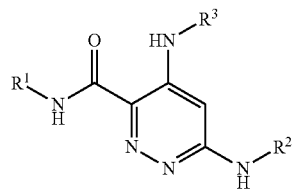

wherein $R^1$ is H, CD$_3$ or $C_{1-3}$ alkyl;

$R^2$ is —C(O)R$^{2a}$; or $C_{1-6}$ alkyl, —(CH$_2$)$_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{1-6}$ haloalkyl, $C_{2-6}$ alkenyl substituted with 0-3 $R^a$, $-(CH_2)_r$-3-14 membered carbocycle substituted with 0-1 $R^a$ or a $-(CH_2)_r$-5-7 membered heterocycle containing 1-4 heteroatoms selected from N, O, and $S(O)_p$ substituted with 0-2 $R^a$;

$R^3$ is

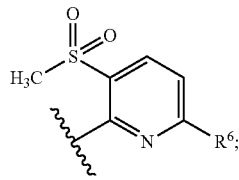

$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or $-(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle or $-(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or $-(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, $-(CH_2)_rC(O)R^c$, $-NR^eR^e$, $-NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a $-(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically-acceptable salt thereof.

In a 6th aspect of the invention, there is provided a compound of the formula

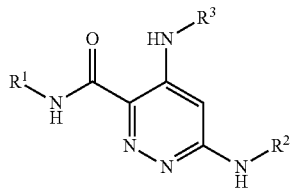

wherein $R^1$ is H, $CD_3$ or $C_{1-3}$ alkyl;

$R^2$ is $-C(O)R^{2a}$; or $C_{1-6}$ alkyl, $-(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{1-6}$ haloalkyl, $C_{2-6}$ alkenyl substituted with 0-3 $R^a$, $-(CH_2)_r$-3-14 membered carbocycle substituted with 0-1 $R^a$ or a $-(CH_2)_r$-5-7 membered heterocycle containing 1-4 heteroatoms selected from N, O, and $S(O)_p$ substituted with 0-2 $R^a$;

$R^3$ is

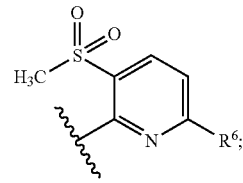

$R^6$ is hydrogen, halo, $C_{1-3}$ alkyl, $C_{1-3}$ alkyoxy or $C_{3-6}$ cycloalkyl;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or $-(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle or $-(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or $-(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically-acceptable salt thereof.

In a 7th aspect of the invention, there is provided a compound of the formula

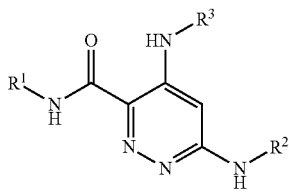

wherein $R^1$ is H, $CD_3$ or $C_{1-3}$ alkyl;

$R^2$ is —$C(O)R^{2a}$;

$R^{2a}$ at each occurrence is independently hydrogen, OH, halo, $OCF_3$, $C_{1-6}$ alkyl substituted with 0-2 $R^a$, $C_{1-6}$ haloalkyl, $C_{1-6}$ alkoxy substituted with 0-2 $R^a$, $C_{2-6}$ alkenyl substituted with 0-2 $R^a$ or $C_{3-6}$ cycloalkyl substituted with 0-2 $R^a$;

$R^3$ is

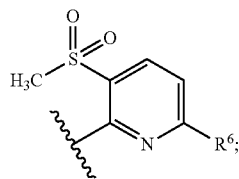

$R^6$ is hydrogen, halo, $C_{1-3}$ alkyl, $C_{1-3}$ alkyoxy or $C_{3-6}$ cycloalkyl;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^b C(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically-acceptable salt thereof.

In an 8th aspect of the invention, there is provided a compound of the formula

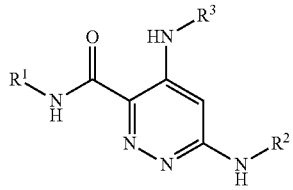

wherein $R^1$ is H, $CD_3$ or $C_{1-3}$ alkyl;

$R^2$ is pyridine, pyridazine, pyrimidine, pyrazine, pyrazole, triazole, isoxazole, isothiazole or quinoline, each group substituted with 0-4 $R^{2a}$;

$R^{2a}$ at each occurrence is independently hydrogen, OH, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, $(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)$ $NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is

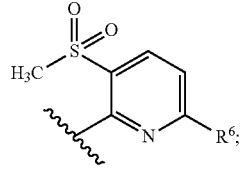

$R^6$ is hydrogen, halo, $C_{1-3}$ alkyl, $C_{1-3}$ alkyoxy or $C_{3-6}$ cycloalkyl;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^b C(O)OR^c$, —$NR^bC(O)NR^{11}R^{11}$, —$S(O)_pNR^{11}R^{11}$, —$NR^bS(O)_pR^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically acceptable salt thereof.

In a 9th aspect of the invention, there is provided a compound of formula III

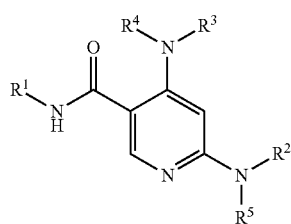

III $R^1$ is H, $CD_3$ or $C_{1-3}$ alkyl;

$R^2$ is —$C(O)R^{2a}$; or $C_{1-6}$ alkyl, —$(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, $CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is

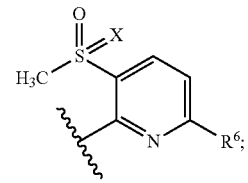

X is O;

$R^4$ and $R^5$ are independently hydrogen, $C_{1-4}$ alkyl substituted with 0-1 $R^f$, $(CH_2)_r$-phenyl substituted with 0-3 $R^d$ or a —$(CH_2)_r$-5-7 membered heterocycle containing 1-4 heteroatoms selected from N, O, and $S(O)_p$;

$R^6$ is hydrogen, halo, $C_{1-4}$ alkyl, $C_{1-4}$ haloalkyl, —$OC_{1-4}$ haloalkyl, $OC_{1-4}$ alkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^b C(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically acceptable salt thereof.

In a 10th aspect of the invention, there is provided a compound of the formula

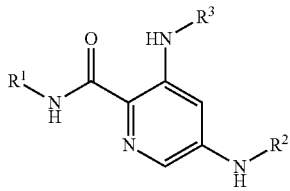

wherein
R$^1$ is H, CD$_3$ or C$_{1-3}$ alkyl;
R$^2$ is —C(O)R$^{2a}$; or —(CH$_2$)$_r$-3-14 membered carbocycle substituted with 0-1 R$^{2a}$ or a 5-14 membered heterocycle containing 1-4 heteroatoms selected from N, O, and S, substituted with 0-4 R$^{2a}$;
R$^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O) OR$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;
R$^3$ is

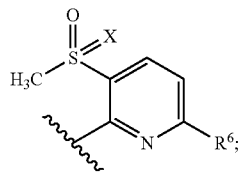

X is O;
R$^6$ is hydrogen, halo, C$_{1-3}$ alkyl, C$_{1-3}$ alkyoxy or C$_{3-6}$ cycloalkyl;
R$^{11}$ at each occurrence is independently hydrogen, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;
R$^a$ and R$^{a1}$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O) NR$^{11}$R$^{11}$, —(CH$_2$)$_r$NR$^b$C(O)R$^c$, —(CH$_2$)$_r$NR$^b$ C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;
R$^b$ is hydrogen, C$_{1-6}$ alkyl substituted with 0-3 R$^d$, C$_{1-6}$ haloalkyl, C$_{3-6}$ cycloalkyl substituted with 0-2 R$^d$ or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;
R$^d$ at each occurrence is independently hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;
R$^e$ at each occurrence is independently selected from hydrogen, C$_{1-6}$ alkyl, C$_{3-6}$ cycloalkyl and (CH$_2$)$_r$-phenyl substituted with 0-3 R$^f$;
R$^f$ independently at each occurrence is hydrogen, halo, CN, NH$_2$, OH, C$_{3-6}$ cycloalkyl, CF$_3$, O(C$_{1-6}$alkyl) or a —(CH$_2$)$_r$-5-7 membered heterocycle containing 1-4 heteroatoms selected from N, O, and S(O)$_p$;
p is 0, 1, or 2;
r is 0, 1, 2, 3, or 4;
or a stereoisomer or pharmaceutically-acceptable salt thereof.

In another aspect, there is provided a compound selected from the exemplified examples within the scope of the first aspect, or a pharmaceutically acceptable salt or stereoisomer thereof.

In another aspect, there is provided a compound selected from any subset list of compounds within the scope of any of the above aspects.

In another aspect, there is provided a compound (IUPAC naming convention) selected from
6-cyclopropaneamido-4-[(3-methanesulfonylpyridin-2-yl)amino]-N—($^2$H$_3$)methylpyridazine-3-carboxamide;
6-[(5-fluoropyridin-2-yl)amino]-4-[(3-methanesulfonylpyridin-2-yl)amino]-N—($^2$H$_3$)methylpyridazine-3-carboxamide;
4-[(3-methanesulfonylpyridin-2-yl)amino]-6-[(6-methoxypyridazin-3-yl)amino]-N—($^2$H$_3$)methylpyridazine-3-carboxamide;
4-[(3-methanesulfonylpyridin-2-yl)amino]-N—($^2$H$_3$) methyl-6-[(1-methyl-1H-pyrazol-3-yl)amino]pyridazine-3-carboxamide;
6-[(6-cyclopropyl-2-methylpyrimidin-4-yl)amino]-4-[(3-methanesulfonylpyridin-2-yl)amino]-N—($^2$H$_3$)methylpyridazine-3-carboxamide;
6-{[5-(2-hydroxypropan-2-yl)pyridin-2-yl]amino}-4-[(3-methanesulfonylpyridin-2-yl)amino]-N—($^2$H$_3$)methylpyridazine-3-carboxamide;
6-[(6-cyclopropylpyrimidin-4-yl)amino]-4-[(3-methanesulfonylpyridin-2-yl)amino]-N—($^2$H$_3$)methylpyridazine-3-carboxamide;
6-[(6-cyclopropylpyridazin-3-yl)amino]-4-[(3-methanesulfonylpyridin-2-yl)amino]-N—($^2$H$_3$)methylpyridazine-3-carboxamide;
6-[(1,5-dimethyl-1H-pyrazol-3-yl)amino]-4-[(3-methanesulfonylpyridin-2-yl)amino]-N—($^2$H$_3$)methylpyridazine-3-carboxamide;
4-[(3-methanesulfonylpyridin-2-yl)amino]-N—($^2$H$_3$) methyl-6-{[5-(trifluoromethyl)pyridin-2-yl]amino}pyridine-3-carboxamide;
4-[(3-methanesulfonylpyridin-2-yl)amino]-N—($^2$H$_3$) methyl-6-{[6-(trifluoromethyl)pyridazin-3-yl]amino}pyridazine-3-carboxamide;
4-[(3-methanesulfonylpyridin-2-yl)amino]-6-[(2-methoxypyrimidin-4-yl)amino]-N—($^2$H$_3$)methylpyridazine-3-carboxamide;
6-{[5-fluoro-4-(2-hydroxypropan-2-yl)pyridin-2-yl] amino}-4-[(3-methanesulfonylpyridin-2-yl)amino]-N—($^2$H$_3$)methylpyridazine-3-carboxamide;

6-{[5-(2-aminopropan-2-yl)pyridin-2-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[1-(2,2,2-trifluoroethyl)-1H-pyrazol-3-yl]amino}pyridazine-3-carboxamide;

4-[(3-methanesulfonylpyridin-2-yl)amino]-6-{[6-($^2$H$_3$)methoxypyridazin-3-yl]amino}-N—($^2$H$_3$)methylpyridazine-3-carboxamide;

6-[(5-cyanopyridin-2-yl)amino]-4-[(3-methanesulfonylpyridin-2-yl)amino]-N—($^2$H$_3$)methylpyridine-3-carboxamide;

methyl N-{2-[6-({5-[(3-methanesulfonylpyridin-2-yl)amino]-6-[($^2$H$_3$)methylcarbamoyl]pyridazin-3-yl}amino)pyridin-3-yl]propan-2-yl}carbamate;

6-{[5-(1-cyanocyclopropyl)pyridin-2-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[5-(morpholin-4-yl)pyridin-2-yl]amino}pyridazine-3-carboxamide;

6-[(5-cyclopropylpyrazin-2-yl)amino]-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-[(6-methylpyridazin-3-yl)amino]pyridazine-3-carboxamide;

4-[(3-methanesulfonylpyridin-2-yl)amino]-N—($^2$H$_3$)methyl-6-{[5-(trifluoromethyl)pyridin-2-yl]amino}pyridazine-3-carboxamide;

4-[(3-methanesulfonylpyridin-2-yl)amino]-N—($^2$H$_3$)methyl-6-[(5-methylpyrazin-2-yl)amino]pyridazine-3-carboxamide;

4-[(3-methanesulfonylpyridin-2-yl)amino]-6-{[4-(methoxymethyl)pyridin-2-yl]amino}-N—($^2$H$_3$)methylpyridazine-3-carboxamide;

6-[(2,6-dimethylpyrimidin-4-yl)amino]-4-[(3-methanesulfonylpyridin-2-yl)amino]-N—($^2$H$_3$)methylpyridazine-3-carboxamide;

6-{[6-(2,6-difluorophenyl)pyridazin-3-yl]amino}-4-[(3-methanesulfonylpyridin-2-yl)amino]-N—($^2$H$_3$)methylpyridazine-3-carboxamide;

6-cyclopropaneamido-4-[(3-methanesulfonylpyridin-2-yl)amino]-N—($^2$H$_3$)methylpyridine-3-carboxamide;

6-[(1S,2R)-2-fluorocyclopropaneamido]-4-[(3-methanesulfonylpyridin-2-yl)amino]-N—($^2$H$_3$)methylpyridazine-3-carboxamide;

6-[(1S,2S)-2-fluorocyclopropaneamido]-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-[(1R,2R)-2-methylcyclopropaneamido]pyridazine-3-carboxamide;

4-[(3-methanesulfonylpyridin-2-yl)amino]-N—($^2$H$_3$)methyl-6-{spiro[2.2]pentane-1-amido}pyridazine-3-carboxamide;

4-[(3-methanesulfonylpyridin-2-yl)amino]-N—($^2$H$_3$)methyl-6-[(1R,2R)-2-methylcyclopropaneamido]pyridazine-3-carboxamide;

6-[(6-cyclopropylpyrimidin-4-yl)amino]-4-[(3-methanesulfonylpyridin-2-yl)amino]-N—($^2$H$_3$)methylpyridine-3-carboxamide;

4-[(3-methanesulfonylpyridin-2-yl)amino]-N—($^2$H$_3$)methyl-6-[(2-methyl-2H-1,2,3-triazol-4-yl)amino]pyridazine-3-carboxamide;

6-[(6-cyclopropyl-2-methylpyrimidin-4-yl)amino]-4-[(3-methanesulfonylpyridin-2-yl)amino]-N—($^2$H$_3$)methylpyridine-3-carboxamide;

6-{[5-(2-hydroxypropan-2-yl)pyridin-2-yl]amino}-4-[(3-methanesulfonyl-6-methylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[5-(trifluoromethoxy)pyridin-2-yl]amino}pyridazine-3-carboxamide;

4-[(3-methanesulfonylpyridin-2-yl)amino]-N—($^2$H$_3$)methyl-6-[(1S)-spiro[2.2]pentane-1-amido]pyridazine-3-carboxamide;

4-[(3-methanesulfonylpyridin-2-yl)amino]-N—($^2$H$_3$)methyl-6-[(1R)-spiro[2.2]pentane-1-amido]pyridazine-3-carboxamide;

6-{[4-chloro-5-(2-hydroxypropan-2-yl)pyridin-2-yl]amino}-4-[(3-methanesulfonyl-6-methylpyridin-2-yl)amino]-N—($^2$H$_3$)methylpyridazine-3-carboxamide;

6-cyclopropaneamido-4-[(3-methanesulfonyl-6-methylpyridin-2-yl)amino]-N—($^2$H$_3$)methylpyridine-3-carboxamide;

6-{[4-chloro-5-(2-hydroxypropan-2-yl)pyridin-2-yl]amino}-4-[(3-methanesulfonyl-6-methoxypyridin-2-yl)amino]-N—($^2$H$_3$)methylpyridazine-3-carboxamide;

6-[(2-cyclopropyl-6-methylpyrimidin-4-yl)amino]-4-[(3-methanesulfonylpyridin-2-yl)amino]-N—($^2$H$_3$)methylpyridazine-3-carboxamide;

6-{[6-fluoro-5-(2-hydroxypropan-2-yl)pyridin-2-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-6-{[5-(methoxymethyl)pyridin-2-yl]amino}-N—($^2$H$_3$)methylpyridazine-3-carboxamide;

4-[(3-methanesulfonylpyridin-2-yl)amino]-6-({5-[($^2$H$_3$)methoxymethyl]pyridin-2-yl}amino)-N—($^2$H$_3$)methylpyridazine-3-carboxamide;

6-{[6-(difluoromethoxy)pyridazin-3-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[6-(propan-2-yl)pyridazin-3-yl]amino}pyridazine-3-carboxamide;

6-[(6-tert-butylpyridazin-3-yl)amino]-4-[(3-methanesulfonylpyridin-2-yl)amino]-N—($^2$H$_3$)methylpyridazine-3-carboxamide;

6-{[6-(difluoromethyl)pyridazin-3-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-[(1S,2S)-2-methylcyclopropaneamido]pyridazine-3-carboxamide; or 6-cyclopropaneamido-4-[(3-methanesulfonyl-6-methylpyridin-2-yl)amino]-N—($^2$H$_3$)methylpyridazine-3-carboxamide;

or a stereoisomer or pharmaceutically acceptable salt thereof.

In another aspect, there is provided a compound (IUPAC naming convention) selected from 6-cyclopropaneamido-4-[(3-methanesulfonylpyridin-2-yl)amino]-N—($^2$H$_3$)methylpyridazine-3-carboxamide;

6-[(6-cyclopropyl-2-methylpyrimidin-4-yl)amino]-4-[(3-methanesulfonylpyridin-2-yl)amino]-N—($^2$H$_3$)methylpyridazine-3-carboxamide;

6-[(6-cyclopropylpyrimidin-4-yl)amino]-4-[(3-methanesulfonylpyridin-2-yl)amino]-N—($^2$H$_3$)methylpyridazine-3-carboxamide;

6-[(6-cyclopropylpyridazin-3-yl)amino]-4-[(3-methanesulfonylpyridin-2-yl)amino]-N—($^2$H$_3$)methylpyridazine-3-carboxamide;

6-cyclopropaneamido-4-[(3-methanesulfonylpyridin-2-yl)amino]-N—($^2$H$_3$)methylpyridine-3-carboxamide;

4-[(3-methanesulfonylpyridin-2-yl)amino]-N—($^2$H$_3$)methyl-6-[(1R,2R)-2-methylcyclopropaneamido]pyridazine-3-carboxamide;

4-[(3-methanesulfonylpyridin-2-yl)amino]-N—($^2$H$_3$)methyl-6-{spiro[2.2]pentane-1-amido}pyridazine-3-carboxamide;

4-[(3-methanesulfonylpyridin-2-yl)amino]-N—($^2$H$_3$)methyl-6-[(1S,2S)-2-methylcyclopropaneamido]pyridazine-3-carboxamide;

6-cyclopropaneamido-4-[(3-methanesulfonyl-6-methylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[5-(trifluoromethoxy)pyridin-2-yl]amino}pyridazine-3-carboxamide;

4-[(3-methanesulfonylpyridin-2-yl)amino]-N—($^2$H$_3$)methyl-6-[(1S)-spiro[2.2]pentane-1-amido]pyridazine-3-carboxamide;

4-[(3-methanesulfonylpyridin-2-yl)amino]-N—($^2$H$_3$)methyl-6-[(1R)-spiro[2.2]pentane-1-amido]pyridazine-3-carboxamide; or 6-{[4-chloro-5-(2-hydroxypropan-2-yl)pyridin-2-yl]amino}-4-[(3-methanesulfonyl-6-methylpyridin-2-yl)amino]-N—($^2$H$_3$)methylpyridazine-3-carboxamide or a stereoisomer or pharmaceutically acceptable salt thereof, In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of said diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating an IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating an IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

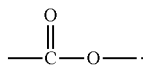

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

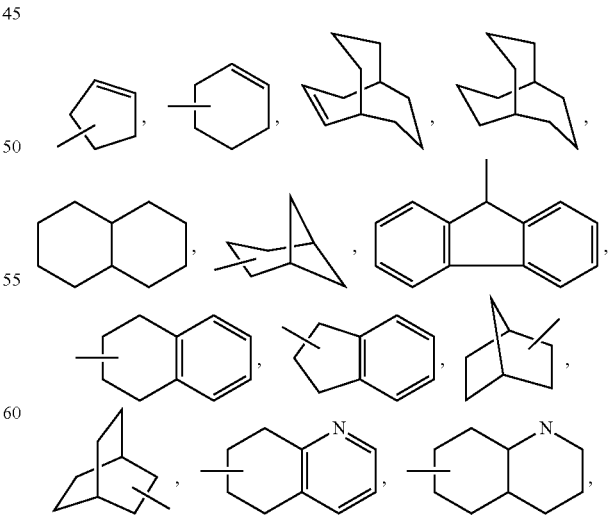

and the like, which optionally may be substituted at any available atoms of the ring(s).

Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

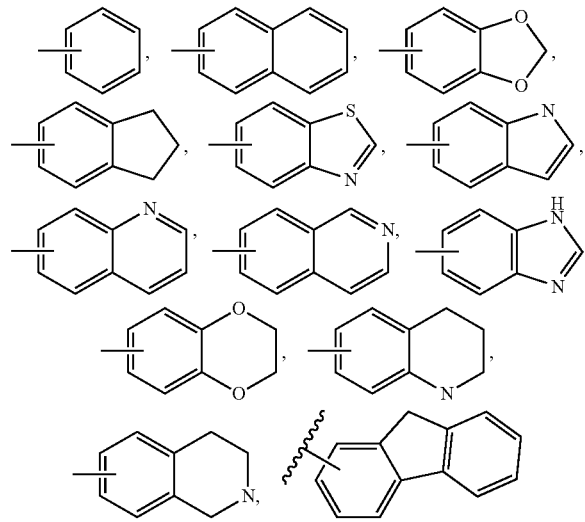

(fluorenyl) and the like, which optionally may be substituted at any available carbon or nitrogen atom.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

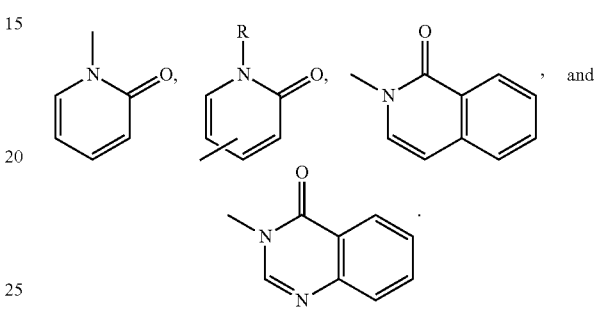

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include:

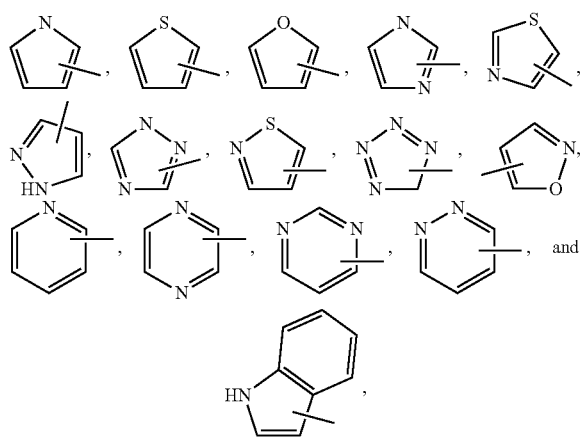

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991); and c) Bundgaard, H., *Adv. Drug Deliv. Rev.,* 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

UTILITY

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

METHODS OF PREPARATION

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Chemical names were determined using ChemDraw Ultra, version 9.0.5 (CambridgeSoft). The following abbreviations are used:

Abbreviations

| Abbreviation | Meaning |
|---|---|
| Ac | acetyl |
| ACN | acetonitrile |
| AcOH | acetic acid |
| anhyd. | anhydrous |
| aq. | aqueous |
| Bn | benzyl |
| Bu | butyl |
| Boc | tert-butoxycarbonyl |
| BOP | benzotriazol-1-yloxytris-(dimethylamino)-phosphonium hexafluorophosphate |
| CV | Column Volumes |
| DCE | dichloroethane |
| DCM | dichloromethane |
| DIPEA | diisopropylethylamine |
| DMF | dimethylformamide |
| DMSO | dimethylsulfoxide |
| EtOAc | ethyl acetate |
| Et | ethyl |
| EtOH | ethanol |
| H or $H_2$ | hydrogen |
| h, hr or hrs | hour(s) |
| HATU | O-(7-azabenzotriazol-1-yl)-N, N, N', N'-tetramethyluronium hexafluorophosphate |
| hex | hexane |
| i | iso |
| IPA | isopropyl alcohol |
| ISCO | automated chromatography |
| HOAc | acetic acid |
| HCl | hydrochloric acid |
| HPLC | high pressure liquid chromatography |
| LC | liquid chromatography |
| LIHMDS | Lithium bis(trimethylsilyl)amide |
| M | molar |
| mM | millimolar |
| Me | methyl |
| MeOH | methanol |
| MHz | megahertz |
| min. | minute(s) |
| mins | minute(s) |
| M + 1 | (M + H)+ |

-continued

| Abbreviation | Meaning |
|---|---|
| MS | mass spectrometry |
| n or N | normal |
| nm | nanometer |
| nM | nanomolar |
| NMP | N-methylpyrrolidine |
| Pd/C | palladium on carbon |
| $PdCl_2(dppf)_2$ | [1,1'-bis(diphenylphosphino)ferrocene]dichloropalladium(II) |
| $Pd_2dba_3$ | Tris(dibenzylideneacetone)dipalladium(0) |
| Ph | phenyl |
| $PPh_3$ | triphenylphosphine |
| Pr | propyl |
| PSI | pounds per square inch |
| rb | round bottle |
| rt | room temperature |
| Ret Time | retention time |
| sat. | saturated |
| SFC | supercritical fluid chromatography |
| TEA | triethylamine |
| TFA | trifluoroacetic acid |
| THF | tetrahydrofuran |

Preparations

The preparations set out below are for the synthesis of reagents that were not obtained from commercial sources and were employed for the preparation of compounds of formula I of the invention. All chiral compounds in the Tables and Schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:
Method A (used in all cases, unless otherwise indicated):
  Linear gradient of 0 to 100% solvent B over 4 minutes ("min"), with 1 minute ("min") hold at 100% B
  Ultraviolet ("UV") visualization at 220 nanometers ("nm")
  Column: YMC S5 ODS Ballistic 4.6×50 mm
  Flow rate: 4 milliliters ("mL")/min
  Solvent A: 0.2% phosphoric acid, 90% water, 10% methanol
  Solvent B: 0.2% phosphoric acid, 90% methanol, 10% water
Method B:
  Column: PHENOMENEX® Luna C18(2), 4.6×50 mm×5 µm
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
  Detection:
    Detector 1: UV at 220 nm
    Detector 2: MS(ESI+)
    Detector 3: ELSD Method C:
  Column: Waters SunFire C18, 4.6×50 mm×5 μm
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
  Detection:
    Detector 1: UV at 220 nm
    Detector 2: MS(ESI+)
    Detector 3: ELSD
Method D:
  Column: Acquity BEH C18, 2.1×50 mm×1.7 μm
  Mobile Phase: (A) water; (B) acetonitrile
  Buffer: 0.05% TFA
  Gradient Range: 2-98% B (1 min); 98% B (0.5 min); 98-2% B (0.6 min)
  Run time: 1.7 min
  Flow Rate: 0.8 mL/min
  Analysis Time: 1.7 min
  Detection:
    Detector 1: UV at 254 nm
    Detector 2: MS(ESI+)
Method E:
  Column: Waters XBridge C18, 2.1×50 mm×1.7 μm
  Mobile Phase: (A) 5:95 acetonitrile:water (B) 95:5 methanol:water
  Buffer: 0.1% TFA
  Gradient: 0-100% B
  Gradient time: 3 min
  Run time: 3.75 min
  Flow Rate: 1 mL/min
  Analysis Time: 3.75 min
  Detection:
    Detector 1: UV at 254 nm
    Detector 2: MS(ESI+)

Intermediate 1

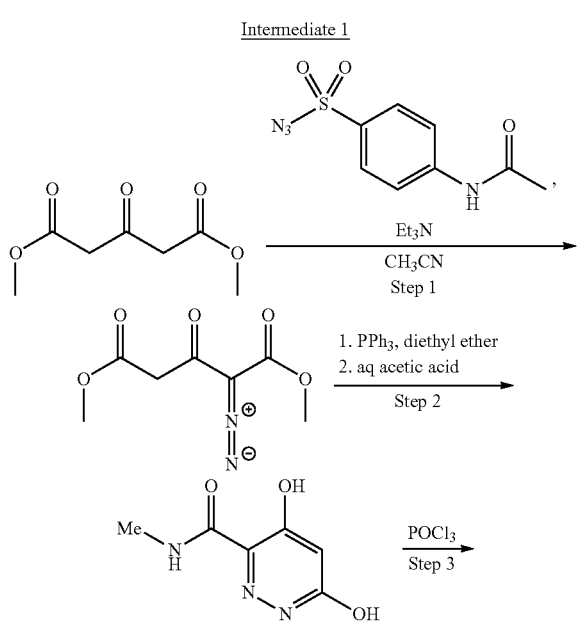

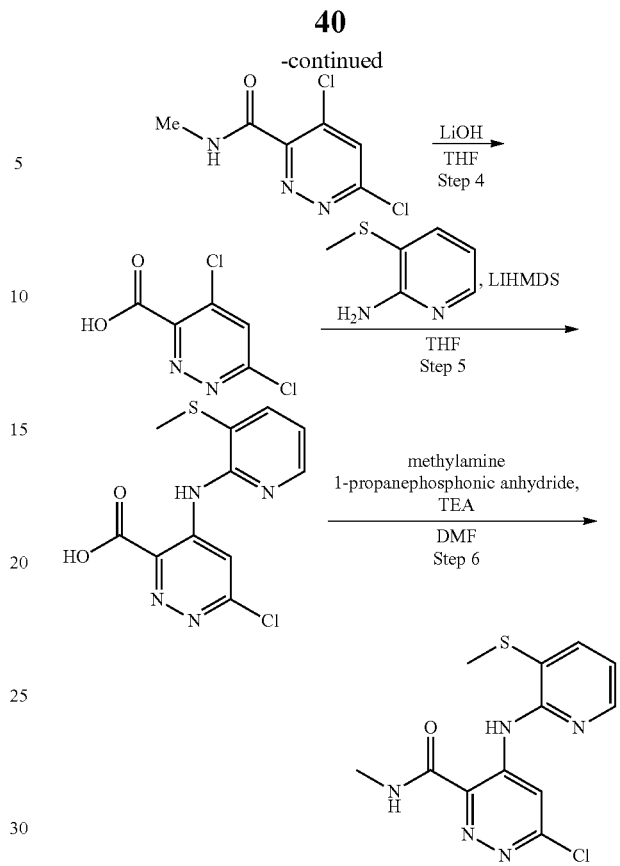

Step 1
  Dimethyl 3-oxopentanedioate (3.77 g, 21.65 mmol) was dissolved in acetonitrile (70 mL) and triethylamine (3.02 mL, 21.65 mmol) was added. After cooling to 0° C., 4-acetamidobenzenesulfonyl azide (5.2 g, 21.65 mmol) was added slowly to the reaction portionwise over ~5 minutes. After addition was nearly complete, a heavy yellow precipitate formed. The mixture was stirred at rt for ~1 h and then was filtered to remove the precipitated solid. The filter cake was rinsed sparingly with additional ACN until the yellow color was completely washed away from the solid to give a white solid and a cloudy yellow filtrate. The filtrate containing the product was concentrated in vacuo to yield a yellow solid, which was slurried in a 1:1 mixture of hexanes/Et₂O (~150 mL) and the suspension was again filtered. The solid was rinsed sparingly with additional 1:1 hexanes/Et₂O and the resulting yellow turbid filtrate was concentrated to afford 4.59 g of a yellow oil containing a small amount of solid as the crude product mixture containing dimethyl 2-diazo-3-oxopentanedioate. This material was used directly in the next step.

Step 2
  To a mixture of the crude product dimethyl 2-diazo-3-oxopentanedioate (20.92 g, 104 mmol) in diethyl ether (250 mL) at rt was added Ph₃P (27.3 g, 104 mmol) and the resulting mixture was stirred at rt for 1 day. The heterogeneous reaction mixture was concentrated to remove the ether and the resulting solids were taken up in AcOH (240 mL) and water (24 mL) and refluxed for 4 h. The reaction was cooled and concentrated in vacuo to give a pale yellow semi solid which was co-evaporated with 2 portions of toluene (2×50 mL) to remove the residual AcOH. The resulting solids were then slurried in 75 mL of sat. aq sodium carbonate and 75 mL of water and the mixture was extracted with DCM (4×200 mL) to remove the impurities. The aqueous layers were filtered to give a clear yellow solution which was cooled in an ice bath and carefully made acidic by a dropwise addition of 6N aq HCl. Once the desired pH was reached (~1-2), a heavy cream colored precipitate formed. The mixture was stirred at 0° C. for ~5 min, then the solid was collected by vacuum filtration and rinsed sparingly with ice cold water. The solid was allowed to partially air dry in the funnel then the still moist solid was transferred into an rb flask and allowed to dry under vacuum over the weekend to give methyl 4,6-dihydroxypyridazine-3-carboxylate (11.76 g, 69.1 mmol, 66.5% yield).

Step 3

A slurry of methyl 4,6-dihydroxypyridazine-3-carboxylate (11.7 g, 68.8 mmol) in POCl$_3$ (110 mL, 1180 mmol) was heated to reflux for 3 h during which time the mixture became a nearly homogeneous dark brown solution. The reaction mixture was cooled to rt, allowed to stand overnight and concentrated in vacuo. The resulting dark brown residue was dissolved in DCM (~300 mL) and was slowly poured onto ~500 mL of crushed ice with swirling of the flask. After the addition was complete, water was slowly added (~200 mL) until the mixture became stirrable and the mixture was stirred while warming to rt over ~3 h. The resulting phases were separated and the aqueous portion was extracted with additional DCM (3×100 mL). The combined extracts were washed with brine, dried over anhydrous sodium sulfate, decanted and concentrated under vacuum to afford a white solid as the pure product, methyl 4,6-dichloropyridazine-3-carboxylate (9.16 g, 44.2 mmol, 64.3% yield). Material was used as is without any further purification.

MS (M+1) m/z: 206.9 (MH$^+$). LC retention time 0.80 min [A].

Step 4

To a solution of methyl 4,6-dichloropyridazine-3-carboxylate (5.5 g, 26.6 mmol) in THF (60 mL), at 0° C. was added 1M solution of lithium hydroxide (39.9 mL, 39.9 mmol) with stirring. The resultant mixture was stirred continuously at 0° C. for 40 min. The THF was removed and the aqueous layer was acidified with 1.5N HCl to give a white solid. The mixture was filtered and the solid filter cake was washed with water and dried under vacuum overnight to give 4,6-dichloropyridazine-3-carboxylic acid (5 g, 25.9 mmol, 98% yield).

MS (M+1) m/z: 193 (MH$^+$). LC retention time 0.19 min [D].

Step 5

To a THF (20 mL) solution of 4,6-dichloropyridazine-3-carboxylic acid (0.734 g, 3.80 mmol) and 3-(methylthio)pyridin-2-amine (0.68 g, 4.85 mmol) was added LIHMDS (9.51 mL, 9.51 mmol) slowly at 0° C. The reaction was stirred at 0° C. for 15 min and then warmed to room temperature for 2 h. The reaction was quenched with water (~5 mL) and acidified with HCl (1N, 15 mL). The resulting precipitate was filtered, washed with water and dried under vacuum overnight to give as an orange solid 6-chloro-4-((3-(methylthio)pyridin-2-yl)amino)pyridazine-3-carboxylic acid (0.712 g, 2.40 mmol, 63.1% yield).

MS (M+1) m/z: 297.0 (MH$^+$). LC retention time 0.86 min [A].

1H NMR (400 MHz, DMSO-d6) δ 11.46 (s, 1H), 9.15 (s, 1H), 8.34 (dd, J=4.9, 1.7 Hz, 1H), 7.95 (dd, J=7.7, 1.7 Hz, 1H), 7.18 (dd, J=7.7, 4.8 Hz, 1H), 2.53 (s, 3H).

Step 6

1-propanephosphonic anhydride (0.409 mL, 0.700 mmol) was added to a DMF (1.9 mL) solution of 6-chloro-4-((3-(methylthio)pyridin-2-yl)amino)pyridazine-3-carboxylic acid (0.1385 g, 0.467 mmol) and TEA (0.130 mL, 0.933 mmol) at room temperature. After 2 min, a suspension was formed. The reaction was stirred at room temperature for 1 hour before the addition of methylamine (0.439 g, 4.67 mmol). The reaction was stirred for 2 hours at room temperature, diluted with water and the suspension filtered and washed with water. The solid was dried under vacuum overnight to give the product 6-chloro-N-methyl-4-((3-(methylthio)pyridin-2-yl)amino)pyridazine-3-carboxamide (0.112 g, 0.362 mmol, 78% yield, Intermediate 1).

MS (M+1) m/z: 311.1 (MH$^+$). LC retention time 0.92 min [E].

NMR (400 MHz, DMSO-d6) δ 12.35-12.30 (m, 1H), 9.49 (br d, J=4.4 Hz, 1H), 9.14 (s, 1H), 8.30 (dd, J=4.8, 1.4 Hz, 1H), 7.93-7.87 (m, 1H), 7.16 (dd, J=7.7, 4.9 Hz, 1H), 2.88 (d, J=4.9 Hz, 3H), 2.55 (s, 3H).

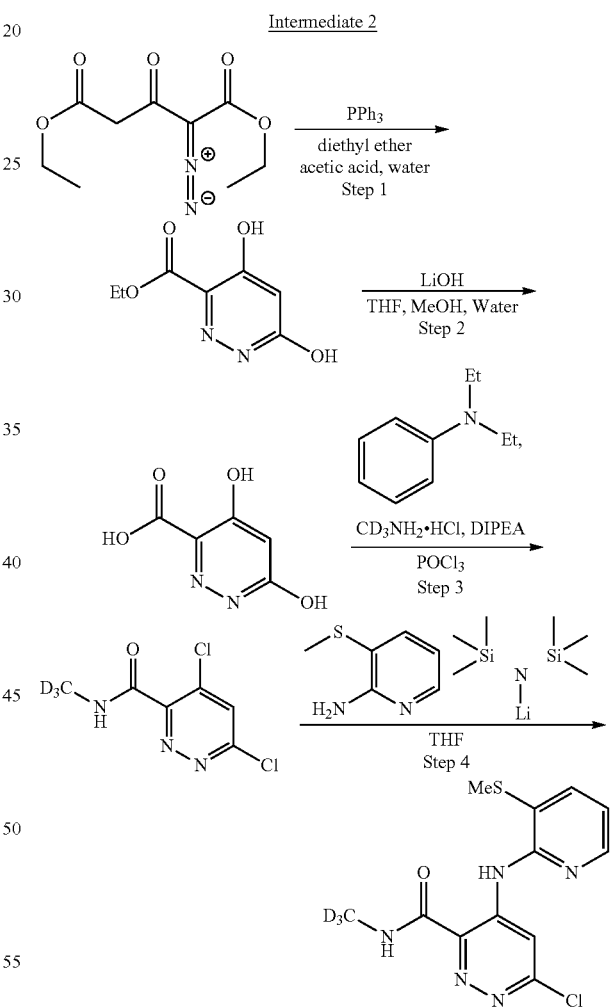

Intermediate 2

Step 1

Diethyl 2-diazo-3-oxopentanedioate (180 g, 789 mmol) was dissolved in diethyl ether (1800 mL), triphenylphosphine (207 g, 789 mmol) was added, and stirring continued overnight. Diethyl ether was removed under reduced pressure and the thick orange mass was dissolved in acetic acid (180 mL) and water (1800 mL). The clear solution was heated to 110° C. that was maintained for 3 hrs. The starting material was consumed. Acetic acid was removed under reduced pressure. The obtained thick mass was kept for one day in a cold room at about 0° C. for crystallization. DCM was added and the slurry was stirred and filtered. The filter cake was washed with DCM, and collected as the desired product, ethyl 4,6-dihydroxypyridazine-3-carboxylate (80 g, 434 mmol, 55.1% yield).

MS (M+1) m/z: 185.1 (MH$^+$). LC retention time 0.51 min [A].

$^1$H NMR (400 MHz, CHLOROFORM-d) δ 6.45-6.22 (m, 1H), 4.65-4.40 (m, 2H), 1.60-1.40 (m, 3H).

Step 2

In a 5000 ml rb flask, ethyl 4,6-dihydroxypyridazine-3-carboxylate (200 g, 1086 mmol) was dissolved in THF (2000 mL), methanol (1000 mL) and water (800 mL). LiOH (137 g, 3258 mmol) was added slowly at rt and stirred at rt for 3-4 hr. The starting material was gone. The solvent was removed at 50° C. under reduced pressure to afford a yellow solid. The solid was acidified with aqueous HCl solution (400 ml) (1:1 ratio) at 0° C. and stirred at rt for 30-40 minutes. The solid was filtered and washed with water. It was then dried under vacuum for 1-2 hr. This solid was taken into 300 ml of methanol:DCM (2:8) and stirred at rt for 20-25 minutes. The mixture was filtered and the solid was washed with methanol and dried under vacuum for 1 hr. The desired product was obtained as a yellow solid, 4,6-dihydroxypyridazine-3-carboxylic acid (153 g, 951 mmol, 88% yield).

MS (M+1) m/z: 156.9 (MH$^+$). LC retention time 0.31 min [A].

$^1$H NMR (400 MHz, deuterium oxide) δ 6.00-5.34 (m, 1H), 4.75 (s, 7H)

Step 3

A suspension of 4,6-dihydroxypyridazine-3-carboxylic acid, HCl (15 g, 78 mmol) and N,N-diethylaniline (12.39 ml, 78 mmol) in POCl$_3$ (200 ml) was stirred at 110° C. under a drying tube for 1 h. The reaction was completed after 1 h. POCl$_3$ was removed under vacuum and co-evaporated 3× with DCE. The crude intermediate, acid chloride was dissolved in 200 mL of THF. D3-methylamine HCl salt (2.75 g, 38.9 mmol) was added as a solid. The reaction was cooled to 0° C. DIPEA 2×(13.61 ml, 78 mmol) was added. The ice bath was removed and the reaction was stirred at rt. After 45 min, the reaction was complete. THF was removed under vacuum. The crude product was suspended in DCM, then evaporated onto Celite. This solid material was eluted with 0-100% EtOAc in hexanes through a 330 g silica gel column. The reaction produced 4,6-dichloro-N-[D3]-methylpyridazine-3-carboxamide (6.1 g, 29.2 mmol, 74.9% yield).

MS (M+1) m/z: 209.1 (MH$^+$). LC retention time 0.64 min [B].

$^{13}$C NMR (101 MHz, Chloroform-d) δ161.7, 158.43-156.22 (m, 1C), 149.8, 139.8, 130.7, 26.5

Step 4

To a solution of 4,6-dichloro-N-trideuteromethylpyridazine-3-carboxamide and 3-(methylthio)pyridin-2-amine (0.205 g, 1.464 mmol) in THF (10 mL) at rt was added lithium bis(trimethylsilyl)amide in THF (3.59 mL, 3.59 mmol) over 5 min. The resulting mixture was stirred at rt for 1 h. The reaction was quenched with water (5 mL). The mixture was adjusted with 1N HCl solution to pH 9-10, and further diluted with water (80 mL). The precipitating product, 6-chloro-N-trideuteromethyl-4-((3-(methylthio)pyridin-2-yl)amino)pyridazine-3-carboxamide (0.297 g, 0.950 mmol, 66.2% yield, Intermediate 2), was collected as a pale solid by suction filtration and dried at 50° C. under vacuum.

MS (M+1) m/z: 313.1 (MH$^+$). LC retention time 0.90 min [A].

Intermediate 3

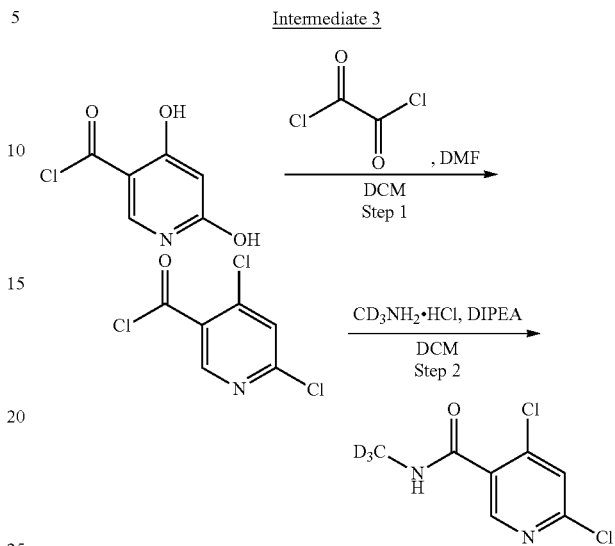

Step 1

To a heterogeneous, white solution of 4,6-dichloronicotinic acid (24.00 g, 125 mmol) in dichloromethane (250 mL) under nitrogen at 0° C. was added N,N-dimethylformamide (1 mL, 12.91 mmol). Oxalyl dichloride (14 mL, 162 mmol) was then added over 12 min. After 15 min, the ice-water bath was removed and the reaction was stirred to rt. After 1 h, N,N-dimethylformamide (1 mL, 12.91 mmol) was added to the still heterogeneous, white solution. After a total of 2.5 h the reaction showed >95% conversion to desired product. After another 30 min the reaction was concentrated in vacuo. DCM (100 mL) was added, and the solution was concentrated in vacuo. Another portion of DCM (100 mL) was added, and the solution was concentrated in vacuo to give the crude product which was used in the next step. The sample was quenched with ethanol. The mass detected is

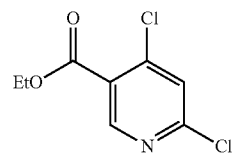 [SMILES: CCOC(=O)c1cnc(Cl)cc1Cl]

MS (M+1) m/z: 220.08 (MH$^+$). LC retention time 0.95 min [B].

Step 2

To a solution of 4,6-dichloronicotinoyl chloride (26.3 g, 125 mmol) and methan-d3-amine, HCl salt (11.46 g, 163 mmol) in DCM (250 mL) under nitrogen at 0° C. was syringed DIPEA (65.5 mL, 375 mmol). After 20 min, the ice-water bath was removed, and the reaction was stirred to rt. The reaction was stirred overnight and completed. The reaction mixture was washed with 0.5N aqueous HCl (50 mL). The layers were separated, and the aqueous layer was extracted with DCM (2×150 mL). The organic layers were combined, dried over Na$_2$SO$_4$, filtered, and concentrated in vacuo. The reaction mixture containing the product was purified with silica gel chromatography (1.5 kg silica Gold column) eluting with hexane and ethyl acetate. Product was collected at 60% ethyl acetate. 22.83 g of a slightly yellow solid was obtained, which was triturated with EtOAc (40 mL) and rinsed with EtOAc (20 mL) to give 4,6-dichloro-N-(methyl-d3)nicotinamide (21.93 g, 105 mmol, 84% yield) as a white solid.

MS (M+1) m/z: 208.1 (MH+). LC retention time 0.58 min [B].

$^1$H NMR (400 MHz, CHLOROFORM-d) δ 8.71-8.63 (m, 1H), 7.47-7.40 (m, 1H), 6.35-6.08 (m, 1H).

Example 1

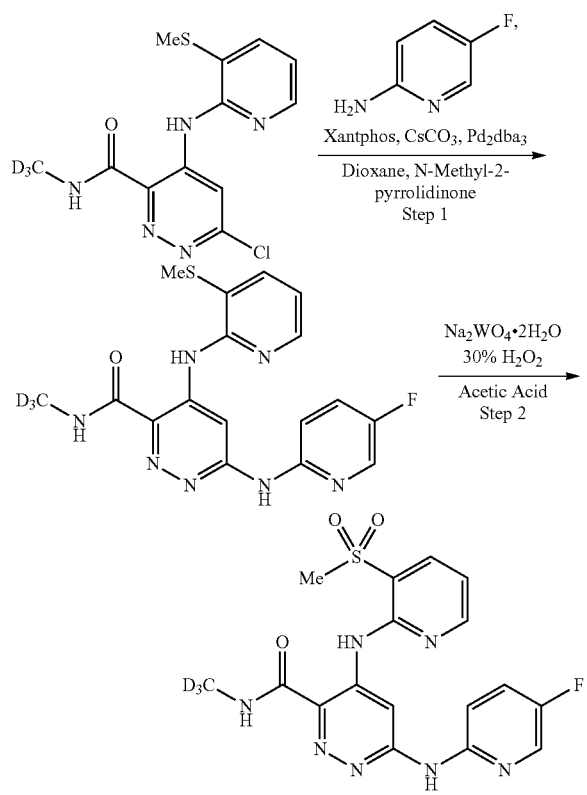

Step 1

A solution of Intermediate 2 (0.1028 g, 0.329 mmol, 6-chloro-N-trideuteromethyl-4-((3-(methylthio)pyridin-2-yl)amino)pyridazine-3-carboxamide), 5-fluoropyridin-2-amine (0.0845 g, 0.754 mmol), Xantphos (0.0345 g, 0.060 mmol), cesium carbonate (0.2481 g, 0.761 mmol) and Pd$_2$dba$_3$ (0.0483 g, 0.053 mmol) in dioxane (5 mL) and N-methyl-2-pyrrolidinone (1 mL) was microwaved at 150° C. for 1 h. The completed reaction mixture was diluted with ethyl acetate (10 mL) and filtered through Celite. The filtrate was concentrated in vacuo. DMSO (1 mL) and water (20 mL), followed by saturated NaHCO$_3$, were added to the residue. The precipitate was collected, filtered and washed with water to give crude product as an orange solid. The crude product was purified by flash chromatography using an ISCO 4 g column eluting with 0-5% MeOH/DCM (4 cv, 0%; 40 cv, 0-5%). Appropriate fractions (2-3% elution) were collected and concentrated in vacuo to give product, 6-((5-fluoropyridin-2-yl)amino)-N-(methyl-d3)-4-((3-(methylthio)pyridin-2-yl)amino)pyridazine-3-carboxamide, (0.035 g, 0.078 mmol, 23.85% yield) as a light yellow solid.

MS (M+1) m/z: 389.2 (MH+). LC retention time 0.94 min [B].

Step 2

To a homogeneous, yellow solution of reactant, 6-((5-fluoropyridin-2-yl)amino)-N-(methyl-d3)-4-((3-(methylthio)pyridin-2-yl)amino)pyridazine-3-carboxamide (0.035 g, 0.090 mmol), in acetic acid (0.3 mL) was added sodium tungstate dihydrate (0.0311 g, 0.094 mmol) to give a slurry. 30% hydrogen peroxide (0.2 mL, 1.958 mmol) was added which led to homogeneity. After 1.5 hr, water (2 mL) was added to the reaction which was extracted with ethyl acetate (3×15 mL). The organic layers were combined and washed with sat. aq. sodium bisulfite (5 mL) and water (5 mL) successively, dried over Na$_2$SO$_4$, filtered, and the filtrate was concentrated in vacuo. The residue was diluted with DMSO (0.5 mL) and MeOH (1.5 mL) and subjected to autoprep HPLC. The appropriate fractions were collected; NaHCO$_3$ (solid) was added, and the fractions were concentrated in vacuo not to dryness. The reaction mixture was extracted with DCM (3×), the organic layers were combined, dried over Na$_2$SO$_4$, filtered and concentrated in vacuo to give the product, 6-((5-fluoropyridin-2-yl)amino)-N-(methyl-d3)-4-((3-(methylsulfonyl)pyridin-2-yl)amino)pyridazine-3-carboxamide (0.00435 g, 10.35 μmol, 11.48% yield).

MS (M+1) m/z: 421.1 (MH+). LC retention time 0.61 min [B].

$^1$H NMR (400 MHz, DMSO-d$_6$) δ 12.26-11.92 (m, 1H), 10.54-10.32 (m, 1H), 9.67-9.32 (m, 1H), 9.26-9.05 (m, 1H), 8.87-8.58 (m, 1H), 8.42-8.19 (m, 2H), 7.88-7.64 (m, 2H), 7.47-7.15 (m, 1H).

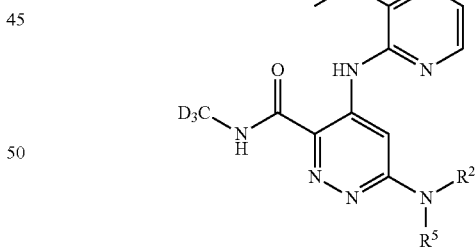

The following Examples were prepared in a similar manner to the preparation of Example 1.

TABLE 1

| Example No. | NR$^2$R$^5$ | MW | m/z [M + H]+ | Rt (min) [Method] |
|---|---|---|---|---|
| 2 | ![structure] | 432.47 | 433.2 | 0.61 [B] |

TABLE 1-continued

| Example No. | NR²R⁵ | MW | m/z [M + H]⁺ | Rt (min) [Method] |
|---|---|---|---|---|
| 3 | 4-methylpyridin-2-ylamino | 416.47 | 417.2 | 0.59 [B] |
| 4 | 4-fluoropyridin-2-ylamino | 420.44 | 421.1 | 0.60 [B] |
| 5 | 6-fluoropyridin-2-ylamino | 420.44 | 421.2 | 0.66 [B] |
| 6 | 5-fluoro-4-methylpyridin-2-ylamino | 434.46 | 435.2 | 0.65 [B] |
| 7 | 6-methoxypyridazin-3-ylamino | 433.46 | 434.1 | 0.59 [A] |
| 8 | propionamido | 381.43 | 382.1 | 0.64 [A] |
| 9 | cyclobutanecarboxamido | 407.46 | 408.1 | 0.73 [A] |
| 10 | 5-methylpyridin-2-ylamino | 416.47 | 417.2 | 0.60 [B] |
| 12 | 5-cyano-1-methyl-1H-pyrazol-3-ylamino | 430.46 | 431.1 | 0.68 [A] |
| 13 | 6-(2-hydroxypropan-2-yl)pyridin-3-ylamino | 460.53 | 461.3 | 0.58 [B] |

TABLE 1-continued
| Example No. | NR²R⁵ | MW | m/z [M + H]⁺ | Rt (min) [Method] |
|---|---|---|---|---|
| 14 | 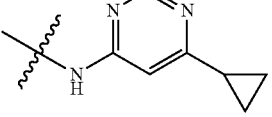 | 443.5 | 444.1 | 0.60 [A] |
| 15 | 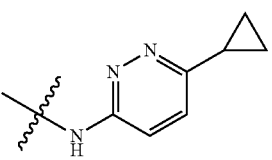 [SMILES: *Nc1ccc(C2CC2)nn1] | 443.5 | 444.1 | 0.59 [A] |
| 16 | 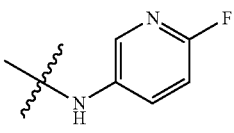 [SMILES: *Nc1ccc(F)nc1] | 420.44 | 421.0 | 0.64 [A] |
| 17 | 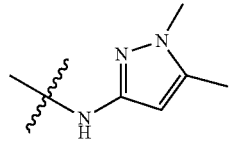 [SMILES: *Nc1cc(C)n(C)n1] | 419.48 | 420.2 | 0.60 [B] |
| 18 | 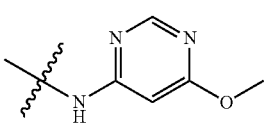 [SMILES: *Nc1cc(OC)ncn1] | 433.46 | 434.1 | 0.61 [A] |
| 19 | 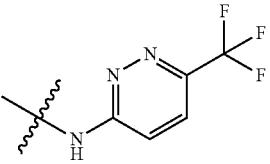 [SMILES: *Nc1ccc(C(F)(F)F)nn1] | 471.43 | 472.1 | 0.72 [A] |
| 20 | 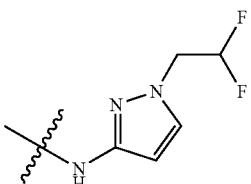 | 455.46 | 456.0 | 0.66 [A] |
| 21 | 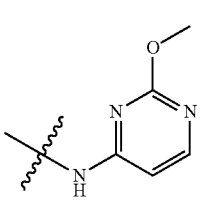 [SMILES: *Nc1ccnc(OC)n1] | 433.46 | 434.1 | 0.58 [B] |
| 22 | 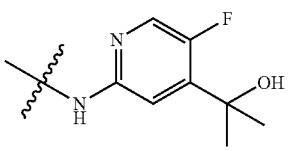 [SMILES: *Nc1cc(C(C)(C)O)c(F)cn1] | 478.52 | 479.1 | 0.66 [A] |
| 23 | 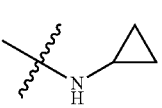 | 365.43 | 366.2 | 1.3 [QC-ACN-AA-XB] |

TABLE 1-continued
| Example No. | NR²R⁵ | MW | m/z [M + H]⁺ | Rt (min) [Method] |
|---|---|---|---|---|
| 24 | 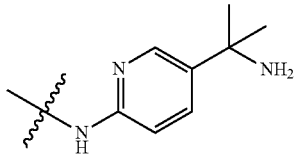 [SMILES: *Nc1ccc(C(C)(C)N)cn1] | 459.54 | 460.2 | 1 [QC-ACN-TFA-XB] |
| 25 | 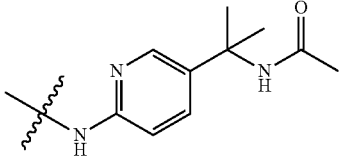 [SMILES: *Nc1ccc(C(C)(C)NC(C)=O)cn1] | 501.58 | 502.1 | 1.3 [QC-ACN-AA-XB] |
| 26 | 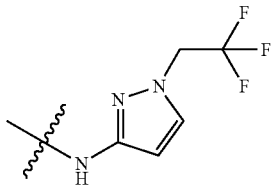 [SMILES: *Nc1ccn(CC(F)(F)F)n1] | 473.45 | 474.0 | 0.65 [A] |
| 27 | 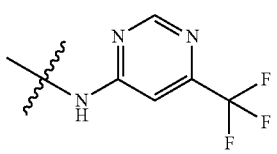 [SMILES: *Nc1cc(C(F)(F)F)ncn1] | 471.43 | 472.1 | 0.78 [B] |
| 28 | 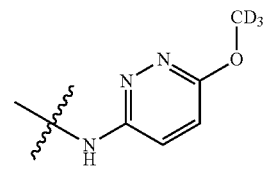 [SMILES: *Nc1ccc(OC([2H])([2H])[2H])nn1] | 436.48 | 437.0 | 0.57 [A] |
| 29 | 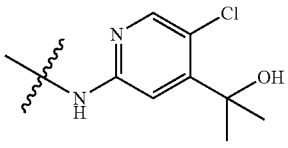 | 494.97 | 495.1 | 0.69 [B] |
| 30 | 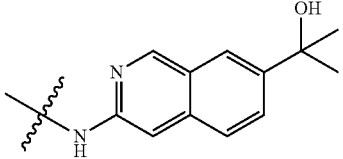 [SMILES: *Nc1cc2ccc(C(C)(C)O)cc2cn1] | 510.59 | 510.9 | 0.65 [A] |
| 31 | 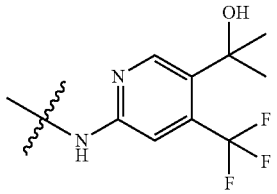 [SMILES: *Nc1cc(C(F)(F)F)c(C(C)(C)O)cn1] | 528.53 | 528.8 | 0.69 [A] |
| 32 | 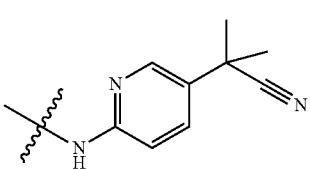 [SMILES: *Nc1ccc(C(C)(C)C#N)cn1] | 653.16 | 653.1 | 1.9 [QC-ACN-AA-XB] |

TABLE 1-continued

| Example No. | NR²R⁵ | MW | m/z [M + H]⁺ | Rt (min) [Method] |
|---|---|---|---|---|
| 33 | (pyridine with cyclopropyl-CN substituent, NH linker) | 467.52 | 468.2 | 1.4 [QC-ACN-AA-XB] |
| 34 | (pyrimidine with N(CH₃)₂, NH linker) | 446.5 | 446.9 | 0.58 [A] |
| 35 | (pyrimidine with azetidinyl, NH linker) | 458.52 | 458.9 | 0.58 [A] |
| 36 | (pyridine with C(CH₃)₂OH and OMe, NH linker) | 490.55 | 490.9 | 0.60 [A] |
| 37 | (pyrazine with cyclopropyl, NH linker) | 443.5 | 444.0 | 0.65 [A] |
| 38 | (pyridazine with N(CH₃)₂, NH linker) | 446.5 | 446.9 | 0.54 [A] |
| 39 | (pyrazine with ethyl, NH linker) | 431.49 | 431.9 | 0.63 [A] |
| 40 | (pyrimidine with cyclopropyl, NH linker) | 443.5 | 444.0 | 0.56 [A] |
| 41 | (pyrimidine with CH₂OMe and cyclopropyl, NH linker) | 487.55 | 488 | 1.1 [QC-ACN-TFA-XB] |

TABLE 1-continued
| Example No. | NR²R⁵ | MW | m/z [M + H]⁺ | Rt (min) [Method] |
|---|---|---|---|---|
| 42 | 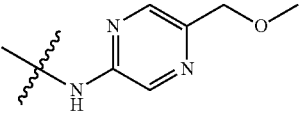 [SMILES: *Nc1cnc(COC)cn1] | 447.49 | 447.9 | 0.58 [A] |
| 43 | 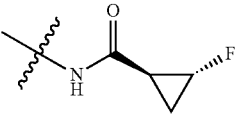 [SMILES: *NC(=O)[C@@H]1C[C@H]1F] | 411.43 | 411.9 | 0.67 [A] |
| 44 | 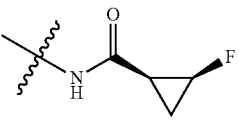 [SMILES: *NC(=O)[C@@H]1C[C@@H]1F] | 411.43 | 412.0 | 0.63 [A] |
| 45 | 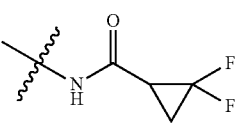 [SMILES: *NC(=O)C1CC1(F)F] | 429.42 | 430.0 | 0.70 [A] |
| 46 | 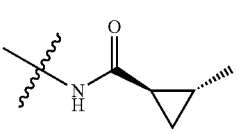 [SMILES: *NC(=O)[C@@H]1C[C@H]1C] | 407.46 | 408.08 | 0.69 [A] |
| 47 | 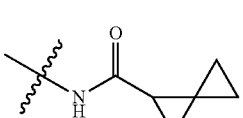 | 419.47 | 420.0 | 0.71 [A] |
| 48 | 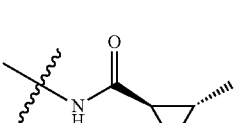 | 407.46 | 408.08 | 0.69 [A] |
| 49 | 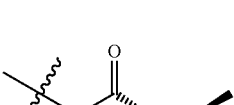 | 407.46 | 408.08 | 0.69 [A] |
| 50 | 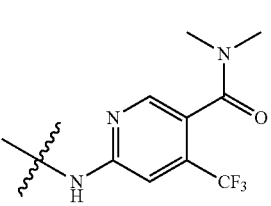 [SMILES: *Nc1cc(C(F)(F)F)c(C(=O)N(C)C)cn1] | 541.52 | 541.8 | 0.65 [A] |
| 51 | 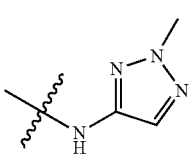 [SMILES: *Nc1cnn(C)n1] | 406.44 | 406.8 | 0.61 [A] |

TABLE 1-continued
| Example No. | NR²R⁵ | MW | m/z [M + H]⁺ | Rt (min) [Method] |
|---|---|---|---|---|
| 52 | 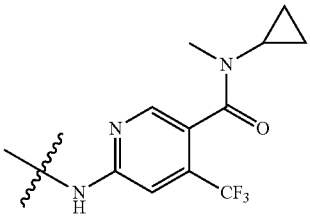 [SMILES: *Nc1cc(C(F)(F)F)c(C(=O)N(C)C2CC2)cn1] | 567.56 | 567.7 | 0.74 [A] |
| 53 | 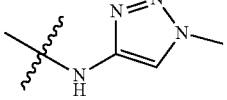 | 406.44 | 406.8 | 0.58 [A] |
| 56 | 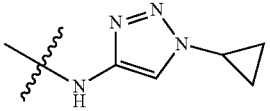 [SMILES: *Nc1cn(C2CC2)nn1] | 432.48 | 433.3 | 0.68 [B] |
| 57 | 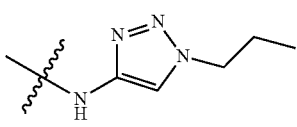 [SMILES: *Nc1cn(CCC)nn1] | 434.49 | 434.8 | 0.64 [A] |
| 58 | 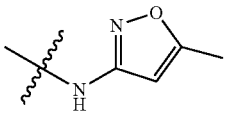 [SMILES: *Nc1cc(C)on1] | 406.44 | 406.8 | 0.67 [A] |
| 59 | 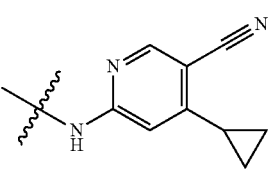 [SMILES: *Nc1cc(C2CC2)c(C#N)cn1] | 467.52 | 468.2 | 0.75 [B] |
| 60 | 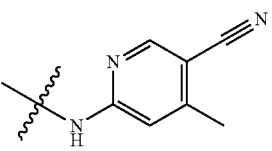 [SMILES: *Nc1cc(C)c(C#N)cn1] | 441.48 | 441.8 | 0.64 [A] |
| 61 | 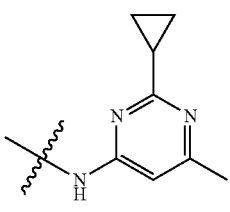 [SMILES: *Nc1cc(C)nc(C2CC2)n1] | 457.53 | 457.8 | 0.58 [A] |
| 62 | 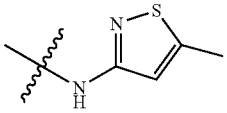 [SMILES: *Nc1cc(C)sn1] | 422.5 | 422.8 | 0.60 [A] |
| 63 | 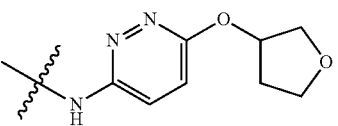 [SMILES: *Nc1ccc(OC2CCOC2)nn1] | 489.53 | 489.9 | 0.58 [A] |

TABLE 1-continued

| Example No. | NR²R⁵ | MW | m/z [M + H]⁺ | Rt (min) [Method] |
|---|---|---|---|---|
| 64 | 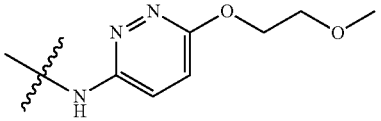 [SMILES: *Nc1ccc(OCCOC)nn1] | 477.51 | 478.2 | 0.59 [A] |
| 65 | 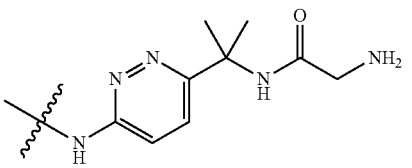 [SMILES: *Nc1ccc(C(C)(C)NC(=O)CN)nn1] | 516.6 | 516.9 | 0.8 [QC-ACN-TFA-XB] |
| 66 | 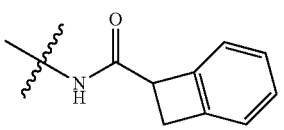 [SMILES: *NC(=O)C1Cc2ccccc21] | 455.51 | 456.2 | 0.78 [A] |
| 67 | 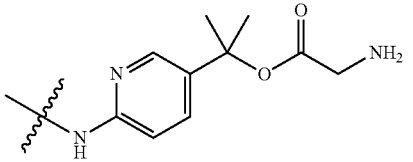 [SMILES: *Nc1ccc(C(C)(C)OC(=O)CN)cn1] | 517.58 | 518.3 | 0.8 [QC-ACN-TFA-XB] |
| 68 | 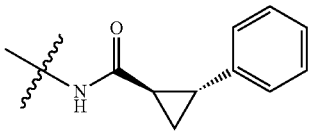 [SMILES: *NC(=O)[C@@H]1C[C@H]1c1ccccc1] | 437.53 | 438.08 | 0.91 [A] |

Example 69

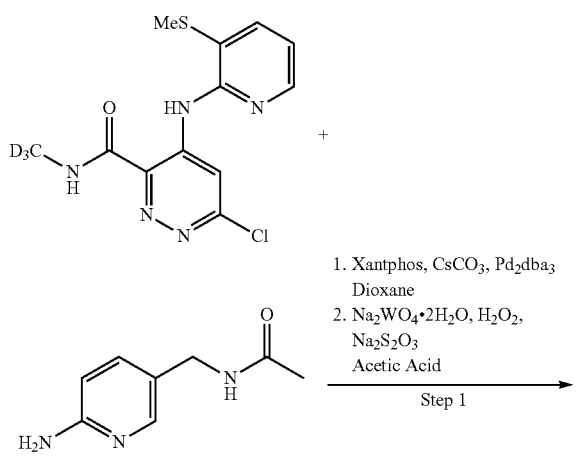

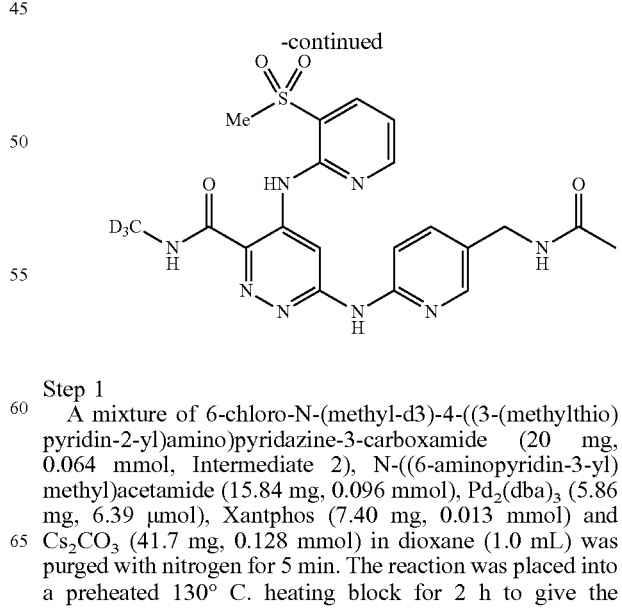

Step 1

A mixture of 6-chloro-N-(methyl-d3)-4-((3-(methylthio)pyridin-2-yl)amino)pyridazine-3-carboxamide (20 mg, 0.064 mmol, Intermediate 2), N-((6-aminopyridin-3-yl)methyl)acetamide (15.84 mg, 0.096 mmol), Pd₂(dba)₃ (5.86 mg, 6.39 µmol), Xantphos (7.40 mg, 0.013 mmol) and Cs₂CO₃ (41.7 mg, 0.128 mmol) in dioxane (1.0 mL) was purged with nitrogen for 5 min. The reaction was placed into a preheated 130° C. heating block for 2 h to give the intermediate sulfide (M+H=442). The solvent was concentrated and the material was re-dissolved in AcOH (2 mL). To the solution was added sodium tungstate dihydrate (6.33 mg, 0.019 mmol) and hydrogen peroxide (98 µl, 3.20 mmol) and the mixture was stirred at rt for 1 h. Sodium thiosulfate (505 mg, 3.20 mmol) was added and the reaction mixture was stirred for 10 min. The solvent was removed to give 6-((5-(acetamidomethyl)pyridin-2-yl)amino)-N-(methyl-d3)-4-((3-(methylsulfonyl)pyridin-2-yl)amino)pyridazine-3-carboxamide (3 mg, 5.7 µmol, 8.92% yield, 90% purity).

MS (M+1) m/z: 421.1 (MH+). LC retention time 0.61 min [B].

$^1$H NMR (500 MHz, DMSO-d$_6$) δ 12.14-12.02 (m, 1H), 10.36-10.25 (m, 1H), 9.57-9.43 (m, 1H), 9.18-9.05 (m, 1H), 8.69-8.59 (m, 1H), 8.40-8.33 (m, 1H), 8.32-8.25 (m, 1H), 8.22-8.14 (m, 1H), 7.67-7.59 (m, 2H), 7.38-7.28 (m, 1H), 4.21 (br s, 3H), 3.41-3.33 (m, 2H), 1.89-1.83 (m, 3H).

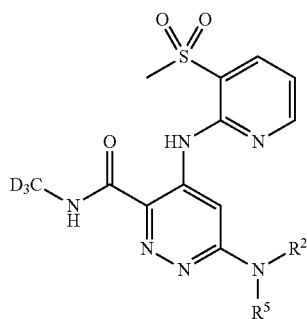

The following Examples were prepared in a similar manner to the preparation of the product of Example 69.

TABLE 2

| Example No. | NR²R⁵ | MW | m/z [M + H]⁺ | Rt (min) [Method] |
|---|---|---|---|---|
| 70 | | 501.58 | 502.3 | 0.9 [QC-ACN-TFA-XB] |
| 71 | | 376.46 | 377.2 | 0.8 [QC-ACN-TFA-XB] |
| 72 | | 501.62 | 502.3 | 1.1 [QC-ACN-AA-XB] |
| 73 | | 487.6 | 487.9 | 1.4 [QC-ACN-AA-XB] |
| 74 | | 517.58 | 518.2 | 1 [QC-ACN-TFA-XB] |
| 75 | | 529.59 | 530.37 | 0.98 [QC-ACN-TFA-XB] |
| 76 | | 527.62 | 528.2 | 1.3 [QC-ACN-AA-XB] |

TABLE 2-continued

| Example No. | NR²R⁵ | MW | m/z [M + H]⁺ | Rt (min) [Method] |
|---|---|---|---|---|
| 77 | | 490.55 | 491 | 1.3 [QC-ACN-AA-XB] |
| 78 | | 545.63 | 546.1 | 1.5 [QC-ACN-TFA-XB] |
| 79 | | 531.61 | 532 | 1.5 [QC-ACN-AA-XB] |
| 80 | | 433.46 | 434.1 | 1.3 [QC-ACN-AA-XB] |
| 81 | | 487.55 | 488.17 | 1.12 [QC-ACN-TFA-XB] |
| 82 | | 416.47 | 417.3 | 1.5 [QC-ACN-AA-XB] |
| 83 | | 447.49 | 448.1 | 1.3 [QC-ACN-AA-XB] |
| 84 | | 447.49 | 448.2 | 1.1 [QC-ACN-AA-XB] |
| 85 | | 417.46 | 418.2 | 0.8 [QC-ACN-TFA-XB] |
| 86 | | 421.43 | 422.3 | 0.9 [QC-ACN-TFA-XB] |

TABLE 2-continued
| Example No. | NR²R⁵ | MW | m/z [M + H]⁺ | Rt (min) [Method] |
|---|---|---|---|---|
| 87 | 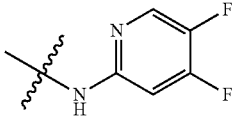 | 438.43 | 439 | 1.4 [QC-ACN-AA-XB] |
| 88 | 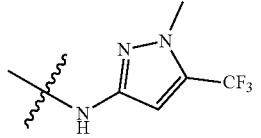 [SMILES: *Nc1cc(C(F)(F)F)n(C)n1] | 473.45 | 474.2 | 1.5 [QC-ACN-AA-XB) |
| 89 | 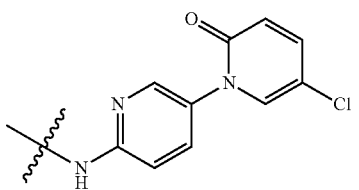 [SMILES: *Nc1ccc(-n2cc(Cl)ccc2=O)cn1] | 529.97 | 530 | 1.4 [QC-ACN-AA-XB] |
| 90 | 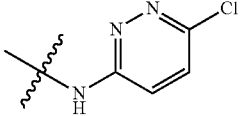 [SMILES: *Nc1ccc(Cl)nn1] | 437.88 | 438 | 1.3 [QC-ACN-AA-XB] |
| 91 | 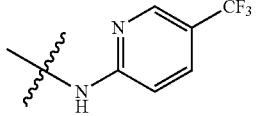 | 470.45 | 471.18 | 1.73 [QC-ACN-AA-XB] |
| 92 | 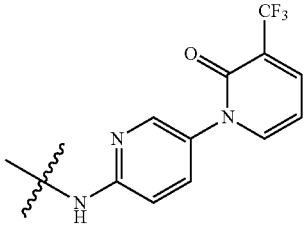 [SMILES: *Nc1ccc(-n2cccc(C(F)(F)F)c2=O)cn1] | 563.53 | 563.9 | 1.6 [QC-ACN-TFA-XB] |
| 93 | 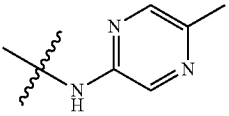 [SMILES: *Nc1cnc(C)cn1] | 417.46 | 417.9 | 1 [QC-ACN-TFA-XB] |
| 94 | 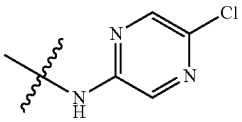 [SMILES: *Nc1cnc(Cl)cn1] | 555.53 | 556.2 | |
| 95 | 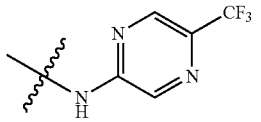 | 471.43 | 472.2 | 1.6 [QC-ACN-AA-XB] |
| 96 | 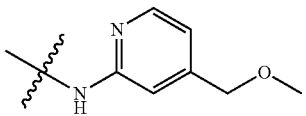 [SMILES: *Nc1cc(COC)ccn1] | 446.5 | 447.1 | 1.1 [QC-ACN-TFA-XB] |

TABLE 2-continued

| Example No. | NR²R⁵ | MW | m/z [M + H]⁺ | Rt (min) [Method] |
|---|---|---|---|---|
| 97 | | 501.54 | 502.2 | 0.8 [QC-ACN-TFA-XB] |
| 98 | | 431.49 | 432.1 | 0.7 [QC-ACN-TFA-XB] |
| 99 | | 471.55 | 472.1 | 1.6 [QC-ACN-AA-XB] |
| 100 | | 515.61 | 516.1 | 1.5 [QC-ACN-AA-XB] |
| 101 | | 461.52 | 462.2 | 1.2 [QC-ACN-AA-XB] |
| 102 | | 478.55 | 479.2 | 1.8 [QC-ACN-AA-XB] |
| 103 | | 501.58 | 502 | 1.4 [QC-ACN-AA-XB] |
| 104 | | 515.51 | 516.1 | 1.5 [QC-ACN-AA-XB] |

TABLE 2-continued
| Example No. | NR²R⁵ | MW | m/z [M + H]⁺ | Rt (min) [Method] |
|---|---|---|---|---|
| 105 | 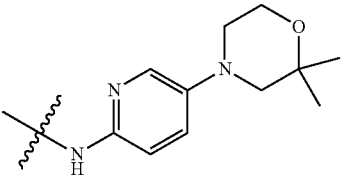 [SMILES: *Nc1ccc(N2CCOC(C)(C)C2)cn1] | 515.61 | 516.2 | 1.1 [QC-ACN-TFA-XB] |
| 106 | 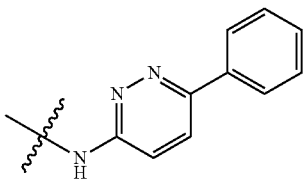 [SMILES: *Nc1ccc(-c2ccccc2)nn1] | 479.53 | 480.3 | 1.6 [QC-ACN-AA-XB] |
| 107 | 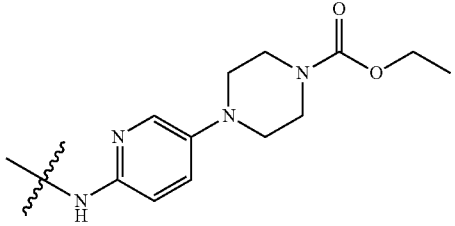 [SMILES: *Nc1ccc(N2CCN(C(=O)OCC)CC2)cn1] | 558.63 | 559 | 1.5 [QC-ACN-AA-XB] |
| 108 | 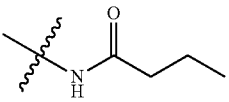 [SMILES: *NC(=O)CCC] | 395.45 | 396.2 | 1.3 [QC-ACN-AA-XB] |
| 109 | 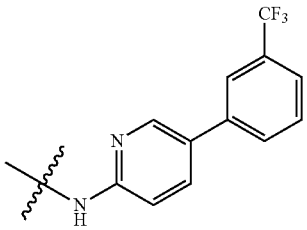 [SMILES: *Nc1ccc(-c2cccc(C(F)(F)F)c2)cn1] | 546.54 | 547.2 | 1.7 [QC-ACN-TFA-XB] |
| 110 | 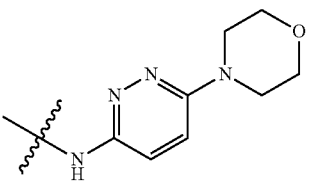 [SMILES: *Nc1ccc(N2CCOCC2)nn1] | 488.54 | 489.2 | 1.2 [QC-ACN-AA-XB) |
| 111 | 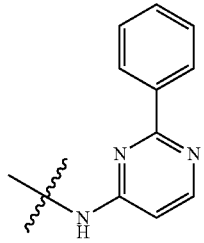 [SMILES: *Nc1ccnc(-c2ccccc2)n1] | 479.53 | 479.9 | 1.4 [QC-ACN-TFA-XB] |
| 112 | 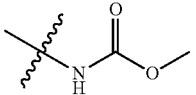 | 383.4 | 384.1 | 1 [QC-ACN-AA-XB] |

TABLE 2-continued
| Example No. | NR²R⁵ | MW | m/z [M + H]⁺ | Rt (min) [Method] |
|---|---|---|---|---|
| 113 | 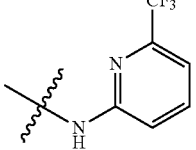 | 470.45 | 471.1 | 1.7 [QC-ACN-AA-XB] |
| 114 | 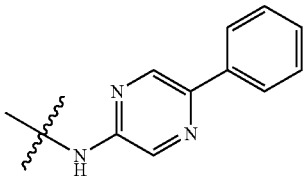 [SMILES: *Nc1cnc(-c2ccccc2)cn1] | 479.53 | 480.2 | 1.7 [QC-ACN-AA-XB] |
| 115 | 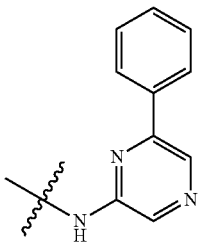 [SMILES: *Nc1cncc(-c2ccccc2)n1] | 479.53 | 480.1 | 1.6 [QC-ACN-AA-XB] |
| 116 | 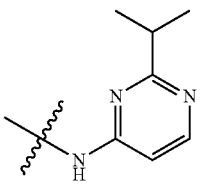 | 459.54 | 459.9 | 1.5 [QC-ACN-AA-XB] |
| 117 | 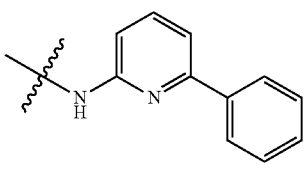 [SMILES: *Nc1cccc(-c2ccccc2)n1] | 478.55 | 479 | 1.5 [QC-ACN-TFA-XB] |
| 118 | 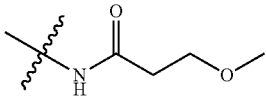 [SMILES: *NC(=O)CCOC] | 411.45 | 412.13 | 1.07 [QC-ACN-AA-XB] |
| 119 | 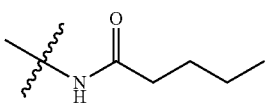 [SMILES: *NC(=O)CCCC] | 409.48 | 410.2 | 1.5 [QC-ACN-AA-XB] |
| 120 | 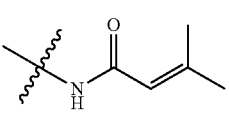 [SMILES: *NC(=O)C=C(C)C] | 407.46 | 408.2 | 1.3 [QC-ACN-AA-XB] |
| 121 | 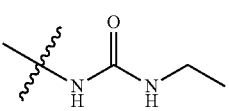 [SMILES: *NC(=O)NCC] | 396.44 | 397.2 | 0.8 [QC-ACN-TFA-XB] |
| 122 | 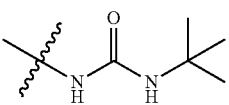 [SMILES: *NC(=O)NC(C)(C)C] | 424.49 | 425.1 | 1.4 [QC-ACN-AA-XB] |

TABLE 2-continued

| Example No. | NR²R⁵ | MW | m/z [M + H]⁺ | Rt (min) [Method] |
|---|---|---|---|---|
| 123 | | 449.5 | 449.9 | 1 [QC-ACN-TFA-XB] |
| 124 | | 449.5 | 450 | 1.1 [QC-ACN-TFA-XB] |
| 125 | | 425.45 | 426.1 | 1.19 [QC-ACN-AA-XB] |
| 126 | | 425.45 | 426.1 | 1.31 [QC-ACN-AA-XB] |
| 127 | | 471.43 | 472.1 | 1.4 [QC-ACN-TFA-XB] |
| 128 | | 447.53 | 448.1 | 1.7 [QC-ACN-AA-XB] |
| 129 | | 409.48 | 410.2 | 1.3 [QC-ACN-TFA-XB] |
| 130 | | 445.52 | 446.3 | 1.4 [QC-ACN-AA-XB] |
| 131 | | 395.45 | 396.1 | 1.2 [QC-ACN-AA-XB] |
| 132 | | 397.42 | 398 | 1.2 [QC-ACN-TFA-XB] |
| 133 | | 473.52 | 474 | 1.5 [QC-ACN-TFA-XB] |

TABLE 2-continued

| Example No. | NR²R⁵ | MW | m/z [M + H]⁺ | Rt (min) [Method] |
|---|---|---|---|---|
| 134 | isopropyl carbamate | 411.45 | 412.2 | 1.2 [QC-ACN-TFA-XB] |
| 135 | acetamide | 370.42 | 371.2 | 1.1 [QC-ACN-TFA-XB] |
| 136 | propyl carbamate | 411.45 | 412.3 | 1.4 [QC-ACN-TFA-XB] |
| 137 | propionamide | 383.44 | 384.2 | 1 [QC-ACN-TFA-XB] |
| 138 | 2-(trifluoromethyl)pyrimidin-4-ylamino | 471.43 | 472.3 | 1.4 [QC-ACN-AA-XB] |
| 139 | 3,3-dimethylbutanamide | 423.51 | 424.2 | 1.4 [QC-ACN-TFA-XB] |
| 140 | 5-(trifluoromethoxy)pyridin-2-ylamino | 486.44 | 487.3 | 1.68 [QC-ACN-AA-XB] |
| 141 | imidazo[1,2-b]pyridazin-3-ylamino | 442.47 | 443.2 | 1 [QC-ACN-TFA-XB] |
| 142 | 6-(dimethylphosphoryl)pyridin-2-ylamino | 478.48 | 479.1 | 1.1 [QC-ACN-AA-XB] |
| 143 | 1-methyl-3-amino-1H-pyrazole-5-carboxylic acid | 449.46 | 450.1 | 0.9 [QC-ACN-AA-XB] |
| 144 | 5-aminopyrazine-2-carboxylic acid | 447.44 | 448 | 1 [QC-ACN-TFA-XB] |

TABLE 2-continued

| Example No. | NR²R⁵ | MW | m/z [M + H]⁺ | Rt (min) [Method] |
|---|---|---|---|---|
| 145 | | 421.49 | 421.9 | 1.4 [QC-ACN-AA-XB] |
| 147 | | 523.02 | 523.4 | 1.7 [QC-ACN-AA-XB] |
| 148 | | 529.59 | 530.4 | 1.1 [QC-ACN-TFA-XB] |
| 149 | | 504.58 | 505.4 | 1.3 [QC-ACN-AA-XB] |
| 151 | | 478.52 | 479.1 | 1 [QC-ACN-TFA-XB] |
| 152 | | 442.51 | 442.9 | 1.6 [QC-ACN-AA-XB] |
| 153 | | 421.49 | 422.1 | 1.4 [QC-ACN-AA-XB] |
| 154 | | 446.5 | 447.1 | 1.2 [QC-ACN-AA-XB) |
| 155 | | 449.52 | 450.2 | 1.2 [QC-ACN-AA-XB] |
| 156 | | 449.52 | 450.2 | 1.4 [QC-ACN-AA-XB] |

TABLE 2-continued

| Example No. | NR²R⁵ | MW | m/z [M + H]⁺ | Rt (min) [Method] |
|---|---|---|---|---|
| 157 | | 474.55 | 475.3 | 1.1 [QC-ACN-TFA-XB] |
| 158 | | 476.53 | 477.2 | 1.04 [QC-ACN-TFA-XB] |

Example 159

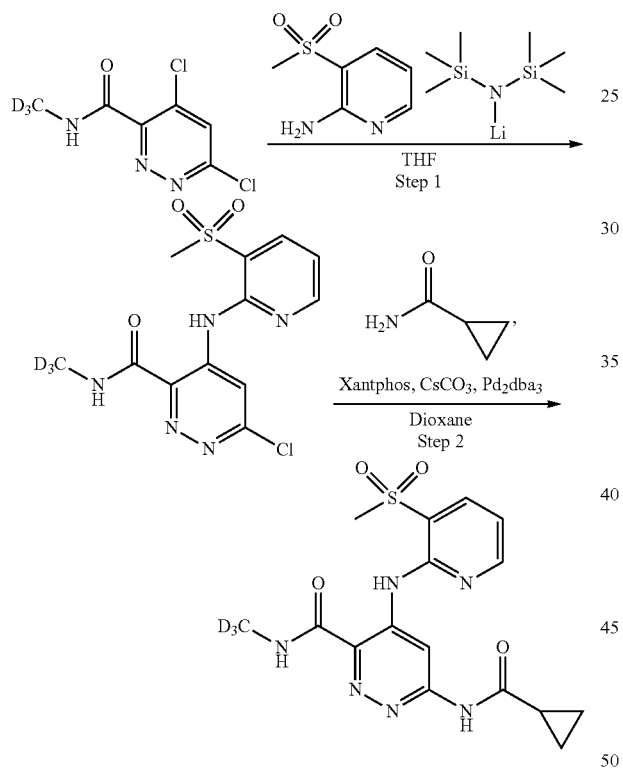

Step 1

Lithium bis(trimethylsilyl)amide (0.581 mL, 0.581 mmol, 1 M in THF) was quickly added to a solution of 3-(methylsulfonyl)pyridin-2-amine (0.05 g, 0.290 mmol) and 4,6-dichloro-N-trideuteromethylpyridazine-3-carboxamide (0.073 g, 0.348 mmol) in THF (5 mL) at room temperature. After complete addition, the reaction mixture was stirred at room temperature for thirty minutes. The reaction mixture was quenched with 1N HCl and MeOH and concentrated under vacuum. The product was chromatographed on silica gel using the ISCO and eluting with 0-10% MeOH/DCM. Fractions containing product were combined and concentrated under vacuum to provide 6-chloro-N-(methyl-d3)-4-((3-(methylsulfonyl)pyridin-2-yl)amino)pyridazine-3-carboxamide (40 mg, 0.116 mmol, 40% yield).

MS (M+1) m/z: 345.08 (MH⁺). LC retention time 0.71 min [A].

Step 2

A stirred mixture of 6-chloro-N-trideuteromethyl-4-((3-(methylsulfonyl)pyridin-2-yl)amino)pyridazine-3-carboxamide (0.025 g, 0.073 mmol), cyclopropane carboxamide (6.79 mg, 0.080 mmol), tris(dibenzylideneacetone)dipalladium(0) (0.664 mg, 0.725 μmol), 4,5-bis(diphenylphosphino)-9,9-dimethylxanthene (0.420 mg, 0.725 μmol) and cesium carbonate (0.071 g, 0.218 mmol) in 1,4-dioxane (2 mL) was heated in a sealed vessel at 130° C. for one hour. The reaction mixture was diluted with ethyl acetate (5 mL), filtered and the filtrate was concentrated. The residue was dissolved in 1 mL DMF and purified with prep HPLC. The desired fractions were collected and concentrated to give 6-(cyclopropanecarboxamido)-N-trideuteromethyl-4-((3-(methylsulfonyl)pyridin-2-yl)amino)pyridazine-3-carboxamide (4 mg, 10.17 μmol, 10.4% yield).

MS (M+1) m/z: 394.08 (MH⁺). LC retention time 0.64 min [A].

¹H NMR (500 MHz, DMSO-d₆) δ 9.61-9.36 (m, 1H), 9.31-9.08 (m, 1H), 8.80-8.53 (m, 1H), 8.37-8.07 (m, 1H), 7.52-7.20 (m, 1H), 2.19-2.04 (m, 1H), 0.94-0.73 (m, 4H).

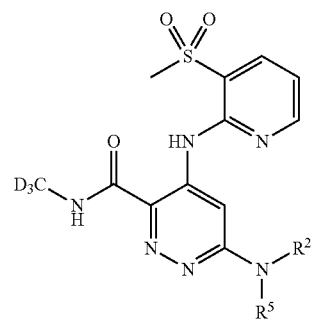

The following Examples were prepared in a similar manner to the product of Example 159.

TABLE 3

| Example No. | NR²R⁵ | MW | m/z [M + H]⁺ | Rt (min) [Method] |
|---|---|---|---|---|
| 160 | | 402.5 | 403.1 | 0.56 [A] |

TABLE 3-continued

| Example No. | NR²R⁵ | MW | m/z [M + H]⁺ | Rt (min) [Method] |
|---|---|---|---|---|
| 161 | 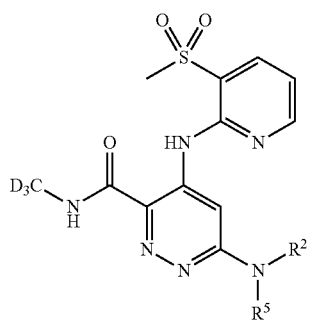 | 439.9 | 440.1 | 0.64 [A] |

Example 163

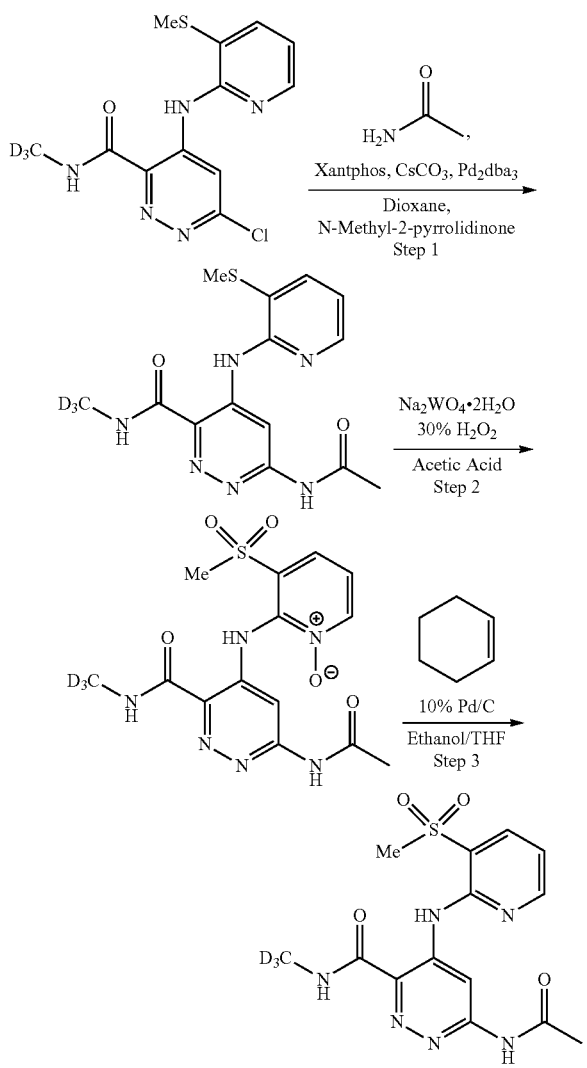

Step 1

A mixture of 6-chloro-N-trideuteromethyl-4-((3-(methylthio)pyridin-2-yl)amino)pyridazine-3-carboxamide (100 mg, 0.320 mmol, Intermediate 2), acetamide (41.5 mg, 0.703 mmol), tris(dibenzylideneacetone)dipalladium(0) (43.9 mg, 0.048 mmol), Xantphos (27.7 mg, 0.048 mmol), and cesium carbonate (229 mg, 0.703 mmol) in 1,4-dioxane (6 mL) was heated under microwave conditions at 150° C. for 1 h. The mixture was diluted with ethyl acetate (8 mL) and filtered through Celite. The filtrate was concentrated under vacuum. To the residue was added DMSO (5 mL), followed by water (55 mL) and saturated NaHCO₃ solution (3 mL). The insoluble material was collected by filtration, and further purified by ISCO (24 g silica gel, solid loading, 0-5% MeOH/dichloromethane) to provide the desired product, 6-acetamido-N-trideuteromethyl-4-((3-(methylthio)pyridin-2-yl)amino)pyridazine-3-carboxamide (21 mg, 0.063 mmol, 19.58% yield) as a white solid.

MS (M+1) m/z: 336.1 (MH⁺). LC retention time 0.67 min [B].

Step 2

To a solution of 6-acetamido-N-trideuteromethyl-4-((3-(methylthio)pyridin-2-yl)amino)pyridazine-3-carboxamide (21 mg, 0.063 mmol) in acetic acid (1.5 ml) was added sodium tungstate dihydrate (21.69 mg, 0.066 mmol), followed by 30% hydrogen peroxide (0.192 mL, 1.878 mmol). The solution was stirred at rt overnight. The starting material sulfide was consumed, but the sulfoxide was the predominant product. Additional sodium tungstate dihydrate (21.69 mg, 0.066 mmol) and 30% hydrogen peroxide (0.192 mL, 1.878 mmol) were added. The mixture was heated at 50° C. for 1 h. The product was over oxidized to produce N-oxide. The mixture was diluted with water (15 mL), basified with solid Na₂CO₃, and extracted with DCM (3×30 mL). The combined extraction was dried over anhydrous Na₂SO₄. The product, 2-((6-acetamido-3-(trideuteromethylcarbamoyl)pyridazin-4-yl)amino)-3-(methylsulfonyl)pyridine 1-oxide (12 mg, 0.031 mmol, 50.0% yield), was isolated as a white solid by prep HPLC.

MS (M+1) m/z: 384.08 (MH⁺). LC retention time 0.59 min [A].

Step 3

To a solution of 2-((6-acetamido-3-(trideuteromethylcarbamoyl)pyridazin-4-yl)amino)-3-(methylsulfonyl)pyridine 1-oxide (12 mg, 0.031 mmol) in THF (3 mL) and ethanol (1 mL) was added 10% Pd/C (24.98 mg, 0.023 mmol), followed by cyclohexene (0.101 mL, 1.002 mmol). The mixture was heated at 80° C. in a closed vial for 16 h. The solid phase was removed by filtration. The filtrate was concentrated under vacuum, and the residue was subjected to ISCO (12 g silica gel, solid loading, 0-5% MeOH/dichloromethane) to provide the desired product, 6-acetamido-N-trideuteromethyl-4-((3-(methylsulfonyl) pyridin-2-yl)amino)pyridazine-3-carboxamide (2.7 mg, 7.13 μmol, 22.78% yield), as a white solid.

MS (M+1) m/z: 368.08 (MH⁺). LC retention time 0.57 min [A].

¹H NMR (400 MHz, DMSO-d₆) δ 12.15-12.06 (m, 1H), 11.19-11.02 (m, 1H), 9.59-9.44 (m, 1H), 9.26-9.12 (m, 1H), 8.66-8.56 (m, 1H), 8.34-8.23 (m, 1H), 7.38-7.26 (m, 1H), 3.39-3.35 (s, 3H), 2.19-2.15 (s, 3H).

The following Examples were prepared in a similar manner to the product of Example 163.

TABLE 4

| Example No. | NR²R⁵ | MW | m/z [M + H]⁺ | Rt (min) [Method] |
|---|---|---|---|---|
| 164 | 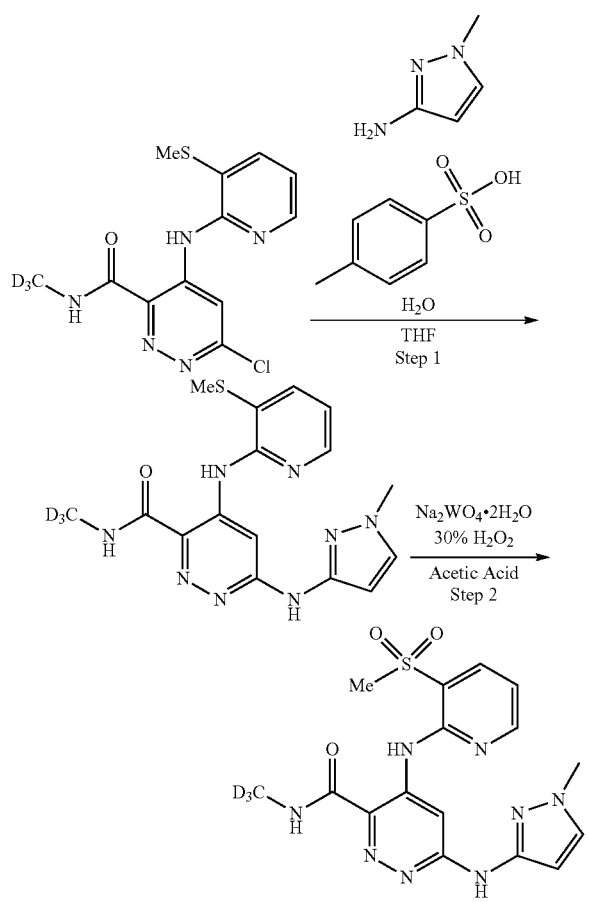 | 407.46 | 408.08 | 0.72 [A] |
| 165 | | 457.52 | 458.08 | 0.59 [B] |

Example 166

Step 1

A mixture of 6-chloro-N-trideuteromethyl-4-((3-(methylthio)pyridin-2-yl)amino)pyridazine-3-carboxamide (100 mg, 0.320 mmol, Intermediate 2), 1-methyl-1H-pyrazol-3-amine (68.3 mg, 0.703 mmol), and 4-methylbenzenesulfonic acid monohydrate (91 mg, 0.480 mmol) in THF (7 mL) was heated in a closed vial at 100° C. for 36 h. The mixture was concentrated under vacuum to dryness. The residue was diluted with DMSO (1.2 mL) and MeOH (4.8 mL), divided into 3 portions, and purified by prep HPLC. The desired fractions were combined, concentrated under vacuum, basified with 1.5 N K₂HPO₄ solution to pH 10, and extracted with DCM (3×35 mL). The combined extracts were dried over anhydrous Na₂SO₄ filtered and concentrated under vacuum to give the desired product, N-trideuteromethyl-6-((1-methyl-1H-pyrazol-3-yl)amino)-4-((3-(methylthio)pyridin-2-yl)amino)pyridazine-3-carboxamide (49 mg, 0.131 mmol, 41.0% yield), as a white solid.

Step 2

To a solution of N-trideuteromethyl-6-((1-methyl-1H-pyrazol-3-yl)amino)-4-((3-(methylthio)pyridin-2-yl)amino)pyridazine-3-carboxamide (49 mg, 0.131 mmol) in acetic acid (3 mL) at rt was added sodium tungstate dihydrate (54.1 mg, 0.164 mmol) in one portion, followed by 30% hydrogen peroxide (0.227 mL, 3.94 mmol). The solution was stirred at rt for 1 h. The mixture was diluted with water (25 mL), basified with solid Na₂CO₃, and extracted with DCM (3×45 mL). The combined extracts were dried over anhydrous Na₂SO₄, filtered and concentrated under vacuum. The residue was dissolved in DMSO (1 mL) and MeOH (3 mL), which was divided into two portions, and purified by prep HPLC. The desired fractions were combined, concentrated under vacuum, basified to pH 10-11 with 1N K₂HPO₄ solution, and extracted with DCM (3×40 mL). The combined extracts were dried over anhydrous Na₂SO₄, filtered and concentrated under vacuum to give the desired product, N-trideuteromethyl-6-((1-methyl-1H-pyrazol-3-yl)amino)-4-((3-(methylsulfonyl)pyridin-2-yl)amino)pyridazine-3-carboxamide (28 mg, 0.068 mmol, 52.1% yield), as a white solid.

MS (M+1) m/z: 406.1 (MH⁺). LC retention time 0.56 min [A].

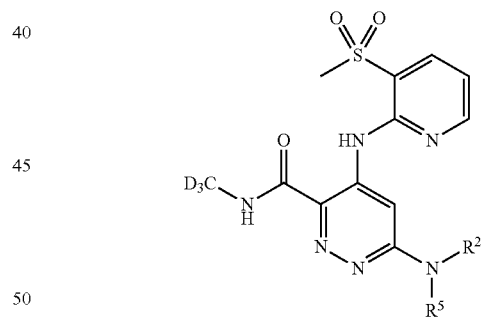

The following Examples were prepared in a similar manner to the product of Example 166.

TABLE 5

| Example No. | NR²R⁵ | MW | m/z [M + H]⁺ | Rt (min) [Method] |
|---|---|---|---|---|
| 167 | 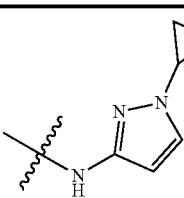 | 431.49 | 432.08 | 0.62 [A] |

TABLE 5-continued

| Example No. | NR²R⁵ | MW | m/z [M + H]⁺ | Rt (min) [Method] |
|---|---|---|---|---|
| 168 | | 405.47 | 406.08 | 0.69 [A] |

Example 169

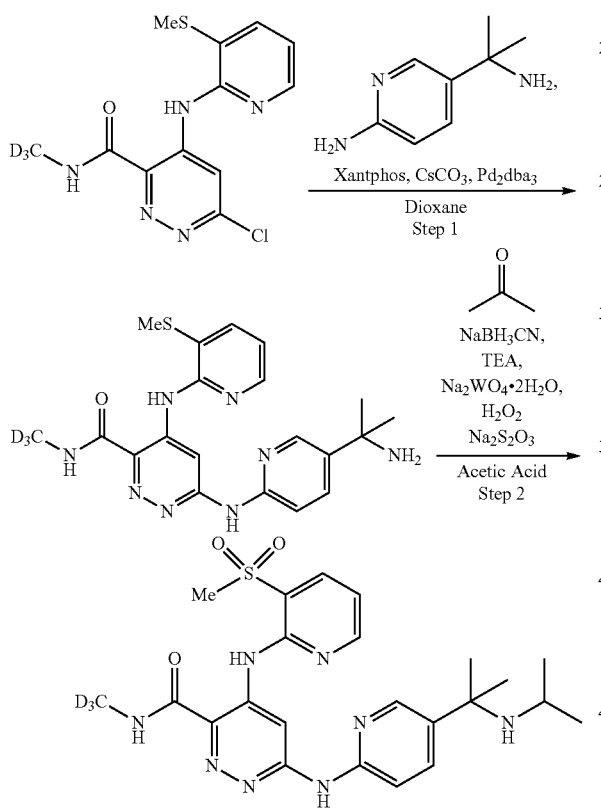

Step 1

A mixture of 6-chloro-N-(methyl-d3)-4-((3-(methylthio) pyridin-2-yl)amino)pyridazine-3-carboxamide (50 mg, 0.160 mmol, Intermediate 2), 5-(2-aminopropan-2-yl)pyridin-2-amine (31.4 mg, 0.208 mmol), Xantphos (13.87 mg, 0.024 mmol), Pd$_2$(dba)$_3$ (10.98 mg, 0.012 mmol) and Cs$_2$CO$_3$ (78 mg, 0.240 mmol) in dioxane (1.5 mL) was purged with nitrogen for 2 min., then stirred at 130° C. for 3 h. After cooling, the solid was collected via filtration and used as is in the next reaction.

MS (M+1) m/z: 428.35 (MH⁺). LC retention time 0.90 min [C].

Step 2

The 6-((5-(2-aminopropan-2-yl)pyridin-2-yl)amino)-N-(methyl-d3)-4-((3-(methylthio)pyridin-2-yl)amino) pyridazine-3-carboxamide (13 mg, 0.030 mmol) was mixed with 1 mL of DCM, propan-2-one (1.766 mg, 0.030 mmol) was added, followed by the addition of sodium cyanoborohydride (3.82 mg, 0.061 mmol) and TEA (8.48 µl, 0.061 mmol) The mixture was stirred at rt overnight. The mixture was diluted with DCM (20 mL), washed with saturated NaHCO$_3$ (10 mL) and brine (10 mL), dried and concentrated under vacuum. The resulting residue was mixed with AcOH (1 mL), sodium tungstate dihydrate (3.01 mg, 9.12 µmol) and then hydrogen peroxide (0.155 mL, 1.520 mmol). The mixture was stirred at rt for 1 h. To the mixture was added sodium thiosulfate (961 mg, 1.520 mmol) and then stirred for 10 min. The mixture was filtered and purified with prep HPLC to provide the desired product, 6-((5-(2-(isopropylamino)propan-2-yl)pyridin-2-yl)amino)-N-(methyl-d3)-4-((3-(methylsulfonyl)pyridin-2-yl)amino)pyridazine-3-carboxamide (3.8 mg, 7.5 µmol, 24.66% yield).

MS (M+1) m/z: 502 (MH⁺). LC retention time 1.3 min [QC-ACN-AA-XB].

¹H NMR (500 MHz, DMSO-d$_6$) δ 9.59-9.44 (m, 1H), 9.23-9.06 (m, 1H), 8.73-8.60 (m, 1H), 8.40-8.33 (m, 1H), 8.31-8.24 (m, 1H), 7.92-7.84 (m, 1H), 7.65-7.56 (m, 1H), 7.37-7.29 (m, 1H), 1.48-1.33 (m, 6H), 0.93-0.76 (m, 6H).

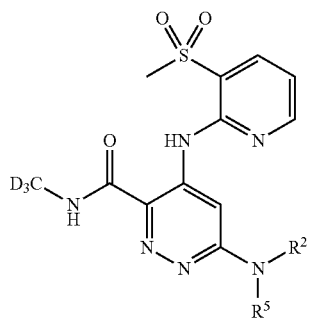

The following Example was prepared in a similar manner to the product of Example 169.

TABLE 6

| Example No. | NR²R⁵ | MW | m/z [M + H]⁺ | Rt (min) [Method] |
|---|---|---|---|---|
| 170 | | 515.60 | 516.4 | 0.84 [C] |

Example 171

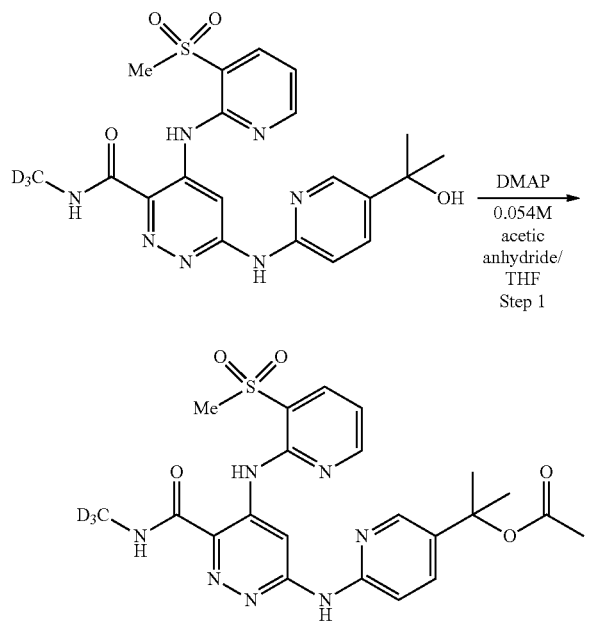

Step 1

A heterogeneous solution of 6-((5-(2-hydroxypropan-2-yl)pyridin-2-yl)amino)-N-(methyl-d3)-4-((3-(methylsulfonyl)pyridin-2-yl)amino)pyridazine-3-carboxamide (0.0627 g, 0.136 mmol, Example 13) and DMAP (0.0183 g, 0.150 mmol) in 0.054M acetic anhydride/THF (6.30 ml, 0.340 mmol) in a sealed vial was heated to 80° C. The reaction was stirred for 2 days. The reaction was cooled to room temperature. Acetic anhydride (0.020 mL, 0.212 mmol, 1.56 eq.) was added, and heating was resumed. The reaction was stirred for another day and the starting material was consumed. The reaction was cooled to rt and DMAP and EtOH were added. The heating was resumed for another day and the reaction was cooled to rt. The reaction was diluted with EtOAc (50 mL) and washed with water (20 mL). The organic layer was washed with brine, dried over $Na_2SO_4$ and filtered. Silica gel (~0.4 g) was added to the filtrate and concentrated in vacuo. The crude product was purified by flash chromatography using an ISCO 24 g column eluting with 0-5% MeOH/ethyl acetate. Appropriate fractions were collected and concentrated in vacuo to give a residue containing the desired product. This residue was triturated with MeOH and dried overnight under vacuum to give 2-(6-((6-((methyl-d3)carbamoyl)-5-((3-(methylsulfonyl)pyridin-2-yl)amino)pyridazin-3-yl)amino)pyridin-3-yl)propan-2-yl acetate (0.01025 g, 0.019 mmol, 14.23% yield) as a white solid.

MS (M+1) m/z: 503.2 (MH$^+$). LC retention time 0.67 min [B].

$^1$H NMR (400 MHz, DMSO-d$_6$) δ 12.18-12.04 (m, 1H), 10.40-10.29 (m, 1H), 9.58-9.45 (m, 1H), 9.23-9.08 (m, 1H), 8.75-8.64 (m, 1H), 8.38-8.19 (m, 2H), 7.79-7.71 (m, 1H), 7.70-7.62 (m, 1H), 7.38-7.30 (m, 1H), 3.42-3.35 (m, 3H), 2.07-1.95 (m, 3H), 1.82-1.65 (m, 6H).

Example 172

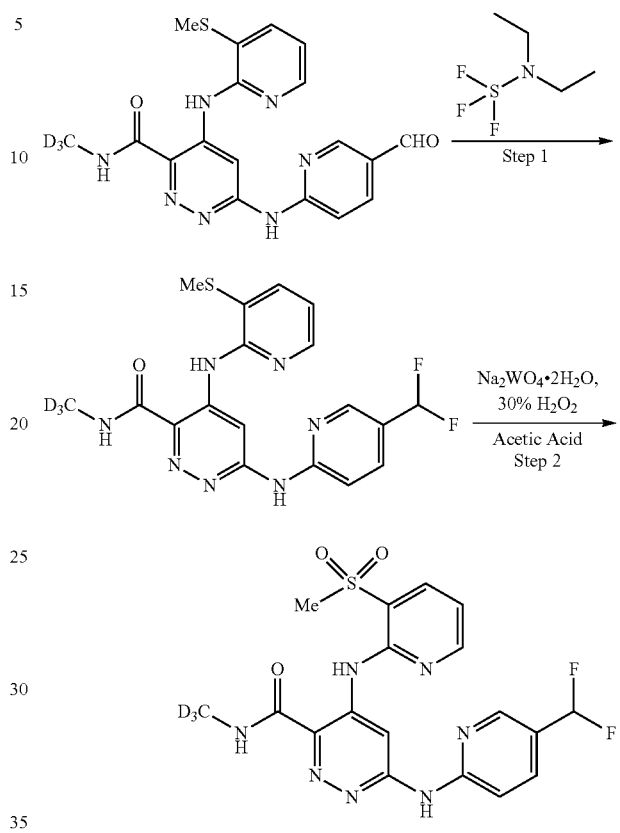

Step 1

To a suspension of 6-((5-formylpyridin-2-yl)amino)-N-(methyl-d3)-4-((3-(methylthio)pyridin-2-yl)amino)pyridazine-3-carboxamide (130 mg, 0.326 mmol) in DCM (11 mL) at rt was added (diethylamino)sulfur trifluoride (DAST) (0.28 mL, 2.119 mmol) dropwise. The mixture was heated at 45° C. for 16 h. After cooling to rt, the reaction was carefully quenched with water (20 mL). The resulting mixture was basified with solid $Na_2CO_3$ to pH 9-10 and extracted with DCM (3×40 mL). The combined extracts were dried over anhydrous $Na_2SO_4$. The desired product, 6-((5-(difluoromethyl)pyridin-2-yl)amino)-N-(methyl-d3)-4-((3-(methylthio)pyridin-2-yl)amino)pyridazine-3-carboxamide (47 mg, 0.112 mmol, 34.3% yield), was isolated as a white solid by ISCO (40 g silica gel, solid loading, 0-5% methanol/dichloromethane).

MS (M+1) m/z: 421.08 (MH$^+$). LC retention time 0.74 min [B].

Step 2

To a solution of 6-((5-(difluoromethyl)pyridin-2-yl)amino)-N-(methyl-d3)-4-((3-(methylthio)pyridin-2-yl)amino)pyridazine-3-carboxamide (47 mg, 0.112 mmol) in acetic acid (4 mL) at rt was added sodium tungstate dihydrate (46.1 mg, 0.140 mmol) in one portion, followed by 30% hydrogen peroxide (0.343 ml, 3.35 mmol). The solution was stirred at rt for 1 h. The mixture was diluted with water (30 mL), basified with solid $Na_2CO_3$, and extracted with DCM (3×45 mL). The combined extracts were dried over anhydrous $Na_2SO_4$. The desired product, 6-((5-(difluoromethyl)pyridin-2-yl)amino)-N-(methyl-d3)-4-((3-(methylsulfonyl)pyridin-2-yl)amino)pyridazine-3-carboxamide (20 mg, 0.044 mmol, 39.1% yield), was isolated as a white solid by ISCO (24 g silica gel, solid loading, 0-5% MeOH/DCM).

MS (M+1) m/z: 453.08 (MH$^+$). LC retention time 0.63 min [A].

$^1$H NMR (400 MHz, DMSO-d$_6$) δ 12.19-12.09 (m, 1H), 10.72-10.61 (m, 1H), 9.66-9.54 (m, 1H), 9.26-9.16 (m, 1H), 8.79-8.64 (m, 1H), 8.56-8.45 (m, 1H), 8.35-8.24 (m, 1H), 8.01-7.89 (m, 1H), 7.85-7.73 (m, 1H), 7.40-7.29 (m, 1H), 7.25-6.81 (m, 1H), 3.34-3.30 (m, 3H).

Example 173

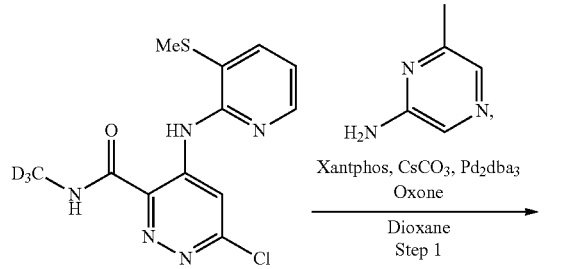

Step 1

A mixture of 6-chloro-N-(methyl-d3)-4-((3-(methylthio)pyridin-2-yl)amino)pyridazine-3-carboxamide (30 mg, 0.096 mmol, Intermediate 2), 6-methylpyrazin-2-amine (31.4 mg, 0.288 mmol), Xantphos (8.32 mg, 0.014 mmol), Pd$_2$(dba)$_3$ (6.59 mg, 7.19 μmol) and Cs$_2$CO$_3$ (125 mg, 0.384 mmol) in dioxane (1.5 mL) was purged with nitrogen for 2 min, then stirred at 130° C. for 3 h. The mixture was mixed with MeOH/DCM (1:1, 5 mL), filtered and the filtrate was concentrated and the residue was used in the next step. The above residue was mixed with MeOH (1 mL), acetone (1 mL) and water (0.5 mL). Oxone (177 mg, 0.288 mmol) was added and the mixture was stirred at r.t for 18 h. The reaction mixture was concentrated to dryness then dissolved in DMSO and purified with prep HPLC. The reaction provided N-(methyl-d3)-6-((6-methylpyrazin-2-yl)amino)-4-((3-(methylsulfonyl)pyridin-2-yl)amino)pyridazine-3-carboxamide (3.4 mg, 7.74 nmol, 8% yield).

MS (M+1) m/z: 418.1 (MH$^+$). LC retention time 0.95 min [QC-ACN-TFA-XB].

$^1$H NMR (500 MHz, DMSO-d$_6$) δ 12.27-12.00 (m, 1H), 10.74-10.47 (m, 1H), 9.68-9.55 (m, 1H), 9.27-9.10 (m, 1H), 8.77-8.61 (m, 2H), 8.38-8.21 (m, 1H), 8.13-8.00 (m, 1H), 7.42-7.31 (m, 1H), 3.37 (s, 3H), 2.47-2.41 (m, 3H).

Example 174

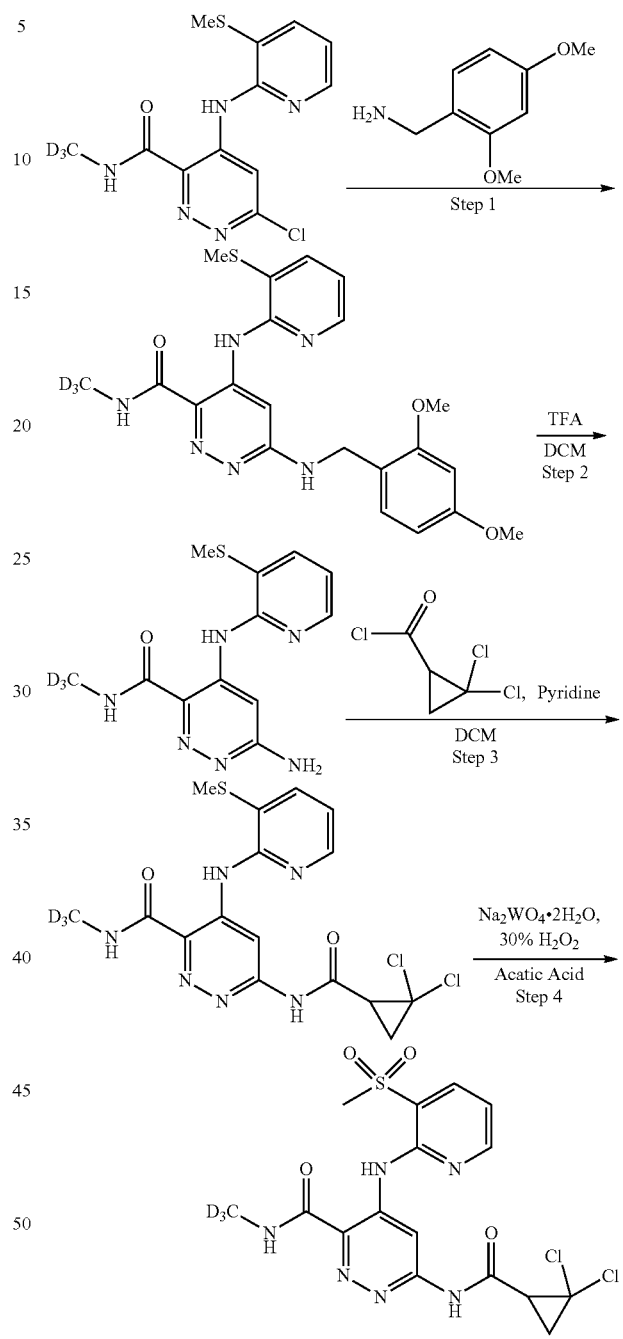

Step 1

6-chloro-N-(methyl-d3)-4-((3-(methylthio)pyridin-2-yl)amino)pyridazine-3-carboxamide (0.5304 g, 1.696 mmol, Intermediate 2) and (2,4-dimethoxyphenyl)methanamine (2.1068 g, 12.60 mmol) were melted at 145° C. Vapors appeared by 88° C. After 1.5 hrs, EtOAc (150 mL) and 1M aqueous K$_2$HPO$_4$ (40 mL) were added. After separation of layers, the organic layer was washed with 1M aq. K$_2$HPO$_4$ (40 mL) and brine (40 mL) successively, dried over Na$_2$SO$_4$ and filtered. Silica gel was added to the filtrate and concentrated in vacuo. The crude product was purified by flash chromatography using an ISCO 120 g column eluting with 0-5% MeOH/DCM (0%, cv2; 0-5%, cv12). Appropriate fractions (1.6-2.2%) were collected and concentrated in vacuo to give 6-((2,4-dimethoxybenzypamino)-N-(methyl-d3)-4-((3-(methylthio)pyridin-2-yl)amino)pyridazine-3-carboxamide (0.7215 g, 1.627 mmol, 96% yield) as a yellow solid.

MS (M+1) m/z: 444.2 (M+). LC retention time 0.79 min [A].

Step 2

To a homogeneous yellow solution of 6-((2,4-dimethoxybenzypamino)-N-(methyl-d3)-4-((3-(methylthio)pyridin-2-yl)amino)pyridazine-3-carboxamide (0.7215 g, 1.627 mmol) in dichloromethane (20 mL) at 0° C. under nitrogen was added trifluoroacetic acid (20 mL, 260 mmol) dropwise. After 10 min, the ice-water bath was removed and the reaction was stirred at rt overnight. The mixture was concentrated in vacuo and diluted with DCM (100 mL) and 1.5 M aqueous K₂HPO₄ (25 mL). After separation of layers, the aq layer was extracted with DCM (4×100 mL). The organic layers were combined, dried over Na₂SO₄, filtered and concentrated in vacuo (0.68 g). THF was added, and the heterogeneous solution was filtered and the filtrate concentrated in vacuo. The crude product was purified by flash chromatography using an ISCO 120 g column eluting with 0-75% MeOH/CH₂Cl₂. Appropriate fractions were collected and concentrated in vacuo to give 6-amino-N-(methyl-d3)-4-((3-(methylthio)pyridin-2-yl)amino)pyridazine-3-carboxamide (0.2534 g, 0.864 mmol, 53.1% yield) as a yellow solid.

MS (M+1) m/z: 294.0 (MH+). LC retention time 0.60 min [A].

Step 3

To a heterogeneous solution of 6-amino-N-(methyl-d3)-4-((3-(methylthio)pyridin-2-yl)amino)pyridazine-3-carboxamide (0.042 g, 0.143 mmol) in dichloromethane (2.0 mL) was added pyridine (0.05 ml, 0.618 mmol). A solution of 2,2-dichlorocyclopropanecarbonyl chloride in DCM (0.17 M, 1.0 ml, 0.17 mmol) was then added leading to homogeneity. After 1 h the reaction additional 2,2-dichlorocyclopropanecarbonyl chloride in DCM (0.17 M, 1.0 ml, 0.17 mmol) was added. Stirring was continued for several hours and then additional 2,2-dichlorocyclo propanecarbonyl chloride in DCM (0.17 M, 1.0 ml, 0.17 mmol) was added and stirring continued overnight. Additional 2,2-dichlorocyclopropanecarbonyl chloride/in DCM (0.47 M, 0.61 mL, 0.29 mmol) was added and after conversion, was determined to be ~50%. Heating the reaction vessel to 50° C. provided no further conversion. The reaction was cooled to rt, diluted with DCM (40 mL) and washed with water (5 mL). The organic layer was further washed with water (5 mL) and brine (5 mL) successively, dried over Na₂SO₄ and filtered. Silica gel was added to the filtrate and concentrated in vacuo. The crude product was purified by flash chromatography using an ISCO 12 g column eluting with 0-10% MeOH/CH₂Cl₂. Appropriate fractions were collected and concentrated in vacuo to give impure desired product (~50% pure, 52.8 mg), used as is in the subsequent reaction.

Step 4

To a homogeneous, yellow solution of 6-(2,2-dichlorocyclopropane-1-carboxamido)-N-(methyl-d3)-4-((3-(methylthio)pyridin-2-yl)amino)pyridazine-3-carboxamide (0.0528 g, 0.123 mmol) in acetic acid (1.5 mL) was added sodium tungstate dihydrate (0.0561 g, 0.170 mmol), followed by 30% hydrogen peroxide (0.4 mL, 3.92 mmol). After 1.5 h, water (25 mL) was added and the reaction was immersed in an ice-water bath. Na₂CO₃ (solid) was added until pH was basic by litmus paper. This was extracted with DCM (4×50 mL). The organic layers were combined and then washed with 1N aq HCl (30 mL), saturated aq NaHCO₃ (30 mL) and brine (30 mL) successively, dried over Na₂SO₄, filtered and concentrated in vacuo. The crude product was purified by flash chromatography using an ISCO 12 g column eluting with 0-5% MeOH/DCM (0%, cv2; 0-10%, cv20). Appropriate fractions were collected, concentrated in vacuo and dried in a desiccator oven at 50° C. to give 6-(2,2-dichlorocyclopropane-1-carboxamido)-N-(methyl-d3)-4-((3-(methylsulfonyl)pyridin-2-yl)amino)pyridazine-3-carboxamide (0.00691 g, 0.015 mmol, 12.2% yield).

MS (M+1) m/z: 462.1 (MH+). LC retention time 0.79 min [B].

¹H NMR (400 MHz, DMSO-d₆) δ 12.24-12.08 (m, 1H), 11.91-11.77 (m, 1H), 9.59-9.46 (m, 1H), 9.35-9.20 (m, 1H), 8.75-8.52 (m, 1H), 8.37-8.19 (m, 1H), 7.40-7.26 (m, 1H), 3.39-3.34 (m, 3H), 3.22-3.13 (m, 1H), 2.16-1.99 (m, 2H).

Examples 175 and 176

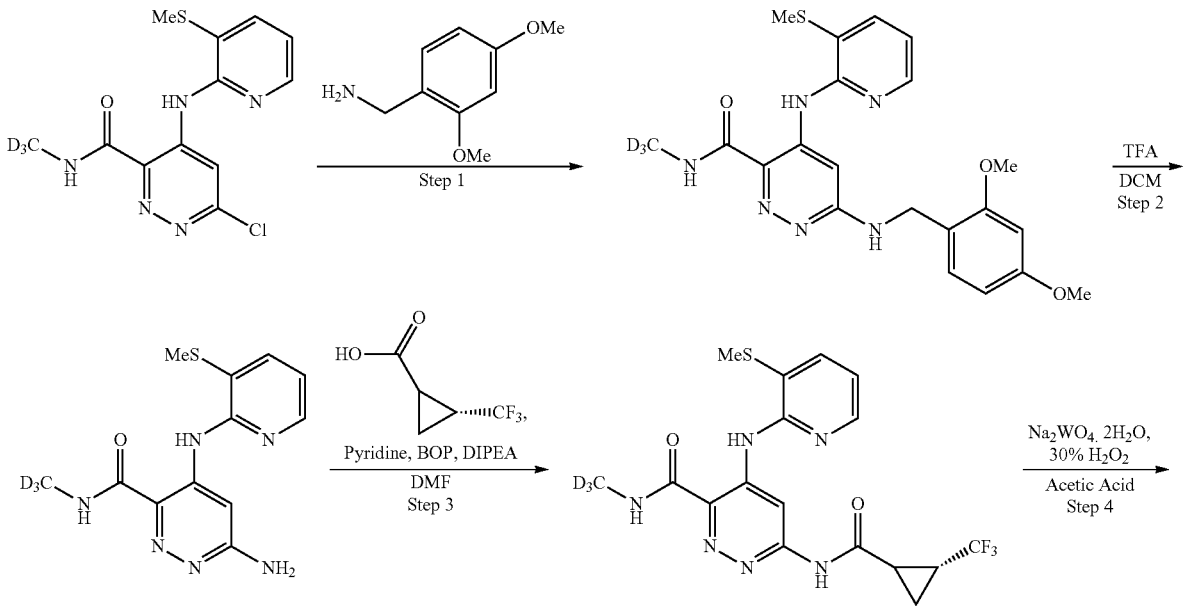

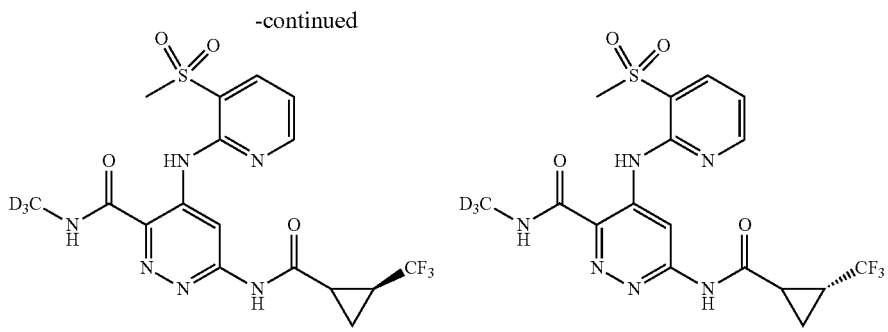

Steps 1 & 2

Follow the procedures shown above to prepare Example 174.

Step 3

A mixture of 6-amino-N-(methyl-d3)-4-((3-(methylthio)pyridin-2-yl)amino)pyridazine-3-carboxamide (97 mg, 0.331 mmol), (±)-trans-2-(trifluoromethyl)cyclopropane-1-carboxylic acid (76 mg, 0.496 mmol), BOP (205 mg, 0.463 mmol), and N,N-diisopropylethylamine (0.202 mL, 1.157 mmol) in DMF (2 mL) was heated at 60° C. for 2 h. The desired product was detected, but the majority of the starting material remained. The mixture was continued to be heated at 60° C. overnight but no change was noticed. The reaction mixture was diluted with ethyl acetate (50 mL), washed with water (3×15 mL) and brine (15 mL), and dried over anhydrous MgSO$_4$. The product, (±)-N-(methyl-d3)-4-((3-(methylthio)pyridin-2-yl)amino)-6-((1R,2R)-2-(trifluoromethyl)cyclopropane-1-carboxamido)pyridazine-3-carboxamide (23.6 mg, 0.055 mmol, 16.62% yield), was isolated as a beige solid. MS (M+1) m/z: 430.2 (MH$^+$). LC retention time 0.90 min [A]. The starting material, 6-amino-N-(methyl-d3)-4-((3-(methylthio)pyridin-2-yl)amino)pyridazine-3-carboxamide (60 mg, 0.205 mmol, 61.9% yield), was partially recovered as a beige solid.

Step 4

To a solution of (±)-N-(methyl-d3)-4-((3-(methylthio)pyridin-2-yl)amino)-6-((1R,2R)-2-(trifluoromethyl)cyclopropane-1-carboxamido)pyridazine-3-carboxamide (23.6 mg, 0.055 mmol) in acetic acid (4 mL) at rt was added sodium tungstate dihydrate (22.66 mg, 0.069 mmol) in one portion, followed by dropwise addition of 30% hydrogen peroxide (0.168 mL, 1.649 mmol). The solution was stirred at rt for 1 h. The mixture was diluted with water (20 mL), basified with solid Na$_2$CO$_3$, and extracted with DCM (4×30 mL). The combined extract was dried over anhydrous Na$_2$SO$_4$. The title compound, N-(methyl-d3)-4-((3-(methylsulfonyl)pyridin-2-yl)amino)-6-((1R,2R)-2-(trifluoromethyl)cyclopropane-1-carboxamido)pyridazine-3-carboxamide (10 mg, 0.022 mmol, 39.4% yield), was isolated as a white solid by ISCO (24 g silica gel, solid loading, 0-5% MeOH/dichloromethane).

MS (M+1) m/z: 462.1 (MH$^+$). LC retention time 0.79 min [A].

A racemate sample (10 mg) obtained as above went through chiral separation to give N-(methyl-d3)-4-((3-(methylsulfonyl)pyridin-2-yl)amino)-6-((1S,2S)-2-(trifluoromethyl)cyclopropane-1-carboxamido)pyridazine-3-carboxamide (4.52 mg, 9.31 μmol, 86% yield), $^1$H NMR (400 MHz, DMSO-d$_6$) δ 12.19-12.09 (m, 1H), 11.73-11.63 (m, 1H), 9.53-9.47 (m, 1H), 9.32-9.20 (m, 1H), 8.65-8.54 (m, 1H), 8.38-8.24 (m, 1H), 7.41-7.29 (m, 1H), 3.38-3.35 (m, 3H), 2.71-2.61 (m, 1H), 2.41-2.28 (m, 1H), 1.41-1.30 (m, 2H), and N-(methyl-d3)-4-((3-(methylsulfonyl)pyridin-2-yl)amino)-6-((1R,2R)-2-(trifluoromethyl)cyclopropane-1-carboxamido)pyridazine-3-carboxamide (4.36 mg, 8.98 μmol, 83% yield) as white solids, $^1$H NMR (400 MHz, DMSO-d$_6$) δ 12.20-12.08 (m, 1H), 11.73-11.58 (m, 1H), 9.57-9.44 (m, 1H), 9.33-9.18 (m, 1H), 8.69-8.50 (m, 1H), 8.37-8.21 (m, 1H), 7.41-7.25 (m, 1H), 3.40-3.34 (m, 3H), 2.72-2.62 (m, 1H), 2.42-2.30 (m, 1H), 1.40-1.29 (m, 2H).

The absolute stereochemistry of the two enantionmers was randomly assigned.

Example 177

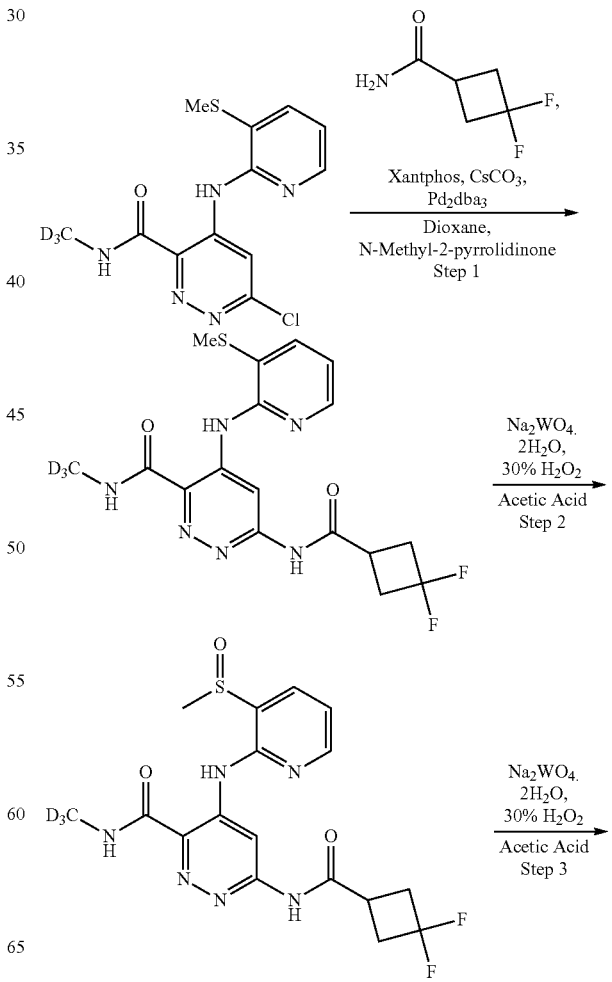

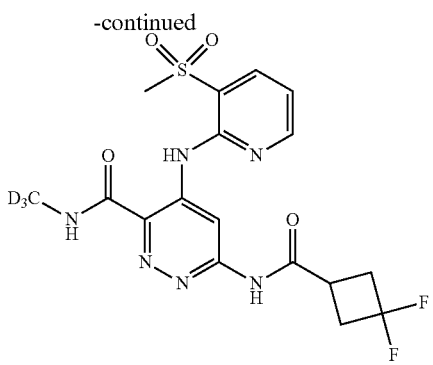

Step 1

A mixture of 6-chloro-N-trideuteromethyl-4-((3-(methylthio)pyridin-2-yl)amino)pyridazine-3-carboxamide (150 mg, 0.480 mmol), 3,3-difluorocyclobutanecarboxamide (87 mg, 0.647 mmol), tris(dibenzylideneacetone) dipalladium (0) (65.9 mg, 0.072 mmol), Xantphos (41.6 mg, 0.072 mmol), and cesium carbonate (281 mg, 0.863 mmol) in 1,4-dioxane (10 mL) was heated under microwave at 145° C. for 1 h. The reaction mixture was diluted with ethyl acetate (20 mL) and filtered through Celite. The filtrate was further diluted with ethyl acetate (20 mL) and filtered through Celite. The filtrate was concentrated under vacuum to dryness. To the residue was added water (50 mL), followed by saturated NaHCO₃ solution (5 mL). The insoluble material was collected by suction filtration and further purified by ISCO (40 g silica gel, solid loading, 0-4% MeOH/DCM) to give the desired product, 6-((3,3-difluorocyclobutane-1-carboxamido)-N-(methyl-d3)-4-((3-(methylthio)pyridin-2-yl)amino)pyridazine-3-carboxamide (57 mg, 0.139 mmol, 28.9% yield), as a beige solid.

MS (M+1) m/z: 412.2 (MH⁺). LC retention time 0.89 min [A].

Step 2

To a suspension of 6-(3,3-difluorocyclobutane-1-carboxamido)-N-(methyl-d3)-4-((3-(methylthio)pyridin-2-yl)amino)pyridazine-3-carboxamide (57 mg, 0.139 mmol) in acetic acid (20 mL) at rt was added sodium tungstate dihydrate (57.1 mg, 0.173 mmol) in one portion, followed by 30% hydrogen peroxide (0.425 mL, 4.16 mmol). The solution was stirred at rt for 1 h. The starting material was all converted to sulfoxide but not the desired sulfone. Additional sodium tungstate dihydrate (57.1 mg, 0.173 mmol) and 30% hydrogen peroxide (0.213 mL, 2.08 mmol) were added. The heterogeneous mixture was stirred at rt for another hour. The mixture was diluted with water (40 mL), basified with solid Na₂CO₃ and extracted with DCM (4×50 mL). The combined extracts were dried over anhydrous Na₂SO₄, filtered and concentrated in vacuo. The product, 6-(3,3-difluorocyclobutane-1-carboxamido)-N-(methyl-d3)-4-((3-(methylsulfinyl)pyridin-2-yl)amino)pyridazine-3-carboxamide (15 mg, 0.035 mmol, 25.3% yield), was isolated as a white solid by ISCO (24 g silica gel, solid loading, 0-5% MeOH/DCM).

MS (M+1) m/z: 428.2 (MH⁺). LC retention time 0.7 min [A].

Step 3

To a suspension of 6-(3,3-difluorocyclobutane-1-carboxamido)-N-(methyl-d3)-4-((3-(methylsulfinyl)pyridin-2-yl)amino)pyridazine-3-carboxamide (15 mg, 0.035 mmol) in acetic acid (3 ml) at rt was added sodium tungstate dihydrate (14.47 mg, 0.044 mmol) in one portion, followed by 30% hydrogen peroxide (0.108 mL, 1.053 mmol). The solution was stirred at rt for 1.5 h. The mixture was diluted with water (20 mL), basified with solid Na₂CO₃ and extracted with DCM (3×40 mL). The combined extract was dried over anhydrous Na₂SO₄ and concentrated under vacuum to dryness. The residue was dissolved in DMSO (1.2 mL) and purified by prep HPLC. The desired product, 6-(3,3-difluorocyclobutane-1-carboxamido)-N-(methyl-d3)-4-((3-(methylsulfonyl)pyridin-2-yl)amino)pyridazine-3-carboxamide (5.8 mg, 0.013 mmol, 36.2% yield), was obtained.

MS (M+1) m/z: 444.0 (MH⁺). LC retention time 1.39 min [QC-ACN-TFA-XB].

Example 178

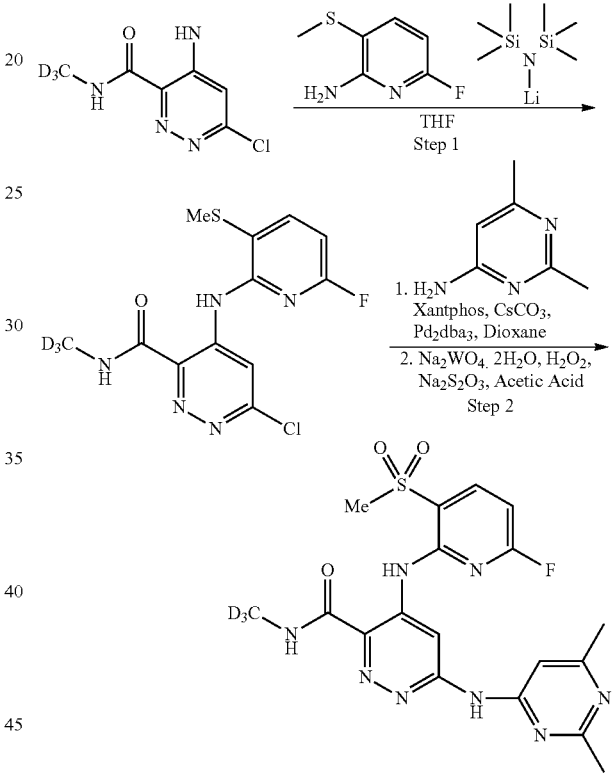

Step 1

To a solution of 4,6-dichloro-N-trideuteromethylpyridazine-3-carboxamide (114 mg, 0.544 mmol) and 6-fluoro-3-(methylthio)pyridin-2-amine (86 mg, 0.544 mmol) in THF (5 mL) at rt was added lithium bis(trimethylsilyl)amide in THF (1.359 mL, 1.359 mmol) over 5 min. The resulting mixture was stirred at rt for 1 h. The reaction was quenched with water (5 mL), the mixture was adjusted with 1N HCl solution to pH 9-10, and further diluted with water (10 mL). The precipitating product, 6-chloro-4-((6-fluoro-3-(methylthio)pyridin-2-yl)amino)-N-(methyl-d3)pyridazine-3-carboxamide (145 mg, 0.438 mmol, 81% yield), was collected as a pale solid by suction filtration and dried under vacuum.

MS (M+1) m/z: 331.25 (MH¹). LC retention time 1.19 min [C].

¹H NMR (400 MHz, DMSO-d₆) δ 12.65-12.53 (m, 1H), 9.62-9.42 (m, 1H), 9.04-8.85 (m, 1H), 8.22-8.06 (m, 1H), 7.00-6.83 (m, 1H).

Step 2

A mixture of 6-chloro-4-((6-fluoro-3-(methylthio)pyridin-2-yl)amino)-N-(methyl-d3)pyridazine-3-carboxamide (30 mg, 0.091 mmol), 2,6-dimethylpyrimidin-4-amine (16.75 mg, 0.136 mmol), Xantphos (7.87 mg, 0.014 mmol), Pd$_2$(dba)$_3$ (6.23 mg, 6.80 μmol) and Cs$_2$CO$_3$ (59.1 mg, 0.181 mmol) in dioxane (1.5 mL) was purged with nitrogen for 2 min, then stirred at 130° C. for 3 h. The mixture was mixed with MeOH/DCM (1:1, 5 ml), filtered and the filtrate was concentrated. The resulting residue was used in the next step. The residue was mixed with AcOH (1 mL) and sodium tungstate dihydrate (8.97 mg, 0.027 mmol) was added. Hydrogen peroxide (278 μL, 2.72 mmol) was added and the mixture was stirred at rt for 1 h. To this mixture was added sodium thiosulfate (430 mg, 2.72 mmol) and the reaction stirred for 10 min. The mixture was filtered and purified with prep HPLC to provide the product, 6-((2,6-dimethylpyrimidin-4-yl)amino)-4-((6-fluoro-3-(methylsulfonyl)pyridin-2-yl)amino)-N-(methyl-d3)pyridazine-3-carboxamide (6.8 mg, 0.014 mmol, 15.85% yield).

MS (M+1) m/z: 449.9 (MH$^+$). LC retention time 1.11 min [QC-ACN-TFA-XB].

$^1$H NMR (500 MHz, DMSO-d$_6$) δ 10.83-10.68 (m, 1H), 9.48-9.34 (m, 1H), 9.32-9.15 (m, 1H), 8.52-8.35 (m, 1H), 7.42-7.24 (m, 1H), 7.02 (br s, 1H), 3.39 (br s, 3H), 2.57-2.53 (m, 6H).

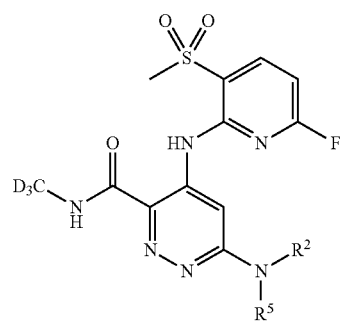

The following examples were prepared in a similar manner to the product of Example 178.

TABLE 7

| Example No. | NR$^2$R$^5$ | MW | m/z [M + H]$^+$ | Rt (min) [Method] |
|---|---|---|---|---|
| 179 | | 399.41 | 399.9 | 1.26 [QC-ACN-TFA-XB] |
| 180 | | 411.42 | 412.2 | 1.16 [QC-ACN-TFA-XB] |
| 181 | | 451.45 | 452.0 | 1.24 [QC-ACN-AA-XB] |

TABLE 7-continued

| Example No. | NR$^2$R$^5$ | MW | m/z [M + H]$^+$ | Rt (min) [Method] |
|---|---|---|---|---|
| 182 | | 533.5 | 533.9 | 1.62 [QC-ACN-AA-XB] |

Example 183

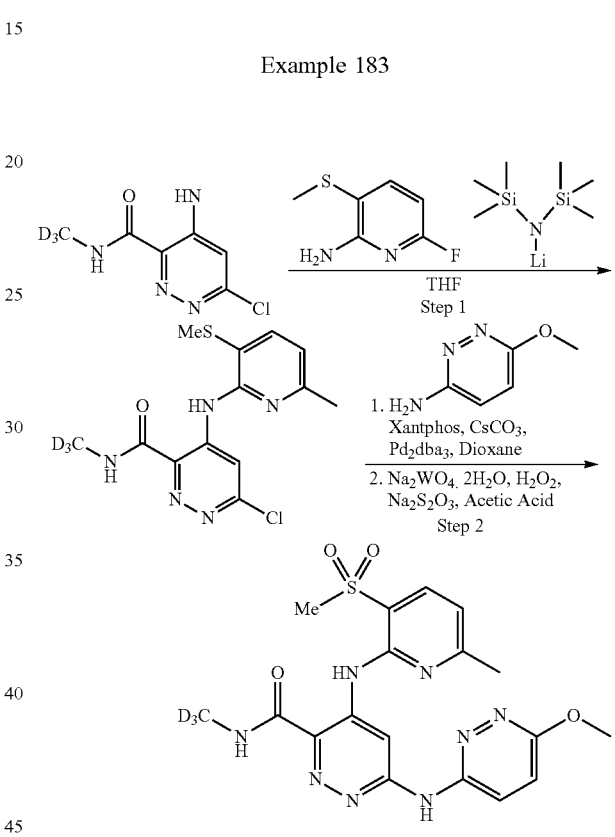

Step 1

To a solution of 4,6-dichloro-N-trideuteromethylpyridazine-3-carboxamide (144 mg, 0.687 mmol) and 6-methyl-3-(methylthio)pyridin-2-amine (106 mg, 0.687 mmol) in THF (5 mL) at rt was added lithium bis(trimethylsilyl)amide in THF (1.718 mL, 1.718 mmol) over 5 min. The resulting mixture was stirred at rt for 1 h. The reaction was quenched with water (5 mL), the mixture adjusted with 1N HCl solution to pH 9-10, and further diluted with water (10 mL). The precipitating product, 6-chloro-N-(methyl-d3)-4-((6-methyl-3-(methylthio)pyridin-2-yl)amino)pyridazine-3-carboxamide (160 mg, 0.490 mmol, 71.2% yield), was collected as a pale solid by suction filtration and dried under vacuum.

MS (M+1) m/z: 327.3 (MH$^+$). LC retention time 1.27 min [C].

$^1$H NMR (400 MHz, DMSO-d$_6$) δ 12.41-12.25 (m, 1H), 9.49-9.36 (m, 1H), 9.29-9.14 (m, 1H), 7.91-7.77 (m, 1H), 7.10-6.96 (m, 1H), 2.49-2.48 (m, 6H)

Step 2

A mixture of 6-chloro-N-(methyl-d3)-4-((6-methyl-3-(methylthio)pyridin-2-yl)amino)pyridazine-3-carboxamide (30 mg, 0.092 mmol), 6-methoxypyridazin-3-amine (17.23 mg, 0.138 mmol), Xantphos (7.97 mg, 0.014 mmol), $Pd_2(dba)_3$ (6.30 mg, 6.88 μmol) and $Cs_2CO_3$ (59.8 mg, 0.184 mmol) in dioxane (1.5 mL) was purged with nitrogen for 2 min, then stirred at 130° C. for 3 h. The mixture was mixed with MeOH/DCM (1:1, 5 ml), filtered and the filtrate was concentrated and the residue was used in the next step. The resulting residue was mixed with AcOH (1 mL) and sodium tungstate dihydrate (9.08 mg, 0.028 mmol). Hydrogen peroxide (281 μl, 2.75 mmol) was added and the mixture was stirred at rt for 1 h. To this mixture was added sodium thiosulfate (435 mg, 2.75 mmol) and the mixture was stirred for 10 min. The mixture was filtered and purified with prep HPLC to give the product, 6-((6-methoxypyridazin-3-yl)amino)-N-(methyl-d3)-4-((6-methyl-3-(methylsulfonyl)pyridin-2-yl)amino)pyridazine-3-carboxamide (4.2 mg, 9.10 μmol, 9.92% yield).

MS (M+1) m/z: 447.8 (MH$^+$). LC retention time 1.01 min [QC-ACN-TFA-XB].

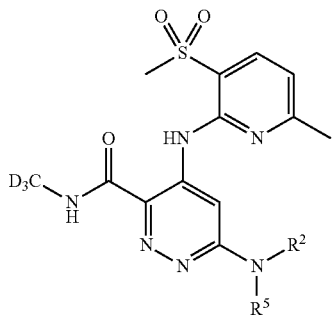

The following examples were prepared in a similar manner to the product of Example 183.

TABLE 8

| Example No. | NR²R⁵ | MW | m/z [M + H]⁺ | Rt (min) [Method] |
|---|---|---|---|---|
| 184 | | 529.54 | 530.3 | 1.41 [QC-ACN-TFA-XB] |
| 185 | | 445.5 | 446.1 | 0.89 [QC-ACN-TFA-XB] |
| 186 | | 395.45 | 396.3 | 1.24 [QC-ACN-AA-XB] |
| 187 | | 407.46 | 408.1 | 1.35 [QC-ACN-AA-XB] |
| 188 | | 474.55 | 475.2 | 1.20 [QC-ACN-AA-XB] |
| 189 | | 544.0 | 544.3 | 1.40 [QC-ACN-AA-XB] |

TABLE 8-continued
| Example No. | NR²R⁵ | MW | m/z [M + H]⁺ | Rt (min) [Method] |
|---|---|---|---|---|
| 190 |  | 577.55 | 578.3 | 1.57 [QC-ACN-AA-XB] |
| 191 | 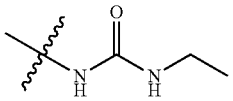 [SMILES: *NC(=O)NCC] | 410.46 | 411.1 | 1.30 [QC-ACN-AA-XB] |
| 192 | 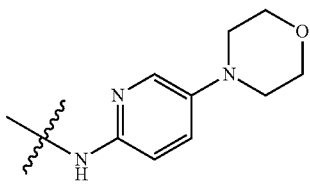 [SMILES: *Nc1ccc(N2CCOCC2)cn1] | 501.58 | 502.2 | 1.23 [QC-ACN-TFA-XB] |
| 193 | 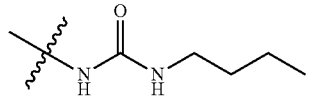 [SMILES: *NC(=O)NCCCC] | 438.52 | 440.5 | 1.48 [QC-ACN-AA-XB] |
| 194 | 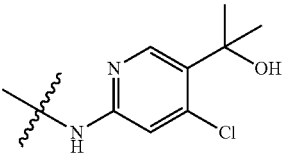 [SMILES: *Nc1cc(Cl)c(C(C)(C)O)cn1] | 509.0 | 509.3 | 1.49 [QC-ACN-AA-XB] |
| 195 | 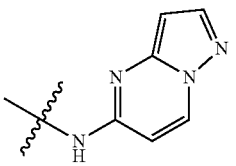 [SMILES: *Nc1ccn2nccc2n1] | 456.5 | 457.1 | 1.26 [QC-ACN-AA-XB] |
| 196 | 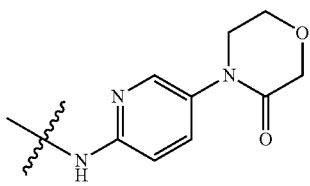 [SMILES: *Nc1ccc(N2CCOCC2=O)cn1] | 515.56 | 516.4 | 1.09 [QC-ACN-AA-XB] |
| 197 | 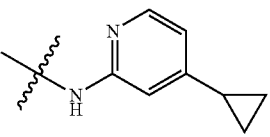 [SMILES: *Nc1cc(C2CC2)ccn1] | 456.53 | 458.5 | 1.62 [QC-ACN-AA-XB] |

TABLE 8-continued

| Example No. | NR²R⁵ | MW | m/z [M + H]⁺ | Rt (min) [Method] |
|---|---|---|---|---|
| 198 | 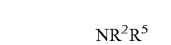 | 435.51 | 436.2 | 1.63 [QC-ACN-AA-XB] |

Example 199

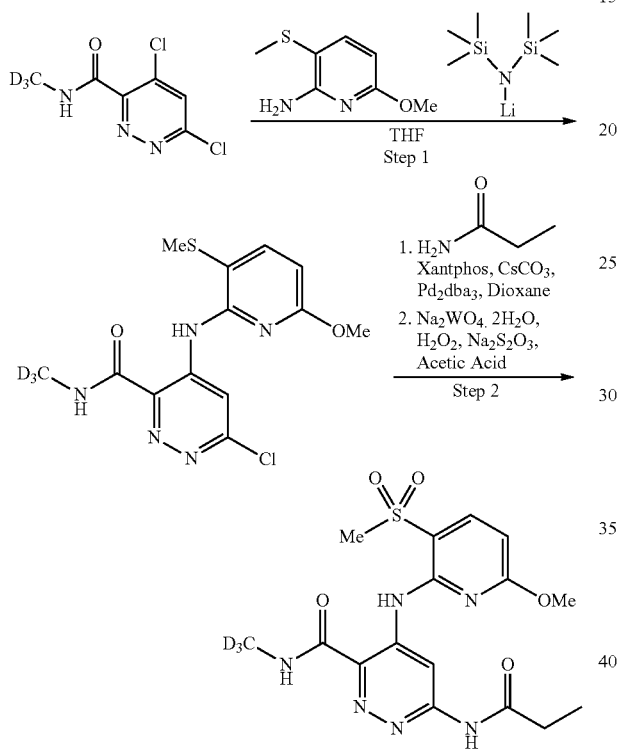

Step 1

To a solution of 4,6-dichloro-N-(methyl-d3)pyridazine-3-carboxamide (491 mg, 2.350 mmol) and 6-methoxy-3-(methylthio)pyridin-2-amine (400 mg, 2.35 mmol) in THF (5 mL) at rt was added lithium bis(trimethylsilyl)amide in THF (5.87 mL, 5.87 mmol) over 5 min. The resulting mixture was stirred at rt for overnight. The reaction was quenched with 1N HCl (1.5 mL) and water was added (20 mL). The mixture was extracted with DCM (3×20 mL) and the combined organic layers dried over Na₂SO₄ and concentrated under vacuum to provide the product 6-chloro-4-((6-methoxy-3-(methylthio)pyridin-2-yl)amino)-N-(methyl-d3)pyridazine-3-carboxamide (600 mg, 1.75 mmol, 74.5% yield). Material used in next step as is.

MS (M+1) m/z: 343.3 (MH⁺). LC retention time 1.19 min [C].

Step 2

A mixture of 6-chloro-4-((6-methoxy-3-(methylthio)pyridin-2-yl)amino)-N-(methyl-d3)pyridazine-3-carboxamide (35 mg, 0.102 mmol), propionamide (11.19 mg, 0.153 mmol), Xantphos (8.86 mg, 0.015 mmol), Pd₂(dba)₃ (7.01 mg, 7.66 μmol) and Cs₂CO₃ (66.5 mg, 0.204 mmol) in dioxane (0.7 mL) was purged with nitrogen for 2 min, then stirred at 130° C. for 3 h. The mixture was mixed with MeOH/DCM (1:1, 5 mL), filtered and the filtrate was concentrated and the residue was used in next step. The residue was mixed with AcOH (1 mL) and sodium tungstate dihydrate (10.10 mg, 0.031 mmol) was added. Hydrogen peroxide (313 μl, 3.06 mmol) was added and the mixture was stirred at rt for 1 h. To the mixture was added sodium thiosulfate (484 mg, 3.06 mmol) and it was stirred for 10 min. The mixture was filtered and purified by prep HPLC to provide 4-((6-methoxy-3-(methylsulfonyl)pyridin-2-yl)amino)-N-(methyl-d3)-6-propionamidopyridazine-3-carboxamide (13.0 mg, 0.031 mmol, 30.95% yield).

MS (M+1) m/z: 412.4 (M+H⁺). LC retention time 1.26 min [QC-ACN-TFA-XB].

¹H NMR (500 MHz, DMSO-d₆) δ 12.13-11.98 (m, 1H), 11.23-11.02 (m, 1H), 9.44-9.29 (m, 1H), 9.24-9.12 (m, 1H), 8.19-8.07 (m, 1H), 6.79-6.57 (m, 1H), 4.03-3.90 (m, 3H), 3.48-3.39 (m, 3H), 2.49-2.44 (q, 2H), 1.08 (s, 3H).

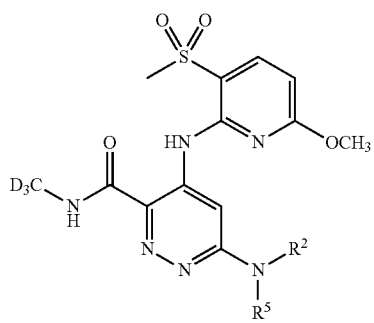

The following examples were prepared in a similar manner to the product of Example 199.

TABLE 9

| Example No. | NR²R⁵ | MW | m/z [M + H]⁺ | Rt (min) [Method] |
|---|---|---|---|---|
| 200 | ![structure] | 423.5 | 424.4 | 1.4 [QC-ACN-AA-XB] |
| 201 | ![structure] | 490.6 | 491.4 | 1.3 [QC-ACN-AA-XB] |

TABLE 9-continued

| Example No. | NR²R⁵ | MW | m/z [M + H]⁺ | Rt (min) [Method] |
|---|---|---|---|---|
| 202 | | 525 | 525.1 | 1.6 [QC-ACN-AA-XB] |
| 203 | | 517.6 | 518.2 | 1.3 [QC-ACN-AA-XB] |
| 204 | | 435.5 | 436 | 1.3 [QC-ACN-AA-XB] |
| 205 | | 472.5 | 473.1 | 1.4 [QC-ACN-AA-XB] |
| 206 | | 516.5 | 517.4 | 1.9 [QC-ACN-AA-XB] |

Example 207

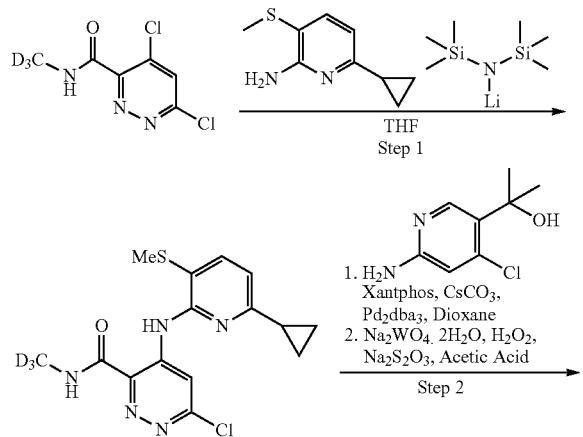

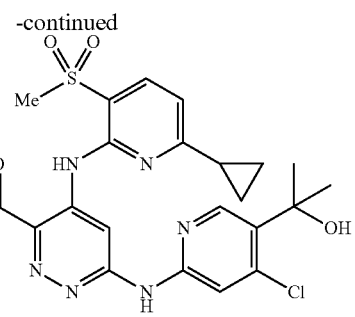

Step 1

To a solution of 4,6-dichloro-N-trideuteromethylpyridazine-3-carboxamide (209 mg, 0.999 mmol) and 6-cyclopropyl-3-(methylthio)pyridin-2-amine (180 mg, 0.999 mmol) in THF (10 mL) at rt was added lithium bis(trimethylsilyl)amide in THF (2.496 mL, 2.496 mmol) over 5 min. The resulting mixture was stirred at rt for 1 h. The reaction was quenched with water (5 mL) and the mixture was adjusted with 1N HCl solution to pH 9-10 and further diluted with water (10 mL). The precipitating product was collected by suction filtration and dried under vacuum to give 6-chloro-4-((6-cyclopropyl-3-(methylthio)pyridin-2-yl)amino)-N-(methyl-d3)pyridazine-3-carboxamide (260 mg, 0.737 mmol, 73.8% yield) as a pale solid. MS (M+1) m/z: 353.4 (MH⁺). LC retention time 1.40 min [C]. $^1$H NMR (499 MHz, DMSO-d₆) δ 12.35-12.22 (m, 1H), 9.44-9.31 (m, 1H), 9.16-9.00 (m, 1H), 7.90-7.73 (m, 1H), 7.17-6.98 (m, 1H), 2.47-2.44 (m, 3H), 2.21-2.11 (m, 1H), 1.09-1.03 (m, 2H), 1.00-0.94 (m, 2H).

Step 2

A mixture of 6-chloro-4-((6-cyclopropyl-3-(methylthio)pyridin-2-yl)amino)-N-(methyl-d3)pyridazine-3-carboxamide (100 mg, 0.283 mmol), 2-(6-amino-4-chloropyridin-3-yl)propan-2-ol (63.5 mg, 0.340 mmol), Xantphos (24.60 mg, 0.043 mmol), Pd₂(dba)₃ (19.46 mg, 0.021 mmol) and Cs₂CO₃ (185 mg, 0.567 mmol) in dioxane (0.7 mL) was purged with nitrogen for 2 min, then stirred at 130° C. for 3 h. The resulting mixture was mixed with MeOH/DCM (1:1, 5 mL), filtered and the filtrate was concentrated and the residue used in the next step. The resulting residue was mixed with AcOH (1 mL), sodium tungstate dihydrate (28.0 mg, 0.085 mmol) and hydrogen peroxide (289 µl, 2.83 mmol). After 1 hr at rt, sodium thiosulfate (672 mg, 4.25 mmol) was added and the mixture stirred for 10 min. The mixture was filtered and purified by prep HPLC to provide the product, 4-((6-cyclopropyl-3-(methylsulfonyl)pyridin-2-yl)amino)-6-((4-(2-hydroxypropan-2-yl)phenyl)amino)-N-(methyl-d3)pyridazine-3-carboxamide (8.3 mg, 0.015 mmol, 5.42% yield).

MS (M+1) m/z: 535.4 (M+H⁺). LC retention time 1.65 min [QC-ACN-AA-XB].

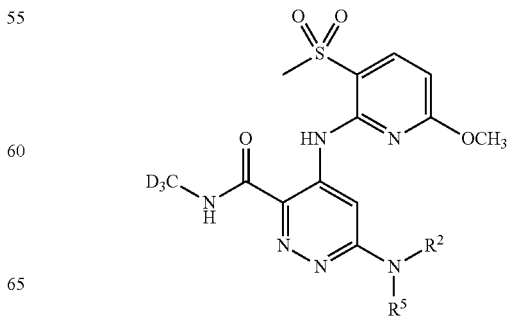

The following example was prepared in a similar manner to the product of Example 207.

TABLE 10

| Example No. | NR²R⁵ | MW | m/z [M + H]⁺ | Rt (min) [Method] |
|---|---|---|---|---|
| 208 | 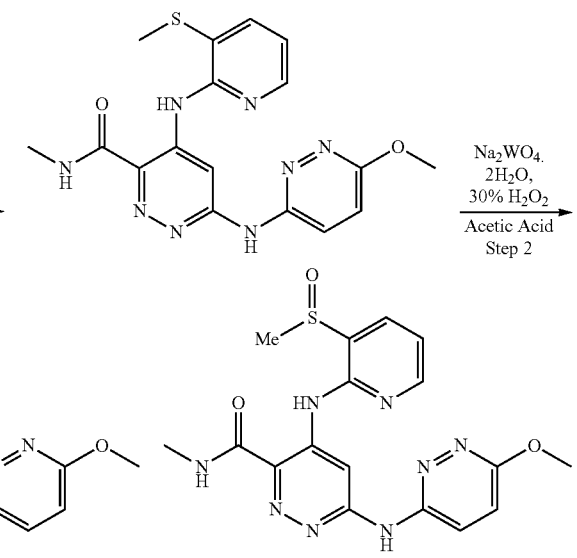 | 500.59 | 501.5 | 1.39 [QC-ACN-AA-XB] |

Example 209

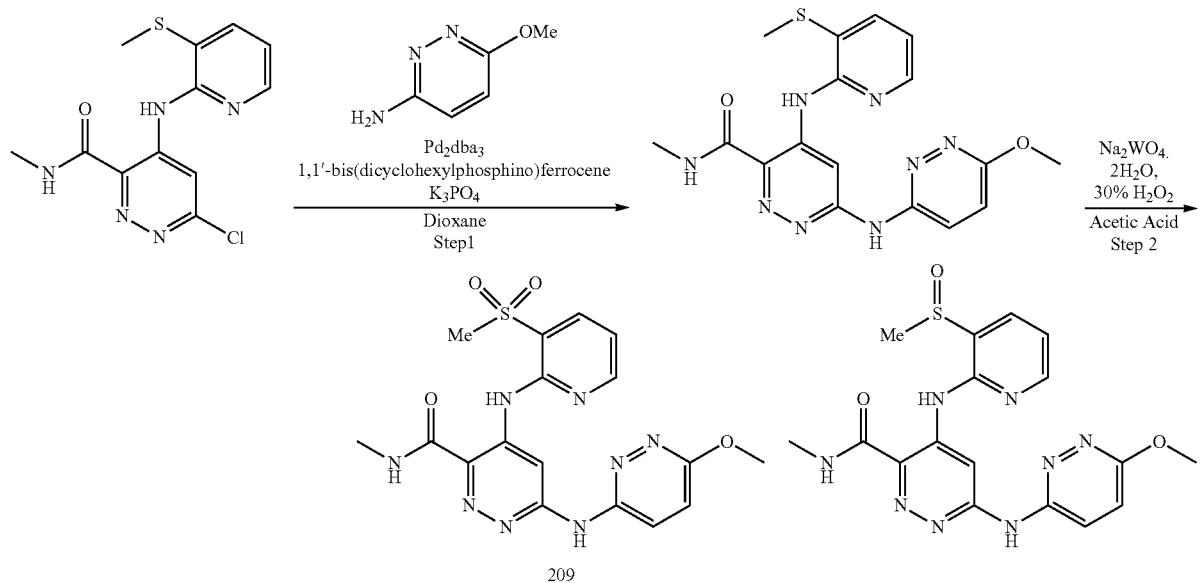

Step 1

A suspension of tris(dibenzylideneacetone)dipalladium (0) (7.40 mg, 8.09 μmol), 1,1'-bis(dicyclohexylphosphino)ferrocene (9.36 mg, 0.016 mmol), 6-chloro-N-methyl-4-((3-(methylthio)pyridin-2-yl)amino)pyridazine-3-carboxamide (0.1002 g, 0.323 mmol), 6-methoxypyridazin-3-amine (0.081 g, 0.647 mmol) and potassium phosphate tribasic (0.404 ml, 0.809 mmol) in 1,4-dioxane (2.5 mL) in a 1 dram vial underwent a vacuum/N2 cycle three times. The reaction mixture was heated at 80° C. for 3 hours then diluted with water and filtered. The solid was washed with water and dried under vacuum overnight to give crude 6-((6-methoxypyridazin-3-yl)amino)-N-methyl-4-((3-(methylthio)pyridin-2-yl)amino)pyridazine-3-carboxamide (0.119 g, 0.299 mmol, 92% yield). 14 mg of the crude was purified with prep HPLC to give a pure product, 6-((6-methoxypyridazin-3-yl)amino)-N-methyl-4-((3-(methylthio)pyridin-2-yl)amino)pyridazine-3-carboxamide (8.5 mg, 0.021 mmol, 6.40% yield).

MS (M+1) m/z: 399.3 (MH⁺). LC retention time 1.487 min [QC-ACN-AA-XB].

1H NMR (500 MHz, DMSO-d6) δ 12.01 (s, 1H), 10.37 (s, 1H), 9.30 (s, 1H), 9.20 (br d, J=4.6 Hz, 1H), 8.21 (d, J=3.7 Hz, 1H), 8.02 (d, J=9.5 Hz, 1H), 7.83 (d, J=6.7 Hz, 1H), 7.23 (d, J=9.5 Hz, 1H), 7.09 (dd, J=7.6, 4.9 Hz, 1H), 3.99 (s, 3H), 2.86 (d, J=4.6 Hz, 3H), 2.53 (s, 3H).

Step 2

To a solution of 6-((6-methoxypyridazin-3-yl)amino)-N-methyl-4-((3-(methylthio)pyridin-2-yl)amino)pyridazine-3-carboxamide (0.1 g, 0.251 mmol) in acetic acid (15 mL) at rt was added sodium tungstate dihydrate (0.159 g, 0.482 mmol) in one portion, followed by 30% hydrogen peroxide (0.769 mL, 7.53 mmol). The solution was stirred at rt for 1 hour. To the reaction was added 0.8 mL of 30% $H_2O_2$ which was stirred at rt for 6 hours. The reaction mixture was diluted with ice water and basified with $Na_2CO_3$ powder. The aqueous layer was extracted three times with DCM, and the combined organic layers were dried ($Na_2SO_4$), filtered and concentrated. The resulting solid was dissolved in 14 mL AcOH, followed by the addition of sodium tungstate dihydrate (0.124 g) and 0.8 mL of 30% hydrogen peroxide. The reaction was stirred at room temperature for 2 hours. The reaction mixture was purified by prep HPLC to provide the product 6-((6-methoxypyridazin-3-yl)amino)-N-methyl-4-((3-(methylsulfonyl)pyridin-2-yl)amino)pyridazine-3-carboxamide (8.6 mg, 0.020 mmol, 7.96% yield).

$^1$H NMR (500 MHz, DMSO-d$_6$) δ 12.09-11.97 (m, 1H), 9.24-9.16 (m, 1H), 9.13-9.02 (m, 1H), 8.65-8.53 (m, 1H), 8.34-8.23 (m, 1H), 7.94 (s, 1H), 7.31 (br s, 1H), 7.27-7.17 (m, 1H), 4.05-3.92 (m, 3H), 3.41-3.30 (m, 3H), 2.89-2.81 (m, 3H).

This reaction also provided the side product 6-((6-methoxypyridazin-3-yl)amino)-N-methyl-4-((3-(methylsulfinyl)pyridin-2-yl)amino)pyridazine-3-carboxamide (6.6 mg, 0.016 mmol, 6.35% yield).

MS (M+1) m/z: 415.2 (MH⁺). LC retention time 0.89 min [QC-ACN-TFA-XB].

Example 210

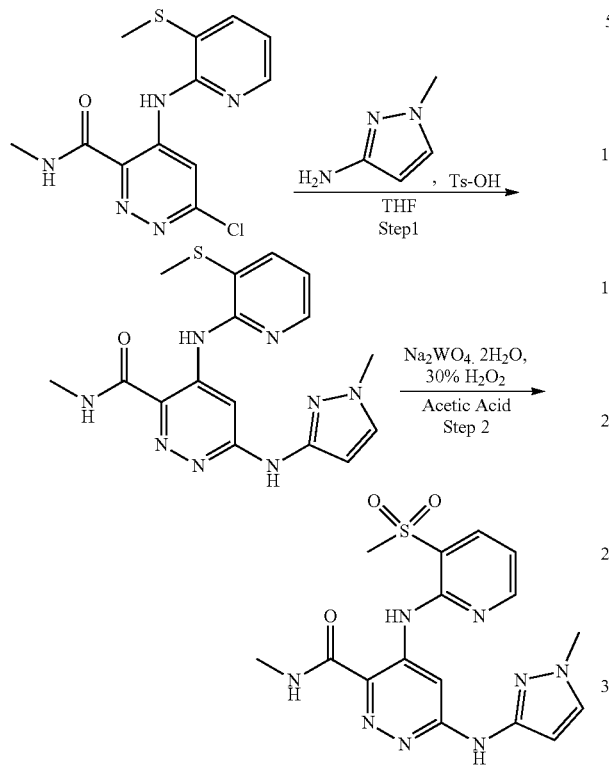

Step 1

A suspension of tosic acid (0.091 g, 0.479 mmol), 6-chloro-N-methyl-4-((3-(methylthio)pyridin-2-yl)amino) pyridazine-3-carboxamide (0.099 g, 0.320 mmol) and 1-methyl-1H-pyrazol-3-amine (0.184 g, 1.895 mmol) in THF (2 mL) was heated at 100° C. for 8 hours. The reaction was diluted with ethyl acetate, washed with 1N NaOH and water. The ethyl acetate layer was separated, dried ($Na_2SO_4$), filtered and concentrated to give crude product N-methyl-6-((1-methyl-1H-pyrazol-3-yl)amino)-4-((3-(methylthio)pyridin-2-yl)amino)pyridazine-3-carboxamide (0.1268 g, 0.342 mmol, 107% yield). A portion (23 mg) of crude product was purified by prep HPLC to provide N-methyl-6-((1-methyl-1H-pyrazol-3-yl)amino)-4-((3-(methylthio)pyridin-2-yl)amino)pyridazine-3-carboxamide (12.4 mg, 0.031 mmol, 9.85% yield).

MS (M+1) m/z: 371.2 (MH$^+$). LC retention time 1.377 min [QC-ACN-AA-XB].

$^1$H NMR (500 MHz, DMSO-d$_6$) δ 12.05-11.86 (m, 1H), 9.89-9.72 (m, 1H), 9.21-9.00 (m, 2H), 8.32-8.12 (m, 1H), 7.93-7.69 (m, 1H), 7.63-7.47 (m, 1H), 7.17-6.97 (m, 1H), 6.33-6.17 (m, 1H), 3.82-3.75 (m, 3H), 2.89-2.79 (m, 3H).

Step 2

To a solution of N-methyl-6-((1-methyl-1H-pyrazol-3-yl) amino)-4-((3-(methylthio)pyridin-2-yl)amino)pyridazine-3-carboxamide (0.1158 g, 0.313 mmol) in acetic acid (15 mL) at rt was added sodium tungstate dihydrate (0.129 g, 0.391 mmol) in one portion, followed by 30% hydrogen peroxide (0.958 mL, 9.38 mmol). The solution was stirred at rt for 1 hour. The reaction mixture was diluted with ice water and basified with $Na_2CO_3$ powder. The aqueous layer was extracted three times with DCM. The organic layer was washed with sodium thiosulfate (5%), dried ($Na_2SO_4$), filtered and concentrated. The crude residue was purified by prep HPLC to give N-methyl-6-((1-methyl-1H-pyrazol-3-yl)amino)-4-((3-(methylsulfonyl)pyridin-2-yl)amino) pyridazine-3-carboxamide (56 mg, 0.138 mmol, 44.1% yield).

MS (M+1) m/z: 402.9 (MH$^+$). LC retention time 0.817 min [QC-ACN-TFA-XB].

1H NMR (400 MHz, DMSO-d6) δ 12.08 (s, 1H), 9.94 (s, 1H), 9.12 (br d, J=4.6 Hz, 1H), 9.06 (s, 1H), 8.65 (dd, J=4.8, 1.8 Hz, 1H), 8.28 (dd, J=7.8, 1.8 Hz, 1H), 7.59 (d, J=2.2 Hz, 1H), 7.30 (dd, J=7.8, 4.8 Hz, 1H), 6.28 (d, J=2.1 Hz, 1H), 3.79 (s, 3H), 3.38 (s, 3H), 2.85 (d, J=4.8 Hz, 3H).

Example 211

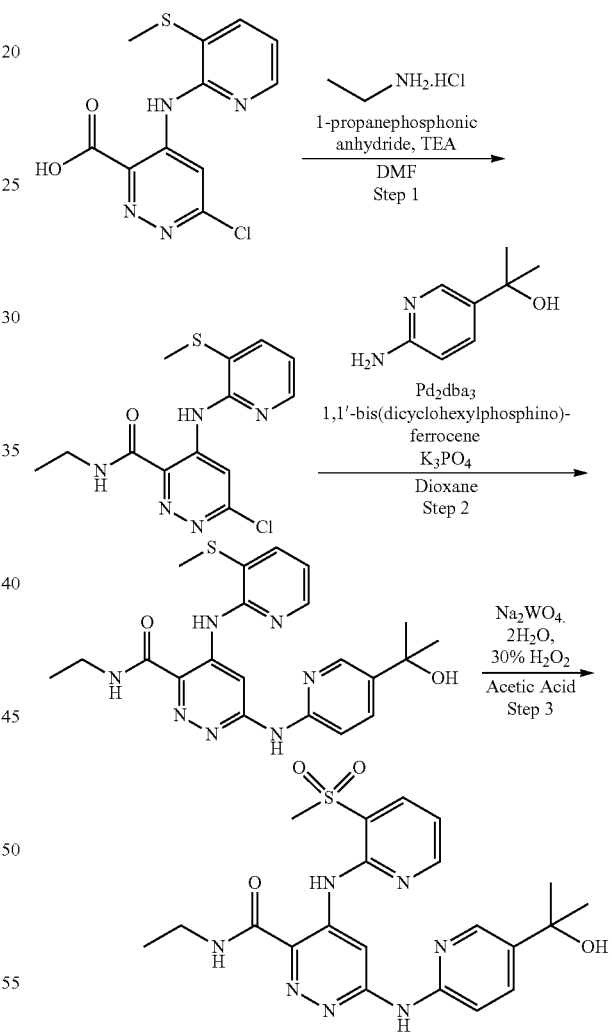

Step 1

1-propanephosphonic anhydride (0.698 mL, 1.196 mmol) was added to a DMF (2.5 mL) solution of 6-chloro-4-((3-(methylthio)pyridin-2-yl)amino)pyridazine-3-carboxylic acid (0.2365 g, 0.797 mmol) and TEA (0.222 ml, 1.594 mmol) at rt. The reaction was stirred at room temperature for 1 hour before addition of ethanamine hydrochloride (0.3383 g, 4.15 mmol) and TEA (0.2 mL). The reaction was stirred for 16 hours at rt, diluted with water and the suspension was filtered and washed with water. The solid was dried under vacuum overnight. The crude product was purified with silica gel flash chromatography (ISCO, 12 g column) and eluted with ethyl acetate in hexane from 0 to 50% to give the desired product 6-chloro-N-ethyl-4-((3-(methylthio)pyridin-2-yl)amino)pyridazine-3-carboxamide (102 mg, 0.315 mmol, 39.6% yield).

MS (M+1) m/z: 324.0 (MH$^1$). LC retention time 0.97 min [A].

$^1$H NMR (400 MHz, CHLOROFORM-d) δ 12.59-12.44 (m, 1H), 9.33-9.27 (m, 1H), 8.57-8.51 (m, 1H), 8.45-8.31 (m, 2H), 7.39-7.31 (m, 1H), 3.67-3.49 (m, 2H), 3.06-2.79 (m, 3H), 1.39-1.27 (m, 3H).

Step 2

A suspension of tris(dibenzylideneacetone)dipalladium (0) (2.262 mg, 2.471 μmol), 1,1'-bis(dicyclohexylphosphino)ferrocene (2.86 mg, 4.94 μmol), 6-chloro-N-ethyl-4-((3-(methylthio)pyridin-2-yl)amino)pyridazine-3-carboxamide (0.0320 g, 0.099 mmol), 2-(6-aminopyridin-3-yl)propan-2-ol (0.0182 g, 0.120 mmol) and potassium phosphate, tribasic (0.124 mL, 0.247 mmol) in 1,4-dioxane (0.5 mL) in a 1 dram vial underwent a vacuum/N2 cycle three times. The reaction mixture was heated at 80° C. for 3 hours. The reaction was diluted with ethyl acetate and was washed with water three times. The ethyl acetate layer was separated, dried (Na$_2$SO$_4$), filtered and concentrated. The crude product, N-ethyl-6-((5-(2-hydroxypropan-2-yl)pyridin-2-yl)amino)-4-((3-(methylthio)pyridin-2-yl)amino)pyridazine-3-carboxamide (41.3 mg, 0.094 mmol, 95% yield) was obtained. The crude product was used as is in next step.

MS (M−1) m/z: 438.4 (M$^+$). LC retention time 0.89 min [E].

Step 3

To a solution of N-ethyl-6-((5-(2-hydroxypropan-2-yl)pyridin-2-yl)amino)-4-((3-(methylthio)pyridin-2-yl)amino)pyridazine-3-carboxamide (0.0412 g, 0.094 mmol) in acetic acid (3 mL) at rt was added sodium tungstate dihydrate (0.039 g, 0.117 mmol) in one portion, followed by 30% hydrogen peroxide (0.287 mL, 2.81 mmol). The solution was stirred at rt for 1 hour. 0.3 mL 30% H$_2$O$_2$ was added and the reaction was stirred for another 1 hour. This was repeated 3 more times. The reaction mixture was diluted with ice water and basified with Na$_2$CO$_3$ powder. The aqueous layer was extracted three times with DCM. The DCM layer was washed with sodium thiosulfate (5%) one time, dried (Na$_2$SO$_4$), filtered and concentrated. The crude was purified with prep HPLC to provide the desired product, N-ethyl-6-((5-(2-hydroxypropan-2-yl)pyridin-2-yl)amino)-4-((3-(methylsulfonyl)pyridin-2-yl)amino)pyridazine-3-carboxamide (12.3 mg, 0.026 mmol, 27.8% yield).

MS (M+1) m/z: 472.1 (M$^+$). LC retention time 1.299 min [QC-ACN-AA-XB].

$^1$H NMR (500 MHz, DMSO-d$_6$) δ 12.16-11.97 (m, 1H), 10.33-10.17 (m, 1H), 9.53-9.37 (m, 1H), 9.30-9.08 (m, 1H), 8.72-8.60 (m, 1H), 8.43-8.33 (m, 1H), 8.32-8.22 (m, 1H), 7.85-7.75 (m, 1H), 7.70-7.60 (m, 1H), 7.37-7.29 (m, 1H), 2.56-2.54 (m, 5H), 1.51-1.43 (m, 6H), 1.21-1.13 (m, 3H).

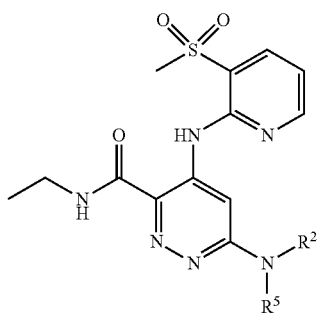

The following example was prepared in a similar manner to the product of Example 211.

TABLE 11

| Example No. | NR$^2$R$^5$ | MW | m/z [M + H]$^+$ | Rt (min) [Method] |
|---|---|---|---|---|
| 212 | | 468.53 | 469.1 | 1.71 [QC-ACN-AA-XB] |

Example 213

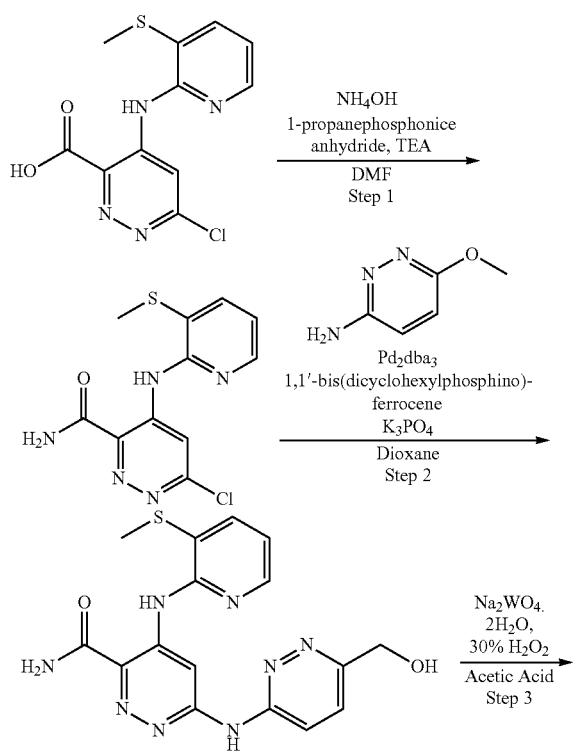

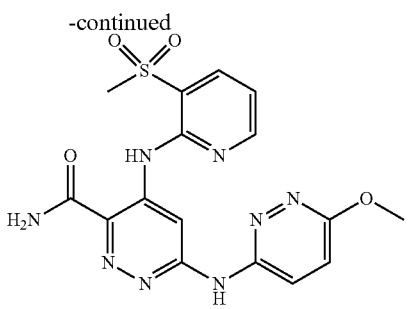

Step 1

1-propanephosphonic anhydride (0.416 mL, 0.712 mmol) was added to a DMF (2 mL) solution of 6-chloro-4-((3-(methylthio)pyridin-2-yl)amino)pyridazine-3-carboxylic acid (0.1408 g, 0.475 mmol) and TEA (0.132 mL, 0.949 mmol) at rt. The reaction was diluted with diethyl ether and filtered. The solid was collected as a gummy brown solid. The rest of the material (filtrate) was combined, concentrated and treated with NH$_4$OH overnight. The gummy brown solid was suspended in 1 mL of DMSO and NH$_4$OH (2 mL) was added. The suspension was stirred vigorously. After 1 hour, the mixture showed complete conversion to the primary amide. All of the above were combined, diluted with ethyl acetate and washed with water three times. The ethyl acetate layer was separated, dried (Na$_2$SO$_4$), filtered and concentrated. The crude product, 6-chloro-4-((3-(methylthio)pyridin-2-yl)amino)pyridazine-3-carboxamide (97.4 mg, 0.329 mmol, 69.4% yield), was used as is in the next step.

MS (M+1) m/z: 296.1 (MH$^{3o}$). LC retention time 0.86 min [E].

Step 2

A suspension of tris(dibenzylideneacetone)dipalladium (0) (7.54 mg, 8.23 μmol), 1,1'-bis(dicyclohexylphosphino)ferrocene (9.53 mg, 0.016 mmol), 6-chloro-4-((3-(methylthio)pyridin-2-yl)amino)pyridazine-3-carboxamide (0.0974 g, 0.329 mmol), 6-methoxypyridazin-3-amine (0.082 g, 0.659 mmol) and potassium phosphate, tribasic (0.412 ml, 0.823 mmol) in 1,4-dioxane (2.5 mL) in a 1 dram vial underwent a vacuum/N$_2$ cycle three times. The reaction mixture was heated at 80° C. for 3 hours. During the heating, the reaction mixture became a clear solution. The reaction mixture was diluted with ethyl acetate and washed with water three times. The ethyl acetate layer was separated, dried (Na$_2$SO$_4$), filtered and concentrated to give a crude product.

MS (M+1) m/z: 385.2 (MH$^+$). LC retention time 0.76 min [E].

1H NMR (400 MHz, CHLOROFORM-d) δ 12.09 (s, 1H), 9.15 (s, 1H), 8.33 (d, J=9.5 Hz, 1H), 8.30 (dd, J=4.9, 1.7 Hz, 1H), 8.09 (br d, J=2.9 Hz, 1H), 7.90 (s, 1H), 7.78 (dd, J=7.6, 1.7 Hz, 1H), 7.06 (d, J=9.4 Hz, 1H), 6.98 (dd, J=7.6, 4.9 Hz, 1H), 5.55 (br d, J=3.2 Hz, 1H), 4.13 (s, 3H), 2.52 (s, 3H).

Step 3

To a solution of 6-((6-methoxypyridazin-3-yl)amino)-4-((3-(methylthio)pyridin-2-yl)amino)pyridazine-3-carboxamide (0.0329 g, 0.086 mmol) in acetic acid (3 mL) at rt was added sodium tungstate dihydrate (0.035 g, 0.107 mmol) in one portion, followed by 30% hydrogen peroxide (0.262 mL, 2.57 mmol). The solution was stirred at rt. for 20 min and a suspension was observed. The reaction was stirred at room temperature for 3 hours. The reaction was diluted with water (50 mL) and basified with Na$_2$CO$_3$ powder. The aqueous layer was extracted with DCM three times. The DCM layer was combined, dried (Na$_2$SO$_4$), filtered and concentrated to give the crude product. The crude product was purified with prep HPLC to provide the desired product, 6-((6-methoxypyridazin-3-yl)amino)-4-((3-(methylsulfonyl)pyridin-2-yl)amino)pyridazine-3-carboxamide (2.6 mg, 6.24 μmol, 7.30% yield).

MS (M+1) m/z: 417.3 (MH$^+$). LC retention time 0.907 min [QC-ACN-TFA-XB].

$^1$H NMR (500 MHz, DMSO-d$_6$) δ 12.23-12.14 (m, 1H), 10.54-10.39 (m, 1H), 9.33-9.17 (m, 1H), 8.65-8.61 (m, 1H), 8.59-8.53 (m, 1H), 8.31-8.26 (m, 1H), 8.07-8.01 (m, 1H), 7.88-7.83 (m, 1H), 7.37-7.31 (m, 1H), 7.27-7.23 (m, 1H), 4.02-3.95 (m, 3H).

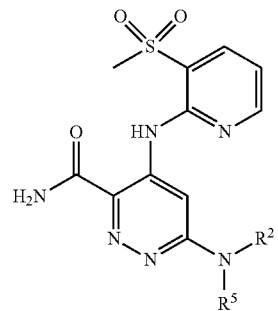

The following example was prepared in a similar manner to the product of Example 213.

TABLE 12

| Example No. | NR$^2$R$^5$ | MW | m/z [M + H]$^+$ | Rt (min) [Method] |
|---|---|---|---|---|
| 214 | | 388.4 | 389.2 | 0.766 [QC-ACN-TFA-XB] |

Example 215

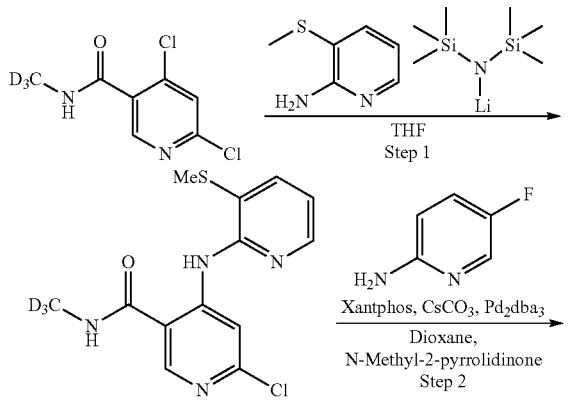

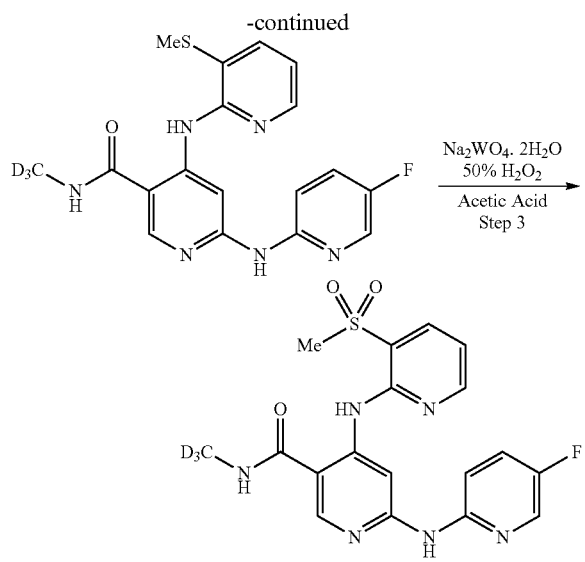

Step 1

To a solution of 4,6-dichloro-N-(methyl-d3)nicotinamide (30 mg, 0.144 mmol) and 3-(methylthio)pyridin-2-amine (22.24 mg, 0.159 mmol) in THF (5 mL) at rt was added lithium bis(trimethylsilyl)amide in THF (0.360 mL, 0.360 mmol) over 5 min. The resulting mixture was stirred at rt overnight. The reaction was quenched with 1N HCl (1.5 mL) and water was added (20 mL). The mixture was extracted with DCM (3×20 mL) which was combined, dried (Na$_2$SO$_4$) and concentrated under vacuum and used as is in the next step.

MS (M+1) m/z: 312.2 (MH$^+$). LC retention time 1.06 min [C].

Step 2

A solution of 6-chloro-N-(methyl-d3)-4-((3-(methylthio)pyridin-2-yl)amino)nicotinamide (0.13 g, 0.412 mmol), 5-fluoropyridin-2-amine (0.104 g, 0.928 mmol), Xantphos (0.046 g, 0.080 mmol), cesium carbonate (0.352 g, 1.081 mmol) and Pd$_2$dba$_3$ (0.072 g, 0.079 mmol) in dioxane (10 ml) and N-Methyl-2-pyrrolidinone (2.00 mL) in a sealed vial was microwaved to 150° C. for 1 h. Once the reaction was completed, the reaction mixture was diluted with ethyl acetate (10 mL) and filtered through Celite. The filtrate was concentrated in vacuo. DMSO (3 mL) and water (45 mL), followed by saturated NaHCO3 (4 mL), were added to the residue. The precipitate was collected, filtered and washed with water to give crude product as an orange solid. The crude product (readily soluble in THF) was purified by flash chromatography using an ISCO 40 g column (solid loading) eluting with 0-10% MeOH/DCM (0%, 1 cv; 0-5%, 20 cv; 5-10%, 8 cv). Appropriate fractions (5.0-7.5% elution) were collected and concentrated in vacuo to give 6-((5-fluoropyridin-2-yl)amino)-N-(methyl-d3)-4-((3-(methylthio)pyridin-2-yl)amino)nicotinamide (0.0367 g, 0.095 mmol, 22.97% yield) as a light yellow solid.

MS (M+1) m/z: 388.1 (M$^1$). LC retention time 0.70 min [F].

Step 3

To 6-((5-fluoropyridin-2-yl)amino)-N-(methyl-d3)-4-((3-(methylthio)pyridin-2-yl)amino)nicotinamide (0.0367 g, 0.095 mmol) was added acetic acid (3 mL) to give a heterogeneous solution. The solution was warmed slightly and turned homogeneous. After cooling to rt, sodium tungstate dihydrate (0.0411 g, 0.125 mmol) was added, followed by 50% hydrogen peroxide (0.2 mL, 3.47 mmol). Within 1 min, the solution turned heterogeneous. After 0.5 h, the starting material was consumed. The reaction mixture was stirred for another 1 h to achieve complete oxidation. Water (25 mL) was added to the reaction, followed by sodium carbonate until pH was shown to be basic by litmus paper. The mixture was extracted with DCM (4×50 mL). The organic layers were combined, dried over Na$_2$SO$_4$ and filtered. Silica gel was added to the filtrate and concentrated in vacuo. The crude product was purified by flash chromatography (solid loading) using an ISCO 24 g column eluting with 0-5% MeOH/DCM (0%, 1 cv; 0-5%, 15 cv; 5%, 5 cv). Appropriate fractions (4.5-5.0%) were collected and concentrated in vacuo to give the desired product. MeOH was added and the triturated material was washed with MeOH and dried in a desiccator oven at 55° C. to give 6-((5-fluoropyridin-2-yl)amino)-N-(methyl-d3)-4-((3-(methylsulfonyl)pyridin-2-yl)amino)nicotinamide (0.012 g, 0.029 mmol, 30.3% yield).

MS (M+1) m/z: 420.1 (MH$^+$). LC retention time 0.59 min [B].

$^1$H NMR (400 MHz, DMSO-d$_6$) δ 11.56-11.47 (m, 1H), 10.02-9.85 (m, 1H), 8.89-8.78 (m, 1H), 8.70-8.59 (m, 1H), 8.57-8.50 (m, 2H), 8.26-8.20 (m, 2H), 7.83-7.74 (m, 1H), 7.71-7.58 (m, 1H), 7.28-7.20 (m, 1H), 3.39-3.34 (m, 3H).

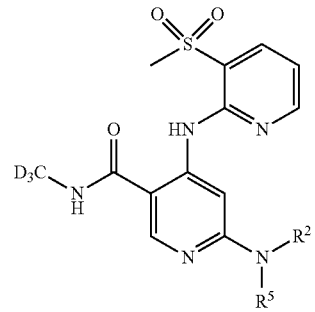

The following Examples were prepared in a similar manner to the product of Example 215

TABLE 13

| Example No. | NR$^2$R$^5$ | MW | m/z [M + H]$^+$ | Rt (min) [Method] |
|---|---|---|---|---|
| 216 | ![structure] | 401.45 | 402.1 | 0.56 [B] |
| 217 | ![structure with Cl] | 435.90 | 436.0 | 0.62 [A] |
| 218 | ![structure with F] | 433.47 | 434.1 | 0.62 [A] |

TABLE 13-continued

| Example No. | NR²R⁵ | MW | m/z [M + H]⁺ | Rt (min) [Method] |
|---|---|---|---|---|
| 219 | pyridine-CF₃ | 469.46 | 470.2 | 0.67 [F] |
| 220 | pyridine-CN | 426.47 | 427.0 | 0.59 [B] |
| 221 | pyridine-CN | 426.47 | 427.0 | 0.65 [F] |
| 222 | pyrazine-cyclopropyl | 442.51 | 443.0 | 0.63 [A] |
| 223 | pyridazine-CF₃ | 470.44 | 471.2 | 1.47 [QC-ACN-AA-XB] |
| 224 | pyridazine | 402.44 | 403.1 | 0.86 [QC-ACN-AA-XB] |
| 225 | pyrimidine-CF₃ | 470.44 | 471.2 | 0.65 [B] |
| 226 | pyrimidine-tBu | 430.46 | 431.1 | 0.68 [A] |
| 227 | pyrimidine-cyclopropyl | 458.55 | 459.0 | 0.64 [A] |
| 228 | pyrimidine-dicyclopropyl | 482.57 | 482.8 | 0.64 [A] |
| 229 | pyrimidine-Me-cyclopropyl | 456.5 | 457.08 | 0.59 [A] |
| 230 | pyridine-Me-CN | 440.5 | 440.8 | 0.61 [A] |
| 231 | pyridine-CN-CF₃ | 494.5 | 495.2 | 0.75 [B] |
| 232 | pyridine-CF₃-CN | 494.5 | 495.2 | 0.77 [F] |
| 233 | pyridine-CN-Me | 440.5 | 440.8 | 0.60 [A] |

Example 234

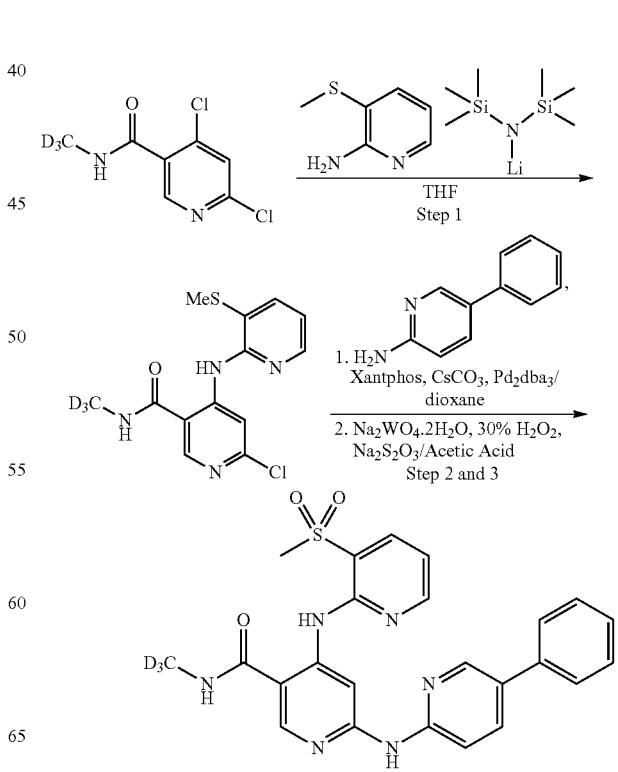

Step 1
Follow the procedure from preparation 3, example 1 step 1.

Step 2
A mixture of 6-chloro-N-(methyl-d3)-4-((3-(methylthio)pyridin-2-yl)amino)nicotinamide (25 mg, 0.080 mmol), 5-phenylpyridin-2-amine (17.74 mg, 0.104 mmol), Pd$_2$(dba)$_3$ (7.34 mg, 8.02 μmol), Xantphos (9.28 mg, 0.016 mmol), Cs$_2$CO$_3$ (34.0 mg, 0.104 mmol) in dioxane (1.0 mL) was purged with nitrogen for 5 min., and the reaction was placed into a preheated 130° C. heating block for 2 h to give N-(methyl-d3)-4-((3-(methylthio)pyridin-2-yl)amino)-6-((5-phenylpyridin-2-yl)amino)nicotinamide (M+H=446). The solution was diluted with AcOH (2 mL) and passed through a filter. To the solution was added sodium tungstate dihydrate (7.93 mg, 0.024 mmol), 30% hydrogen peroxide (164 μl, 1.604 mmol) and stirred at rt for 1 h. To the mixture was added sodium thiosulfate (254 mg, 1.604 mmol) at 0° C. and reaction mixture was stirred at rt for 10 min. The solid was filtered off and the solvent was removed in vacuo to give the impure desired product. The reaction mixture was diluted with DMSO, filtered and purified with prep HPLC to provide N-(methyl-d3)-4-((3-(methylsulfonyl)pyridin-2-yl)amino)-6-((5-phenylpyridin-2-yl)amino)nicotinamide (3.5 mg, 7.33 μmol, 9.14% yield).

MS (M+1) m/z: 478.2 (MH$^+$). LC retention time 1.72 min [QC-ACN-AA-XB].

$^1$H NMR (500 MHz, DMSO-d$_6$) δ 10.09-9.93 (m, 1H), 9.04-8.92 (m, 1H), 8.73-8.63 (m, 1H), 8.61-8.50 (m, 3H), 8.28-8.18 (m, 1H), 8.07-7.96 (m, 1H), 7.85-7.73 (m, 1H), 7.73-7.65 (m, 2H), 7.53-7.43 (m, 2H), 7.41-7.32 (m, 1H), 7.29-7.18 (m, 1H).

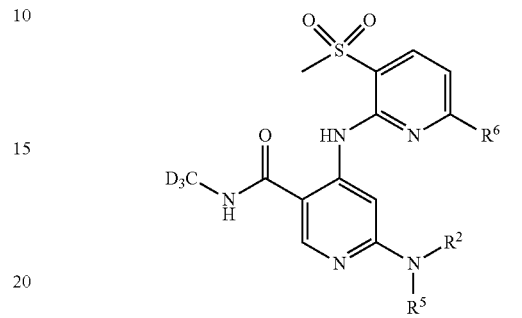

The following examples were prepared in a similar manner to the product of Example 234.

TABLE 14

| Example No. | NR$^2$R$^5$ | R$^6$ | MW | m/z [M + H]$^+$ | Rt (min) [Method] |
|---|---|---|---|---|---|
| 235 | (N-propionyl) | H | 380.4 | 381 | 1 [QC-ACN-AA-XB] |
| 236 | (N-cyclopropylcarbonyl) | H | 392.5 | 393.1 | 1.5 [QC-ACN-AA-XB] |
| 237 | (N-methoxycarbonyl) | H | 382.4 | 382.7 | 0.7 [QC-ACN-TFA-XB] |
| 238 | (N-(6-phenylpyridin-2-yl)) | H | 477.6 | 477.9 | 1.7 [QC-ACN-AA-XB] |
| 239 | (N-cyclobutylcarbonyl) | H | 406.5 | 407.1 | 1.2 [QC-ACN-AA-XB] |
| 240 | (N-(5-(trifluoromethoxy)pyridin-2-yl)) | H | 485.5 | 486.1 | 1.2 [QC-ACN-TFA-XB] |
| 241 | (N-propionyl) | (isopropyl) | 394.5 | 395 | 1.2 [QC-ACN-AA-XB] |

TABLE 14-continued

| Example No. | NR²R⁵ | R⁶ | MW | m/z [M + H]⁺ | Rt (min) [Method] |
|---|---|---|---|---|---|
| 242 | | | 406.5 | 407.1 | 1.2 [QC-ACN-AA-XB] |
| 243 | | | 434.5 | 435.3 | 1.5 [QC-ACN-AA-XB] |
| 244 | | | 409.5 | 410.1 | 1.1 [QC-ACN-AA-XB] |

Example 245

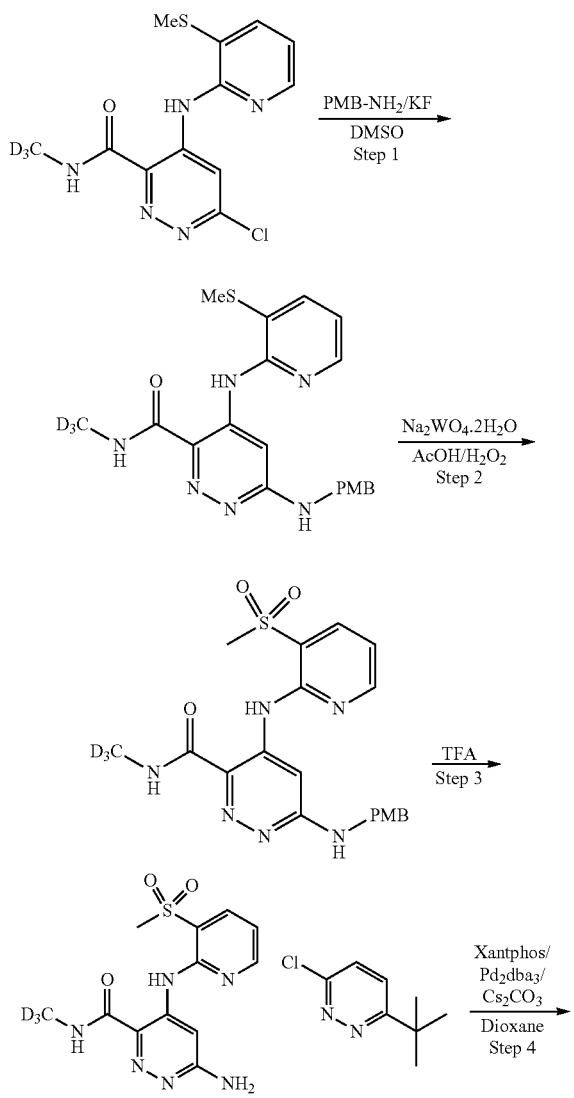

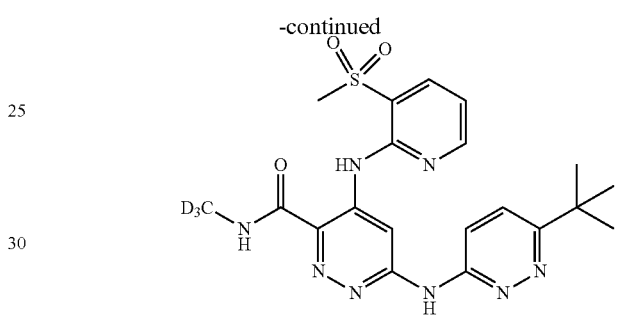

Step 1

4-Methoxybenzylamine (4.95 ml, 37.9 mmol), 6-chloro-N-(methyl-d3)-4-((3-(methylthio)pyridin-2-yl)amino) pyridazine-3-carboxamide (2.370 g, 7.58 mmol) and potassium fluoride (1.321 g, 22.74 mmol) were combined in DMSO (20 ml) and heated to 120° C. for 6 hours. The reaction was then cooled to rt, diluted with EtOAc, and washed with basic aqueous buffer (1.5 M $K_3PO_4$), water, saturated aq. ammonium chloride and brine. The aqueous layer was back extracted once with EtOAc and the organic layers were combined. The organic layer was subsequently dried over sodium sulfate, filtered, concentrated. The product 6-((4-methoxybenzypamino-N-(methyl-d3)-4-((3-(methylthio)pyridin-2-yl)amino)pyridazine-3-carboxamide was purified via automated flash chromatography eluting with methanol in DCM from 0 to 10%. (2.78 g, 89% yield).

MS (M+1) m/z: 414.3 (M⁺). LC retention time 0.75 min [D]. ¹H NMR (400 MHz, CHLOROFORM-d) δ 12.11-12.04 (m, 1H), 8.44-8.40 (m, 1H), 8.28-8.22 (m, 1H), 8.19-8.12 (m, 1H), 7.73-7.66 (m, 1H), 7.39-7.33 (m, 2H), 6.95-6.86 (m, 3H), 5.31-5.25 (m, 1H), 4.62-4.57 (m, 2H), 3.82 (s, 3H), 2.53-2.48 (m, 3H).

Step 2

Sodium tungstate dihydrate (0.831 g, 2.52 mmol) was added to an AcOH (20 mL) suspension of hydrogen peroxide (30% solution in water, 5.14 mL, 50.4 mmol) and 6-((4-methoxybenzypamino)-N-(methyl-d3)-4-((3-(methylthio)pyridin-2-yl)amino)pyridazine-3-carboxamide (1.041 g, 2.52 mmol) at room temperature. After stirring at room temperature for 1 hour, the reaction was diluted with water, basified with $Na_2CO_3$ powder and extracted three times with ethyl acetate. The ethyl acetate layer was combined, washed twice with 1.5 M $K_2HPO_4$ solution and once with $Na_2S_2O_3$ (5% solution). The organic layer was dried (Na$_2$SO$_4$), filtered and concentrated. The product 6-((4-methoxybenzy-pamino-N-(methyl-d3)-4-((3-(methylsulfonyl)pyridin-2-yl)amino)pyridazine-3-carboxamide was purified by automated flash chromatography eluting with methanol in DCM from 0 to 10% (0.66 g, 59%). MS (M+1) m/z: 446.1 (MH$^+$). LC retention time 0.66 min [D].

Step 3

A mixture of TFA (4 ml, 51.9 mmol), 6-((4-methoxybenzyl)amino)-N-(methyl-d3)-4-((3-(methylsulfonyl)pyridin-2-yl)amino)pyridazine-3-carboxamide (0.4881 g, 1.096 mmol) was heated at 60° C. for 2 hours. The solvent was removed via vacuum. To the crude was added ethyl acetate and the organic layer was washed with 1.5M K$_2$HPO$_4$ and water. The ethyl acetate layer was dried (Na$_2$SO$_4$), and filtered. The filter cake was washed with DCM to minimize loss of product. The solvent was removed in vacuo and the product was purified via automated chromatography eluting with ethyl acetate in hexane from 0 to 100%, holding 100%, and then switched to methanol in DCM from 0 to 10% to provide the product 6-amino-N-(methyl-d3)-4-((3-(methylsulfonyl)pyridin-2-yl)amino)pyridazine-3-carboxamide as a light yellow solid. (0.14 g, 40% yield). MS (M+1) m/z: 326.3 (MH$^+$). LC retention time 0.50 min [D]. $^1$H NMR (400 MHz, CHLOROFORM-d) δ 12.74-12.63 (m, 1H), 8.73-8.65 (m, 1H), 8.64-8.58 (m, 1H), 8.45-8.37 (m, 1H), 7.89-7.78 (m, 1H), 3.37-3.28 (m, 3H).

Step 4

The mixture of 3-(tert-butyl)-6-chloropyridazine (10.49 mg, 0.061 mmol), Pd$_2$(dba)$_3$ (1.407 mg, 1.537 μmol), 6-amino-N-(methyl-d3)-4-((3-(methylsulfonyl)pyridin-2-yl)amino)pyridazine-3-carboxamide (10 mg, 0.031 mmol), Xantphos (1.778 mg, 3.07 μmol), and cesium carbonate (10.01 mg, 0.031 mmol) in dioxane (0.3 mL) was degassed via a vacuum/N$_2$ fill cycle three times and then heated at 110° C. for 16 hours. The reaction was diluted with methanol, filtered and purified using reverse phase prepHPLC to give the product 6-((6-(tert-butyl)pyridazinyl-3-yl)amino)-N-(methyl-d3)-4-((3-(methylsulfonyl)pyridin-2-yl)amino)pyridazine-3-carboxamide (3.8 mg, 26% yield). MS (M+1) m/z: 460.3 (MH$^+$). LC retention time 1.17 min [E]. $^1$H NMR (500 MHz, DMSO-d$_6$) δ 12.03 (s, 1H), 10.43 (br s, 1H), 9.22 (s, 1H), 9.04 (br s, 1H), 8.61 (br d, J=4.5 Hz, 1H), 8.29 (d, J=7.8 Hz, 1H), 8.05 (d, J=9.3 Hz, 1H), 7.74 (d, J=9.3 Hz, 1H), 7.34 (dd, J=7.7, 4.8 Hz, 1H), 1.38 (s, 9H) (3H was buried below DMSO peak).

Example 246

6-((6-(difluoromethoxy)pyridazin-3-yl)amino)-N-(methyl-d3)-4-((3-(methylsulfonyl)pyridin-2-yl)amino)pyridazine-3-carboxamide

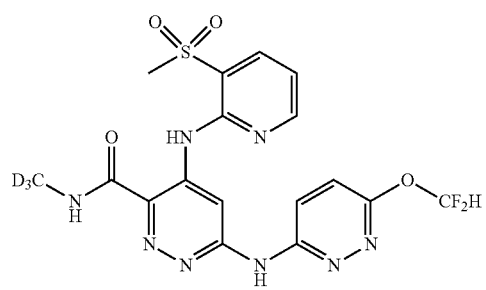 [SMILES: [2H]C([2H])([2H])NC(=O)c1nnc(Nc2ccc(OC(F)F)nn2)cc1Nc1ncccc1S(C)(=O)=O]

The preparation of Example 245 was followed using 3-chloro-6-(difluoromethoxy) pyridazine as the starting material to give title compound (4.5 mg, 36% yield). MS (M+1) m/z: 470.0 (MH$^+$). LC retention time 1.21 min [E].

Example 247

6-((6-isopropylpyridazin-3-yl)amino)-N-(methyl-d3)-4-((3-(methylsulfonyl)pyridin-2-yl)amino)pyridazine-3-carboxamide

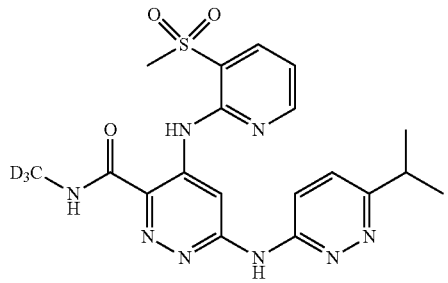 [SMILES: [2H]C([2H])([2H])NC(=O)c1nnc(Nc2ccc(C(C)C)nn2)cc1Nc1ncccc1S(C)(=O)=O]

The preparation of Example 245 was followed using 3-chloro-6-isopropylpyridazine as the starting material to give title compound (16.7 mg, 54% yield).

MS (M+1) m/z: 446.3 (MH$^1$). LC retention time 1.05 min [E].

Example 248

6-((6-(difluoromethyl)pyridazin-3-yl)amino)-N-(methyl-d3)-4-((3-(methylsulfonyl)pyridin-2-yl)amino)pyridazine-3-carboxamide

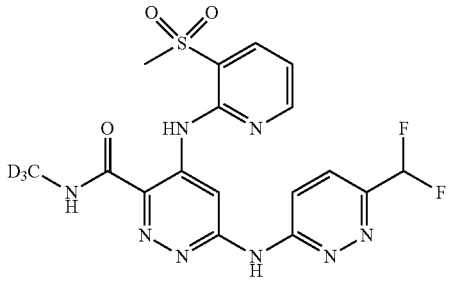 [SMILES: [2H]C([2H])([2H])NC(=O)c1nnc(Nc2ccc(C(F)F)nn2)cc1Nc1ncccc1S(C)(=O)=O]

Step 1: 6-chloropyridazine-3-carbaldehyde

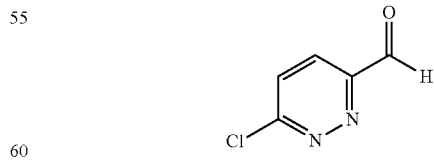

DIBAL-H (5.89 ml, 5.89 mmol) was added to a THF (29.5 ml) solution of methyl 6-chloropyridazine-3-carboxylate (0.5083 g, 2.95 mmol) at 0° C. The reaction was stirred at 0° C. for 30 min. The reaction was quenched at 0° C. by the addition of water (5 mL) and 1 N HCl (5.89 mL). The reaction mixture was warmed up to room temperature, and NaHCO₃ (saturated aqueous solution) was added. The crude product was extracted three times with DCM. The combined organic layers were dried (Na₂SO₄), filtered and concentrated. The crude product was purified using automated flash chromatography with ethyl acetate in hexane from 0 to 80% gave the titled product (0.22 g, 52%). HPLC retention time: 0.82 min [B]. ¹H NMR (400 MHz, CHLOROFORM-d) δ 10.34 (s, 1H), 8.03 (d, J=8.8 Hz, 1H), 7.77-7.71 (m, 1H).

Step 2: 3-chloro-6-(difluoromethyl)pyridazine

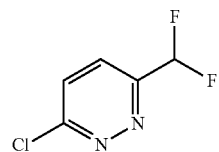

DAST (0.147 mL, 1.115 mmol) was added to a DCM (5 mL) solution of 6-chloropyridazine-3-carbaldehyde (0.106 g, 0.744 mmol) at 0° C. The reaction was stirred for 16 hours while it was warmed up to room temperature. The reaction was re-cooled to 0° C. and quenched with water. The reaction was diluted with DCM and washed with NaHCO₃ (saturated aqueous solution). The DCM layer was separated, dried (Na₂SO₄), filtered and concentrated to give the crude product, which was used as is (0.12 g, 36%).

MS (M+1) m/z: 165.1 (MH⁺). LC retention time 0.62 min [D]. ¹FINMR (400 MHz, CHLOROFORM-d) δ 7.87-7.79 (m, 1H), 7.77-7.68 (m, 1H), 7.10-6.78 (t, J=54.34 Hz, 1H). ¹⁹F NMR (376 MHz, CHLOROFORM-d) δ-114.89 (s, 2F).

Step 3

The preparation of Example 245 was followed using 3-chloro-(6-difluoromethyl) pyridazine as the starting material to give title compound 6-((6-(difluoromethyl)pyridazin-3-yl)amino)-N-(methyl-d3)-4-((3-(methylsulfonyl)pyridin-2-yl)amino)pyridazine-3-carboxamide (5.7 mg, 12% yield). MS (M+1) m/z: 454.2 (MH⁺). LC retention time 0.66 min [D]. ¹H NMR (400 MHz, CHLOROFORM-d) δ 12.50 (s, 1H), 9.24 (s, 1H), 8.62 (dd, J=4.8, 1.8 Hz, 1H), 8.51 (d, J=9.3 Hz, 1H), 8.38 (dd, J=7.8, 1.9 Hz, 2H), 8.24 (br s, 1H), 7.82 (d, J=9.3 Hz, 1H), 7.21 (dd, J=7.8, 4.8 Hz, 1H), 6.88 (t, J=56.0 Hz, 1H), 3.33 (s, 3H); ¹⁹F NMR (376 MHz, CHLOROFORM-d) δ-113.93 (s, 2F).

Example 249

6-((5-(1,3-dioxolan-2-yl)pyridin-2-yl)amino)-N-(methyl-d3)-4-((3-(methylsulfonyl)pyridin-2-yl)amino)pyridazine-3-carboxamide

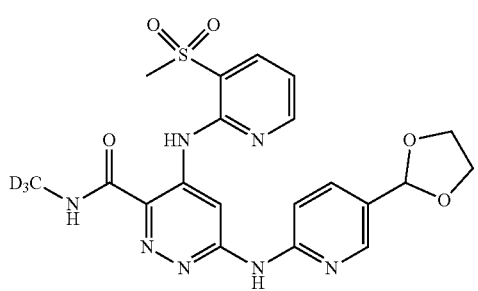 [SMILES: [2H]C([2H])([2H])NC(=O)c1nnc(Nc2ccc(C3OCCO3)cn2)cc1Nc1ncccc1S(C)(=O)=O]

Step 1: 2-chloro-5-(1,3-dioxolan-2-yl)pyridine

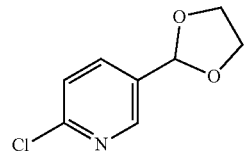 [SMILES: Clc1ccc(C2OCCO2)cn1]

The mixture of p-toluenesulfonic acid monohydrate (0.0766 g, 0.403 mmol), ethane-1,2-diol (0.2445 g, 3.94 mmol) and 6-chloronicotinaldehyde (0.3174 g, 2.242 mmol) in toluene (3 mL) was heated at 120° C. for 2 hours. The reaction was diluted with ethyl acetate and washed with 1N NaOH and then with water. The ethyl acetate layer was separated, dried (Na₂SO₄), and filtered. The product was purified by automated flash chromatography eluting with ethyl acetate in hexane from 0 to 30% (0.26 g, 62%).

MS (M+1) m/z: 185.9 (MH⁺). LC retention time 0.70 min [D]. ¹H NMR (400 MHz, CHLOROFORM-d) δ 8.50 (d, J=2.3 Hz, 1H), 7.77 (dd, J=8.2, 2.4 Hz, 1H), 7.37 (d, J=8.3 Hz, 1H), 5.86 (s, 1H), 4.15-4.06 (m, 4H).

Step 2

The preparation of Example 245 was followed using 2-chloro-5-(1,3-dioxolan-2-yl)-pyridine as the starting material to give title compound 6-((5-(1,3-dioxolan-2-yl)pyridin-2-yl)amino)-N-(methyl-d3)-4-((3-(methylsulfonyl)pyridin-2-yl)amino)pyridazine-3-carboxamide (4.7 mg, 31% yield). MS (M+1) m/z: 475.2 (MH⁺). LC retention time 1.15 min [E].

Example 250

N-(methyl-d3)-6-((5-(2-methyl-1,3-dioxolan-2-yl)pyridin-2-yl)amino)-4-((3-(methylsulfonyl)pyridin-2-yl)amino)pyridazine-3-carboxamide

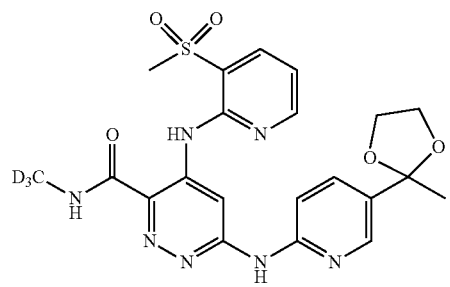 [SMILES: [2H]C([2H])([2H])NC(=O)c1nnc(Nc2ccc(C3(C)OCCO3)cn2)cc1Nc1ncccc1S(C)(=O)=O]

Step 1: 2-chloro-5-(2-methyl-1,3-dioxolan-2-yl)pyridine

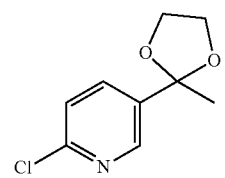

The preparation of Example 249 Step 1 was followed using 1-(6-chloropyridin-3-yl)ethan-1-one as the starting material gave the title product 2-chloro-5-(2-methyl-1,3-dioxolan-2-yl)pyridine (0.125 g, 45%). MS (M+1) m/z: 200.0 (MH⁺). LC retention time 0.79 min [D]. ¹H NMR (400

MHz, CHLOROFORM-d) δ 8.53-8.50 (m, 1H), 7.75 (dd, J=8.2, 2.5 Hz, 1H), 7.31 (dd, J=8.2, 0.7 Hz, 1H), 4.10-4.07 (m, 2H), 3.80-3.78 (m, 2H), 1.66 (s, 3H).

Step 2

The preparation of Example 245 was followed using 2-chloro-5-(2-methyl-1,3-dioxolan-2-yl)-pyridine as the starting material to give title compound N-(methyl-d3)-6-((5-(2-methyl-1,3-dioxolan-2-yl)pyridin-2-yl)amino)-4-((3-(methylsulfonyl)pyridin-2-yl)amino)pyridazine-3-carboxamide (4.4 mg, 27% yield). MS (M+1) m/z: 489.2 (MH$^+$). LC retention time 1.29 min [E]. $^1$H NMR (500 MHz, DMSO-d$_6$) δ 12.10-12.01 (m, 1H), 10.39-10.27 (m, 1H), 9.52-9.44 (m, 1H), 9.16-9.07 (m, 1H), 8.72-8.62 (m, 1H), 8.36-8.23 (m, 2H), 7.77-7.71 (m, 1H), 7.70-7.63 (m, 1H), 7.37-7.28 (m, 1H), 4.03-3.96 (m, 2H), 3.80-3.72 (m, 1H), 3.64-3.54 (m, 2H), 1.65-1.56 (m, 3H) (3H was buried below DMSO peak).

Example 251

N-(methyl-d3)-4-((3-(methylsulfonyl)pyridin-2-yl)amino)-6-(pyridazin-3-ylamino)pyridazine-3-carboxamide

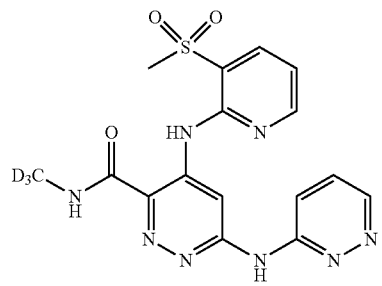 [SMILES: [2H]C([2H])([2H])NC(=O)c1nnc(Nc2cccnn2)cc1Nc1ncccc1S(C)(=O)=O]

Step 1: N-(methyl-d3)-4-((3-(methylthio)pyridin-2-yl)amino)-6-(pyridazin-3-ylamino)pyridazine-3-carboxamide

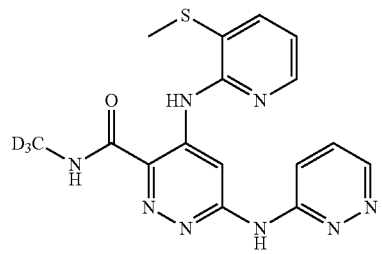 [SMILES: [2H]C([2H])([2H])NC(=O)c1nnc(Nc2cccnn2)cc1Nc1ncccc1SC]

The mixture of 1,1'-bis(dicyclohexylphosphino)ferrocene (6.27 mg, 10.84 μmol), Pd$_2$(dba)$_3$ (4.14 mg, 4.52 μmol), 6-chloro-N-(methyl-d3)-4-((3-(methylthio)pyridin-2-yl)amino)pyridazine-3-carboxamide (56.5 mg, 0.181 mmol), pyridazin-3-amine (25.8 mg, 0.271 mmol) and potassium phosphate tribasic (2 M in water, 0.226 mL, 0.452 mmol) in dioxane (2 mL) was degassed using a vacuum/N2 fill cycle three times and then heated to 110° C. for 1.5 hours. The reaction was diluted with ethyl acetate and washed three times with water. The ethyl acetate layer was separated, dried (Na$_2$SO$_4$), filtered and concentrated. Flash chromatography eluting with methanol in DCM from 0 to 10% gave the desired product. (39.3 mg, 59% yield). MS (M+1) m/z: 372.1 (MH$^+$). LC retention time 0.69 min [D].

Step 2

Sodium tungstate dihydrate (0.035 g, 0.106 mmol) was added to a suspension of hydrogen peroxide (30% solution in water, 0.325 mL, 3.18 mmol) and N-(methyl-d3)-4-((3-(methylthio)pyridin-2-yl)amino)-6-(pyridazin-3-ylamino)pyridazine-3-carboxamide (0.0394 g, 0.106 mmol) in AcOH (1 mL) at room temperature. After stirring at room temperature for 6 hours, the reaction was diluted with water, basified with Na$_2$CO$_3$ powder and extracted three times with DCM. The DCM layer was combined, washed with Na$_2$S$_2$O$_3$ (5% solution), dried (Na$_2$SO$_4$), filtered and concentrated. The crude was purified using reverse phase prepHPLC to provide the title compound (11 mg, 24% yield). MS (M+1) m/z: 404.2 (MH$^+$). LC retention time 0.80 min [D]. $^1$H NMR (500 MHz, DMSO-d$_6$) δ 12.02 (s, 1H), 10.55-10.44 (m, 1H), 9.31 (s, 1H), 9.01 (br s, 1H), 8.84 (d, J=4.2 Hz, 1H), 8.62 (br d, J=4.6 Hz, 1H), 8.29 (d, J=6.6 Hz, 1H), 8.06 (d, J=9.0 Hz, 1H), 7.62 (dd, J=9.0, 4.6 Hz, 1H), 7.33 (dd, J=7.7, 4.8 Hz, 1H)(3H was buried below DMSO peak).

Chiral Amide Synthesis of Intermediates 4 and 5

(S)-spiro[2.2]pentane-1-carboxamide and (R)-spiro[2.2]pentane-1-carboxamide

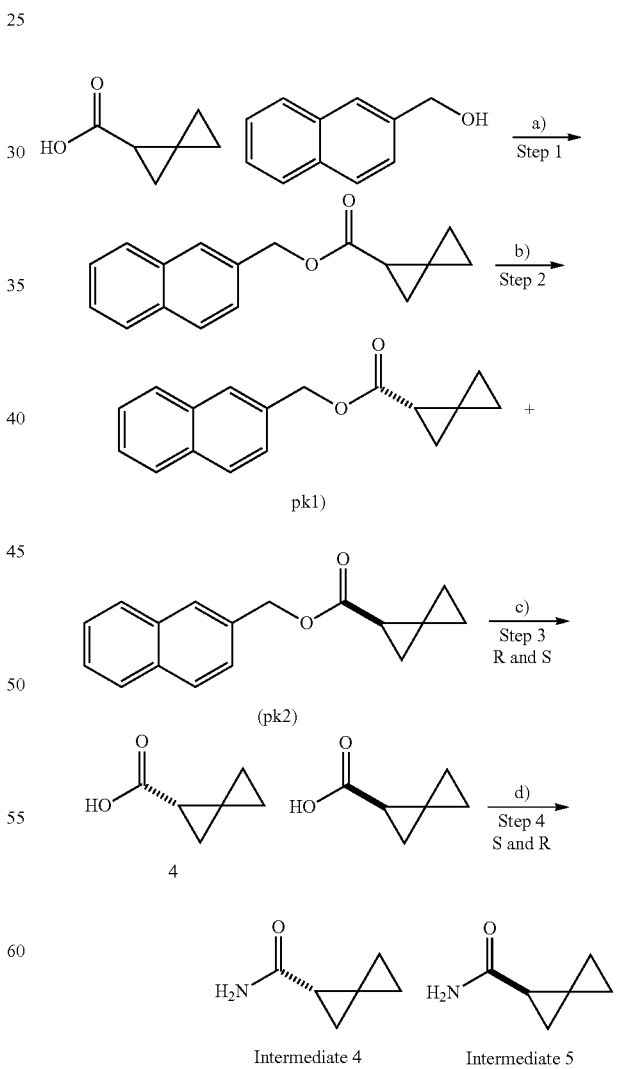

a). Di-tert-butyl (E)-diazene-1,2-dicarboxylate/PPh$_3$/THF; b) Chiral SFC Separation c). LiOH/THF/H$_2$O/MeOH; d) Oxalyl chloride (overnight); NH$_3$/MeOH Step 1: Naphthalen-2-ylmethyl spiro[2.2]pentane-1-carboxylate

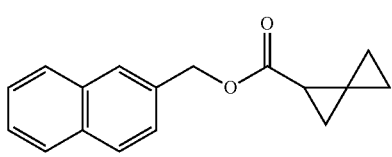

Di-tert-butyl (E)-diazene-1,2-dicarboxylate (0.407 g, 1.766 mmol) was added to a THF (5 mL) solution of spiro[2.2]pentane-1-carboxylic acid (0.1650 g, 1.472 mmol, Chembridge-BB), naphthalen-2-ylmethanol (0.279 g, 1.766 mmol), and triphenylphosphine (0.463 g, 1.766 mmol) at 0° C. After the addition completed the reaction was allowed to warm to room temperature and stirred for 14 hours. The reaction was diluted with DCM and silica gel was added. The volatile organic solvents were evaporated in vacuo and the resulting silica gel was loaded onto a pre-column. The product was purified by automated flash chromatography eluting with ethyl acetate in hexane from 0 to 5% (274 mg, 74% yield). $^1$H NMR (400 MHz, CHLOROFORM-d) δ 7.90-7.83 (m, 4H), 7.55-7.46 (m, 3H), 5.37-5.24 (m, 2H), 2.12-2.05 (m, 1H), 1.61-1.58 (m, 1H), 1.46-1.39 (m, 1H), 1.06-0.96 (m, 2H), 0.95-0.90 (m, 2H). HPLC retention time (Method A): $t_R$=3.69 min.

Step 2 (pk1) and (pk2)

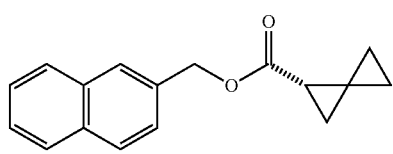 [SMILES: O=C(OCc1ccc2ccccc2c1)C1CC12CC2]

Naphthalen-2-ylmethyl (S)-spiro[2.2]pentane-1-carboxylate (pk1)

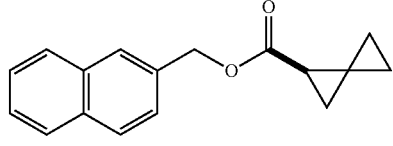

Naphthalen-2-ylmethyl (R)-spiro[2.2]pentane-1-carboxylate (pk2)

0.403 g of Step 1 compound was separated by chiral SFC described above. The two isomers isolated were named as "pk1" and "pk2" in the elution. Obtained pk1 title compound 0.1917 g (47% yield) and pk2 title compound 0.1728 g (43% yield). Stereochemical assignment based on comparison to literature values of the corresponding carboxylic acid (see below).
Naphthalen-2-ylmethyl (S)-spiro[2.2]pentane-1-carboxylate, pk1: $^1$H NMR (400 MHz, CHLOROFORM-d) δ 7.90-7.82 (m, 4H), 7.55-7.46 (m, 3H), 5.31 (q, J=12.5 Hz, 2H), 2.07 (dd, J=7.5, 4.2 Hz, 1H), 1.59 (t, J=4.0 Hz, 1H), 1.43 (dd, J=7.6, 3.8 Hz, 1H), 1.07-0.88 (m, 4H). SFC retention time: $t_R$=2.21 min. Optical rotation (OR): 72.90 (20° C.).
Naphthalen-2-ylmethyl (R)-spiro[2.2]pentane-1-carboxylate, pk2: $^1$H NMR (400 MHz, CHLOROFORM-d) δ 7.89-7.83 (m, 4H), 7.54-7.46 (m, 3H), 5.31 (q, J=12.4 Hz, 2H), 2.07 (dd, J=7.5, 4.2 Hz, 1H), 1.58 (t, J=4.0 Hz, 1H), 1.43 (dd, J=7.6, 3.8 Hz, 1H), 1.07-0.87 (m, 4H). SFC retention time: $t_R$=3.17 min. OR: −76.09 (20° C.).

Step 3S: (S)-spiro[2.2]pentane-1-carboxylic acid

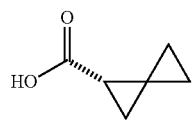

A mixture of lithium hydroxide (0.066 g, 2.78 mmol) and naphthalen-2-ylmethyl (S)-spiro[2.2]pentane-1-carboxylate (0.1751 g, 0.694 mmol) in THF (2 mL), water (0.5 mL) and MeOH (0.5 mL) was stirred at room temperature for 16 hours. The volatile organics were removed under vacuum and to the residue was added water. The aqueous solution was washed four times with DCM (discarded), and then acidified with 1N HCl (3.5 mL). The crude product was extracted from the aqueous layer three times with DCM. The combined DCM layers were dried (Na$_2$SO$_4$), filtered and concentrated to give the desired title compound (62.7 mg, 81% yield). $^1$H NMR (400 MHz, CHLOROFORM-d) δ 1.99 (dd, J=7.5, 4.2 Hz, 1H), 1.58 (t, J=4.0 Hz, 1H), 1.48 (dd, J=7.6, 3.8 Hz, 1H), 1.05-0.91 (m, 4H). OR: 188.25 (20° C.).

Step 3R: (R)-spiro[2.2]pentane-1-carboxylic acid

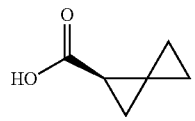

The titled product was prepared the same way as Step 3S from pk2 to give titled compound (R)-spiro[2.2]pentane-1-carboxylic acid. (60.0 mg, 83% yield). $^1$H NMR (400 MHz, CHLOROFORM-d) δ 1.99 (dd, J=7.6, 4.1 Hz, 1H), 1.58 (t, J=4.0 Hz, 1H), 1.47 (dd, J=7.6, 3.8 Hz, 1H), 1.04-0.90 (m, 4H). OR: −187.72 (20° C.). Literature OR $[α]_D^{25}$=−113.3° to −172.7° depending on optical purity (K. B. Wiberg, C. Osterle, *J. Org. Chem*, 64, 7763-7767 (1999).

Step 4S: (S)-spiro[2.2]pentane-1-carboxamide

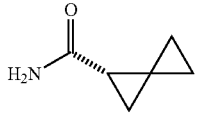

Oxalyl chloride (0.054 mL, 0.612 mmol)) was added to a DCM (3 mL) solution of (S)-spiro[2.2]pentane-1-carboxylic acid (0.0572 g, 0.510 mmol) at room temperature. The reaction was stirred for 16 hours then the volatile organics were removed under vacuum. To the crude acid chloride was added DCM (1.5 mL) and then ammonia (7 M in MeOH, 2.5 mL, 17.50 mmol) solution was added to the intermediate at 0° C. The reaction was stirred overnight while allowing to warm to room temperature. The solvent was removed under vacuum to give a tan solid as the title compound (39.8 mg, 70% yield). $^1$H NMR (400 MHz, CHLOROFORM-d) δ 5.51-5.16 (m, 2H), 1.91-1.84 (m, 1H), 1.50-1.44 (m, 1H), 1.43-1.38 (m, 1H), 0.96 (s, 4H).

Step 4R: (R)-spiro[2.2]pentane-1-carboxamide

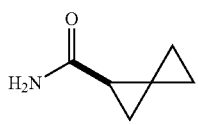

The titled product was prepared the same way as Step 4S from (R)-spiro[2.2]pentane-1-carboxylic acid as starting material to give title compound (53.5 mg, 98% yield). $^1$H NMR (400 MHz, CHLOROFORM-d) δ 5.51-5.22 (m, 2H), 1.91-1.85 (m, 1H), 1.48-1.43 (m, 1H), 1.43-1.37 (m, 1H), 0.96 (s, 4H).

General Scheme for Examples 252 and 253:

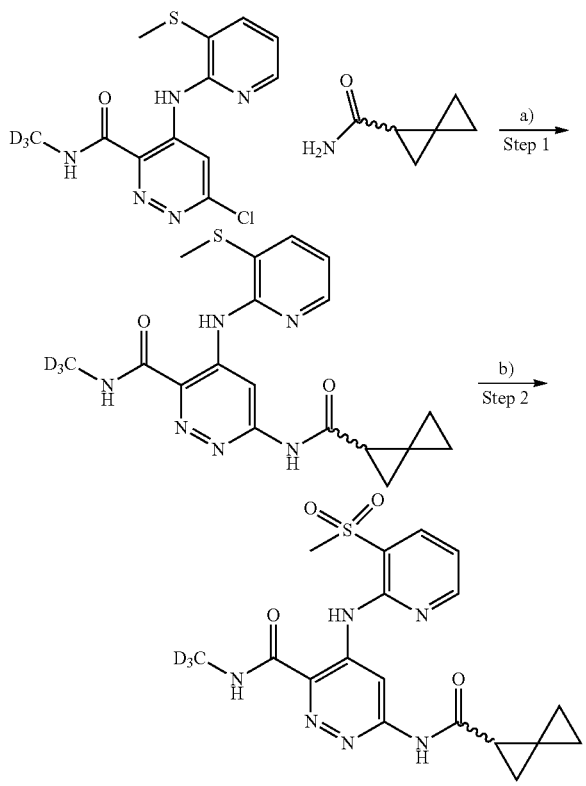

a.) Pd$_2$(dba)$_3$/Xantphos/Cs$_2$CO$_3$/Dioxane; b). Sodium tungstate dihydrate/H$_2$O$_2$/AcOH Example 252

Step 1

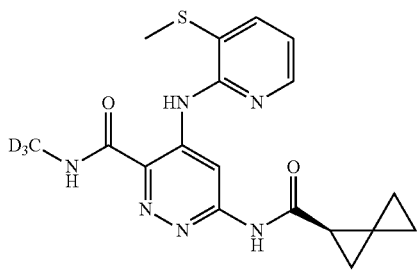 [SMILES: [2H]C([2H])([2H])NC(=O)c1nnc(NC(=O)[C@@H]2CC23CC3)cc1Nc1ncccc1SC]

A mixture of cesium carbonate (149 mg, 0.457 mmol), Xantphos (14.43 mg, 0.025 mmol), Pd$_2$(dba)$_3$ (11.42 mg, 0.012 mmol), 6-chloro-N-(methyl-d3)-4-((3-(methylthio)pyridin-2-yl)amino)pyridazine-3-carboxamide (65 mg, 0.208 mmol), and (R)-spiro[2.2]pentane-1-carboxamide (50.8 mg, 0.457 mmol) in dioxane (3 mL) was degassed using a vacuum/N2 fill cycle three times. The reaction was heated at 110° C. for 16 hours. The reaction was diluted with water and DCM. The DCM layer was separated and washed two more times with water and then dried (Na$_2$SO$_4$), filtered and concentrated. Purification via automated flash chromatography, eluting with methanol in DCM from 0 to 10%, gave the title compound (R)—N-(methyl-d3)-4-((3-(methylthio)pyridin-2-yl)amino)-6-(spiro[2.2]pentane-1-carboxamido)pyridazine-3-carboxamide (54 mg, 67% yield). $^1$H NMR (400 MHz, CHLOROFORM-d) δ 12.15 (br s, 1H), 9.88 (s, 1H), 8.68 (br s, 1H), 8.36 (br d, J=3.5 Hz, 1H), 8.25 (br s, 1H), 7.72 (br d, J=7.4 Hz, 1H), 6.97 (br dd, 5.1 Hz, 1H), 2.51 (s, 3H), 2.21-2.09 (m, 1H), 1.58-1.10 (m, 6H), 1.08-0.93 (m, 5H).

LCMS (ESI) m/e 388.1 [(M+H)$^+$, calc'd C$_{18}$H$_{18}$D$_3$N$_6$O$_2$S$_1$, 388.1]; LC/MS retention time (method D): t$_R$=0.80 min.

Step 2

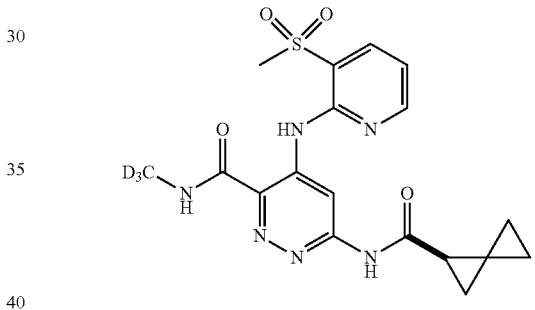

To a suspension of hydrogen peroxide (30% solution in water, 0.258 mL, 2.52 mmol) and (R)—N-(methyl-d3)-4-((3-(methylthio)pyridin-2-yl)amino)-6-(spiro[2.2]pentane-1-carboxamido)pyridazine-3-carboxamide (0.0489 g, 0.126 mmol) in AcOH (1 mL) was added sodium tungstate dihydrate (0.042 g, 0.126 mmol) at room temperature. After stirring at room temperature for 1 hour, the reaction was diluted with water, basified with Na$_2$CO$_3$ powder and extracted three times with DCM. The DCM layers were combined, washed with Na$_2$S$_2$O$_3$ (5% solution), dried (Na$_2$SO$_4$), filtered and concentrated. The crude product was purified using reverse phase prepHPLC to give the title compound (R)—N-(methyl-d3)-4-((3-(methylsulfonyl)pyridin-2-yl)amino)-6-(spiro[2.2]pentane-1-carboxamido)pyridazine-3-carboxamide (16.2 mg, 31%) as a colorless solid. $^1$H NMR (500 MHz, DMSO-d$_6$) δ 12.07 (s, 1H), 11.22 (s, 1H), 9.49 (s, 1H), 9.16 (s, 1H), 8.63 (dd, J=4.6, 1.5 Hz, 1H), 8.29 (dd, J=7.8, 1.4 Hz, 1H), 7.34 (dd, J=7.8, 4.7 Hz, 1H), 2.48-2.43 (m, 1H), 1.46-1.41 (m, 1H), 1.42-1.36 (m, 1H), 0.95-0.82 (m, 3H), 0.80-0.73 (m, 1H). (3H methyl sulfone was buried under DMSO peak).

LCMS (ESI) m/e 420.0 [(M+H)$^1$, calc'd C$_{18}$H$_{18}$D$_3$N$_6$O$_4$S, 420.1]; LC/MS retention time (method E): t$_R$=1.38 min; OR: −205.39 (20° C.).

Example 253

Step 1

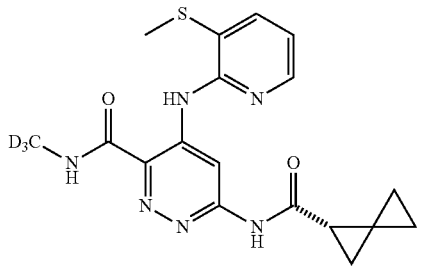

Following the preparation of Example 252 (Step 1) using (S)-spiro[2.2]pentane-1-carboxamide, the titled compound (S)—N-(methyl-d3)-4-((3-(methylthio)pyridin-2-yl)amino)-6-(spiro[2.2]pentane-1-carboxamido)pyridazine-3-carboxamide was obtained (55 mg, 72% yield). LCMS (ESI) m/e 388.1 [(M+H)$^+$, calc'd $C_{18}H_{18}D_3N_6O_2S_1$, 388.1]; LC/MS retention time (method D): $t_R$=0.80 min.

Step 2

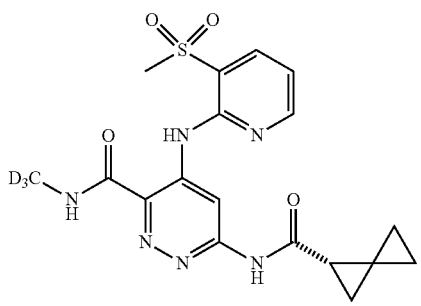

Follow the preparation of Example 252, the titled compound (S)—N-(methyl-d3)-4-((3-(methylsulfonyl)pyridin-2-yl)amino)-6-(spiro[2.2]pentane-1-carboxamido) pyridazine-3-carboxamide was obtained (13.3 mg, 23% yield) as a colorless solid. $^1$H NMR (500 MHz, DMSO-d6) δ 12.02 (s, 1H), 11.07 (s, 1H), 9.53 (s, 1H), 9.09 7 (s, 1H), 8.67-8.55 (m, 1H), 8.36-8.23 (m, 1H), 7.40-7.25 (m, 1H), 2.47-2.43 (m, 1H), 1.50-1.42 (m, 1H), 1.40-1.34 (m, 1H), 1.00-0.83 (m, 3H), 0.83-0.73 (m, 1H). (3H methyl sulfone was buried under DMSO peak). LCMS (ESI) m/e 420.1 [(M+H)$^+$, calc'd $C_{18}H_{18}D_3N_6O_4S$, 420.1]; LC/MS retention time (method E): $t_R$=1.39 min. OR: 160.12 (20° C.).

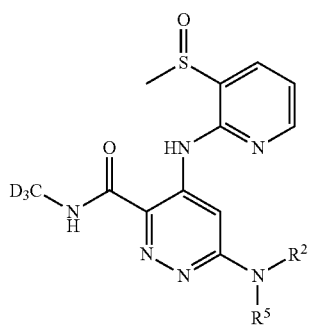

The following Examples were prepared in a similar manner to the product of Example 177, Step 2.

TABLE 15

| Example No. | NR$^2$R$^5$ | MW | m/z [M + H]$^+$ | Rt (min) [Method] |
|---|---|---|---|---|
| 254 | ![structure] | 415.49 | 416 | |
| 255 | ![structure] | 417.47 | 417.9 | 1.87 Method A (254 nm) |
| 256 | ![structure] | 389.46 | 390.2 | 1.84 Method A (254 nm) |

BIOLOGICAL ASSAYS

The following assay is used to show the activity for compounds of the invention.

IFNα-Induced STAT Phosphorylation in Human Whole Blood

After an hour long incubation with compound, human whole blood (drawn with either EDTA or ACD-A as anticoagulant) was stimulated with 1000 U/mL recombinant human IFNα A/D (R&D Systems 11200-2) for 15 min. The stimulation was stopped by adding Fix/Lyse buffer (BD 558049). Cells were stained with a CD3 FITC antibody (BD 555916), washed, and permeabilized on ice using Perm III buffer (BD 558050). Cells were then stained with an Alexa-Fluor 647 pSTAT5 (pY694) antibody (BD 612599) for 30 min prior to analysis on the FACS Canto II. The amount of pSTAT5 expression was quantitated by median fluorescence intensity after gating on the CD3 positive population.

IFNα-Induced STAT Phosphorylation in Human Whole Blood Inhibition Data

| Example No. | IFNα-Induced Stat Phosph. (IC$_{50}$, μM) |
|---|---|
| 1 | 0.012 |
| 2 | 0.026 |
| 4 | 0.032 |
| 5 | 0.013 |
| 7 | 0.042 |
| 8 | 0.049 |
| 9 | 0.077 |
| 10 | 0.021 |
| 12 | 0.038 |
| 13 | 0.002 |
| 14 | 0.011 |
| 15 | 0.013 |
| 16 | 1.434 |
| 17 | 0.018 |
| 19 | 0.044 |
| 20 | 0.047 |

| Example No. | IFNα-Induced Stat Phosph. (IC$_{50}$, μM) |
|---|---|
| 21 | 0.037 |
| 22 | 0.031 |
| 23 | 2.14 |
| 24 | 0.009 |
| 25 | 0.015 |
| 26 | 0.049 |
| 27 | 0.088 |
| 28 | 0.028 |
| 29 | 0.092 |
| 30 | 0.057 |
| 31 | 0.031 |
| 32 | 0.036 |
| 33 | 0.018 |
| 34 | 0.115 |
| 35 | 0.090 |
| 36 | 0.022 |
| 37 | 0.026 |
| 38 | 0.018 |
| 39 | 0.015 |
| 40 | 0.018 |
| 41 | 0.024 |
| 42 | 0.015 |
| 43 | 0.026 |
| 44 | 0.014 |
| 45 | 0.034 |
| 46 | 0.053 |
| 47 | 0.048 |
| 48 | 0.040 |
| 49 | 0.058 |
| 50 | 0.03 |
| 51 | 0.029 |
| 52 | 0.092 |
| 53 | 0.132 |
| 56 | 0.018 |
| 57 | 0.059 |
| 58 | 0.024 |
| 59 | 0.219 |
| 61 | 0.018 |
| 62 | 1.682 |
| 63 | 0.013 |
| 64 | 0.079 |
| 65 | 0.193 |
| 66 | 1.237 |
| 67 | 3.581 |
| 68 | 1.345 |
| 69 | 0.012 |
| 70 | 1.096 |
| 71 | 0.032 |
| 72 | 0.023 |
| 73 | 0.076 |
| 74 | 0.004 |
| 75 | 0.018 |
| 76 | 0.02 |
| 77 | 0.398 |
| 78 | 0.04 |
| 79 | 0.024 |
| 80 | 0.057 |
| 81 | 0.003 |
| 82 | 0.037 |
| 83 | 0.076 |
| 84 | 0.042 |
| 85 | 0.011 |
| 86 | 0.04 |
| 87 | 0.417 |
| 88 | 0.047 |
| 89 | 0.032 |
| 90 | 0.013 |
| 91 | 0.043 |
| 92 | 0.013 |
| 93 | 0.028 |
| 94 | 0.162 |
| 95 | 0.133 |
| 96 | 0.004 |
| 97 | 0.013 |
| 98 | 0.049 |
| 99 | 0.044 |
| 100 | 0.015 |
| 101 | 0.095 |
| 102 | 0.138 |
| 103 | 0.016 |
| 104 | 0.046 |
| 105 | 0.009 |
| 106 | 0.124 |
| 107 | 0.013 |
| 108 | 0.167 |
| 110 | 0.02 |
| 111 | 0.248 |
| 112 | 0.142 |
| 113 | 0.088 |
| 115 | 0.190 |
| 116 | 0.782 |
| 117 | 0.334 |
| 118 | 0.131 |
| 119 | 0.073 |
| 120 | 0.062 |
| 121 | 0.039 |
| 122 | 0.156 |
| 123 | 0.183 |
| 124 | 0.037 |
| 125 | 0.272 |
| 126 | 0.343 |
| 127 | 0.302 |
| 128 | 0.061 |
| 129 | 0.08 |
| 130 | 0.310 |
| 131 | 0.434 |
| 132 | 0.209 |
| 133 | 1.569 |
| 134 | 0.296 |
| 135 | 0.227 |
| 136 | 0.349 |
| 137 | 0.141 |
| 138 | 0.447 |
| 139 | 0.893 |
| 140 | 0.034 |
| 145 | 0.255 |
| 147 | 0.231 |
| 148 | 0.408 |
| 149 | 0.141 |
| 151 | 0.002 |
| 152 | 0.04 |
| 153 | 0.36 |
| 154 | 0.006 |
| 155 | 0.007 |
| 156 | 0.007 |
| 157 | 0.021 |
| 158 | 0.01 |
| 159 | 0.012 |
| 160 | 0.011 |
| 161 | 0.047 |
| 163 | 0.095 |
| 164 | 0.088 |
| 165 | 0.023 |
| 166 | 0.04 |
| 167 | 0.06 |
| 168 | 0.016 |
| 169 | 0.008 |
| 170 | 0.011 |
| 171 | 0.009 |
| 172 | 0.018 |
| 173 | 0.017 |
| 174 | 1.808 |
| 175 | 0.278 |
| 176 | 0.132 |
| 177 | 0.648 |
| 178 | 0.474 |
| 179 | 1.062 |
| 180 | 0.073 |
| 181 | 0.55 |
| 182 | 2.227 |

-continued

| Example No. | IFNα-Induced Stat Phosph. (IC$_{50}$, μM) |
|---|---|
| 183 | 0.105 |
| 184 | 0.263 |
| 185 | 1.727 |
| 186 | 0.132 |
| 187 | 0.032 |
| 188 | 0.006 |
| 189 | 0.106 |
| 190 | 0.061 |
| 191 | 0.066 |
| 192 | 0.013 |
| 193 | 0.165 |
| 194 | 0.035 |
| 195 | 0.211 |
| 196 | 0.012 |
| 197 | 0.058 |
| 198 | 0.262 |
| 199 | 1.034 |
| 200 | 0.198 |
| 201 | 0.024 |
| 202 | 0.05 |
| 203 | 0.046 |
| 204 | 0.579 |
| 207 | 0.229 |
| 208 | 0.067 |
| 209 | 0.056 |
| 211 | 0.09 |
| 212 | 1.082 |
| 213 | 0.114 |
| 214 | 0.046 |
| 215 | 0.021 |
| 216 | 0.028 |
| 217 | 0.052 |
| 218 | 0.034 |
| 219 | 0.024 |
| 220 | 0.015 |
| 221 | 0.013 |
| 222 | 0.059 |
| 223 | 0.094 |
| 224 | 0.044 |
| 225 | 0.164 |
| 226 | 0.217 |
| 227 | 0.009 |
| 228 | 0.181 |
| 229 | 0.047 |
| 230 | 0.022 |
| 231 | 0.36 |
| 232 | 0.131 |
| 233 | 0.061 |
| 234 | 0.636 |
| 235 | 0.144 |
| 236 | 0.013 |
| 237 | 1.082 |
| 238 | 2.454 |
| 239 | 0.288 |
| 240 | 0.115 |
| 241 | 0.203 |
| 242 | 0.05 |
| 243 | 0.832 |
| 244 | 0.42 |
| 245 | 0.01 |
| 246 | 0.034 |
| 247 | 0.006 |
| 251 | 0.007 |
| 252 | 0.053 |
| 253 | 0.047 |
| 254 | 0.186 |
| 255 | 0.466 |
| 256 | 0.744 |

We claim:

1. A compound having the following formula I:

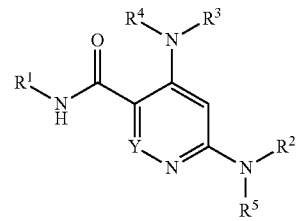

or a stereoisomer or pharmaceutically acceptable salt thereof, wherein

Y is N or CR$^6$;

R$^1$ is H, CD$_3$ or C$_{1-3}$ alkyl;

R$^2$ is —C(O)R$^{2a}$; or C$_{1-6}$ alkyl, —(CH$_2$)$_r$-3-14 membered carbocycle substituted with 0-1 R$^{2a}$ or a 5-14 membered heterocycle containing 1-4 heteroatoms selected from N, O, and S, substituted with 0-4 R$^{2a}$;

R$^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)R$^c$, —NR$^b$C(O)NR$^{11}$R$^{11}$, —S(O)$_p$NR$^{11}$NR$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^3$ is

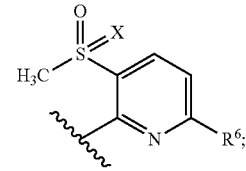

X is absent, O or NH;

R$^4$ and R$^5$ are independently hydrogen, C$_{1-4}$ alkyl substituted with 0-1 R$^f$, (CH$_2$)$_r$-phenyl substituted with 0-3 R$^d$ or a —(CH$_2$)-5-7 membered heterocycle containing 1-4 heteroatoms selected from N, O, and S(O)$_p$;

R$^6$ is hydrogen, halo, C$_{1-4}$ alkyl, C$_{1-4}$ alkyoxy, C$_{1-4}$ haloalkyl, C$_{1-4}$ haloalkoxy, C$_{3-6}$ cycloalkyl, CN, NO$_2$ or OH;

R$^{11}$ at each occurrence is independently hydrogen, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2; and r is 0, 1, 2, 3, or 4.

2. The compound according to claim 1 of formula II

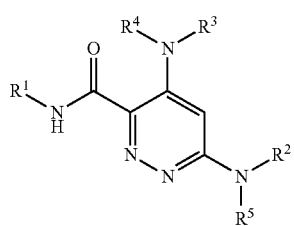

or a stereoisomer or pharmaceutically acceptable salt thereof, wherein $R^1$ is H, $CD_3$ or $C_{1-3}$ alkyl;

$R^2$ is —$C(O)R^{2a}$; or $C_{1-6}$ alkyl, —$(CH_2)_r$-3-14 membered carbocycle substituted with 0-1 $R^{2a}$ or a 5-14 membered heterocycle containing 1-4 heteroatoms selected from N, O, and S, substituted with 0-4 $R^{2a}$;

$R^{2a}$ at each occurrence is independently hydrogen, OH, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}NR^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is

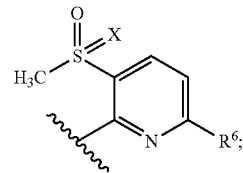

X is absent, O or NH;

$R^4$ and $R^5$ are independently hydrogen, $C_{1-4}$ alkyl substituted with 0-1 $R^f$, $(CH_2)_r$-phenyl substituted with 0-3 $R^d$ or a —$(CH_2)$-5-7 membered heterocycle containing 1-4 heteroatoms selected from N, O, and $S(O)_p$;

$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2; and r is 0, 1, 2, 3, or 4.

3. The compound according to claim 1 of formula III

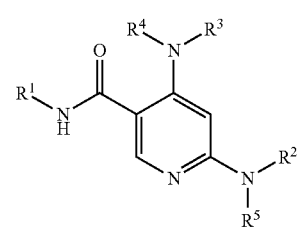

or a stereoisomer or pharmaceutically acceptable salt thereof, wherein
R¹ is H, CD₃ or C₁₋₃ alkyl;
R² is —C(O)R²ᵃ; or C₁₋₆ alkyl, —(CH₂)ᵣ-3-14 membered carbocycle substituted with 0-1 R²ᵃ or a 5-14 membered heterocycle containing 1-4 heteroatoms selected from N, O, and S, substituted with 0-4 R²ᵃ;
R²ᵃ at each occurrence is independently hydrogen, OH, halo, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle containing 1-4 heteroatoms selected from N, O, and S(O)ₚ substituted with 0-2 Rᵃ;
R³ is

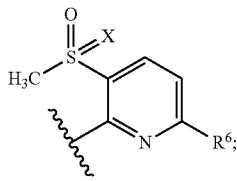

X is absent, O or NH;
R⁴ and R⁵ are independently hydrogen, C₁₋₄ alkyl substituted with 0-1 Rᶠ, (CH₂)ᵣ-phenyl substituted with 0-3 Rᵈ or a —(CH₂)-5-7 membered heterocycle containing 1-4 heteroatoms selected from N, O, and S(O)ₚ;
R⁶ is hydrogen, halo, C₁₋₄ alkyl, C₁₋₄ alkyoxy, C₁₋₄ haloalkyl, C₁₋₄ haloalkoxy, C₃₋₆ cycloalkyl, CN, NO₂ or OH;
R¹¹ at each occurrence is independently hydrogen, C₁₋₄ alkyl substituted with 0-3 Rᶠ, CF₃, C₃₋₁₀ cycloalkyl substituted with 0-1 Rᶠ, (CH₂)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;
Rᵃ at each occurrence are independently hydrogen, F, Cl, Br, OCF₃, CF₃, CHF₂, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)Rᶜ, —S(O)₂Rᶜ, C₁₋₆ alkyl substituted with 0-3 Rᶠ, C₁₋₆ haloalkyl, C₂₋₆ alkenyl substituted with 0-3 Rᵃ, C₂₋₆ alkynyl substituted with 0-3 Rᵃ, —(CH₂)ᵣ-3-14 membered carbocycle or —(CH₂)ᵣ-5-7 membered heterocycle containing 1-4 heteroatoms selected from N, O, and S(O)ₚ substituted with 0-3 Rᶠ;
Rᵇ is hydrogen, C₁₋₆ alkyl substituted with 0-3 Rᵈ, C₁₋₆ haloalkyl, C₃₋₆ cycloalkyl substituted with 0-2 Rᵈ, or —(CH₂)ᵣ-5-7 membered heterocycle containing 1-4 heteroatoms selected from N, O, and S(O)ₚ substituted with 0-3 Rᶠ or (CH₂)ᵣ-phenyl substituted with 0-3 Rᵈ;
Rᶜ is C₁₋₆ alkyl substituted with 0-3 Rᶠ, (CH₂)ᵣ—C₃₋₆ cycloalkyl substituted with 0-3 Rᶠ or (CH₂)ᵣ-phenyl substituted with 0-3 Rᶠ;
Rᵈ is independently at each occurrence, hydrogen, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₆ alkyl or (CH₂)ᵣ-phenyl substituted with 0-3 Rᶠ;

Rᵉ is independently at each occurrence, hydrogen, C₁₋₆ alkyl, C₃₋₆ cycloalkyl or (CH₂)ᵣ-phenyl substituted with 0-3 Rᶠ;
Rᶠ is independently at each occurrence, hydrogen, halo, CN, NH₂, OH, C₃₋₆ cycloalkyl, CF₃, O(C₁₋₆ alkyl) or a —(CH₂)ᵣ-5-7 membered heterocycle containing 1-4 heteroatoms selected from N, O, and S(O)ₚ;
p is 0, 1, or 2; and
r is 0, 1, 2, 3, or 4.

4. The compound according to claim 2 of the formula

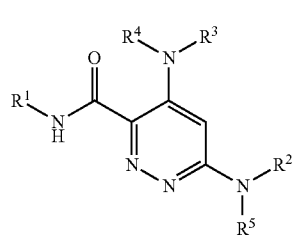

II or a stereoisomer or pharmaceutically acceptable salt thereof,
wherein
R¹ is H, CD₃ or C₁₋₃ alkyl;
R² is —C(O)R²ᵃ; or C₁₋₆ alkyl, —(CH₂)ᵣ-3-14 membered carbocycle substituted with 0-1 R²ᵃ or a 5-14 membered heterocycle containing 1-4 heteroatoms selected from N, O, and S, substituted with 0-4 R²ᵃ;
R²ᵃ at each occurrence is independently hydrogen, OH, halo, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle containing 1-4 heteroatoms selected from N, O, and S(O)ₚ substituted with 0-2 Rᵃ;
R³ is

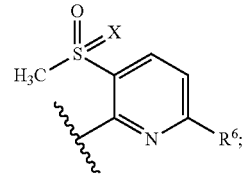

X is O;
R⁴ and R⁵ are independently hydrogen, C₁₋₄ alkyl substituted with 0-1 Rᶠ, (CH₂)ᵣ-phenyl substituted with 0-3 Rᵈ or a —(CH₂)-5-7 membered heterocycle containing 1-4 heteroatoms selected from N, O, and S(O)ₚ;
R⁶ is hydrogen, halo, C₁₋₄ alkyl, C₁₋₄ alkyoxy, C₁₋₄ haloalkyl, C₁₋₄ haloalkoxy, C₃₋₆ cycloalkyl, CN, NO₂ or OH;
R¹¹ at each occurrence is independently hydrogen, C₁₋₄ alkyl substituted with 0-3 Rᶠ, CF₃, C₃₋₁₀ cycloalkyl substituted with 0-1 Rᶠ, (CH₂)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;

$R^a$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2; and r is 0, 1, 2, 3, or 4.

5. The compound according to claim 4 of the formula

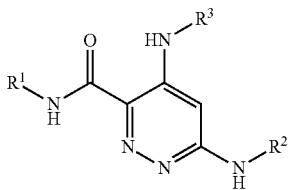

or a stereoisomer or pharmaceutically acceptable salt thereof, wherein $R^1$ is H, $CD_3$ or $C_{1-3}$ alkyl;

$R^2$ is —$C(O)R^{2a}$; or $C_{1-6}$alkyl, —$(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is

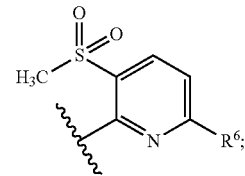

$R^6$ is hydrogen, halo, $C_{1-4}$ alkyl, $C_{1-4}$ alkyoxy, $C_{1-4}$ haloalkyl, $C_{1-4}$ haloalkoxy, $C_{3-6}$ cycloalkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2; and r is 0, 1, 2, 3, or 4.

6. The compound according to claim 5 of the formula

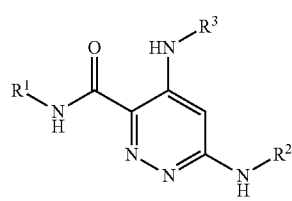

or a stereoisomer or pharmaceutically acceptable salt thereof, wherein
R$^1$ is H, CD$_3$ or C$_{1-3}$ alkyl;
R$^2$ is —C(O)R$^{2a}$; or C$_{1-6}$alkyl, —(CH$_2$)$_r$-3-14 membered carbocycle substituted with 0-1 R$^{2a}$ or a 5-14 membered heterocycle containing 1-4 heteroatoms selected from N, O, and S, each group substituted with 0-4 R$^{2a}$;
R$^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;
R$^3$ is

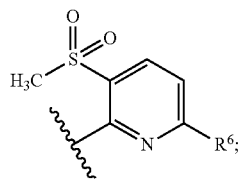

R$^6$ is hydrogen, halo, C$_{1-3}$ alkyl, C$_{1-3}$ alkyoxy or C$_{3-6}$ cycloalkyl;
R$^{11}$ at each occurrence is independently hydrogen, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or a —(CH$_2$)$_r$-5-7 membered heterocycle containing 1-4 heteroatoms selected from N, O, and S(O)$_p$ substituted with 0-3 R$^d$;
R$^a$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or a —(CH$_2$)$_r$-5-7 membered heterocycle containing 1-4 heteroatoms selected from N, O, and S(O)$_p$ substituted with 0-3 R$^f$;
R$^b$ is hydrogen, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;
R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;
R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;
R$^e$ is independently at each occurrence, hydrogen, C$_{1-6}$ alkyl, C$_{3-6}$ cycloalkyl or (CH$_2$)$_r$-phenyl substituted with 0-3 R$^f$;
R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2; and
r is 0, 1, 2, 3, or 4.

7. The compound according to claim 6 of the formula

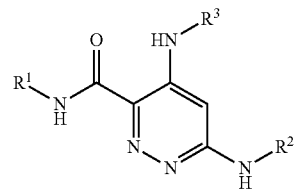

or a stereoisomer or pharmaceutically acceptable salt thereof,
wherein
R$^1$ is H, CD$_3$ or C$_{1-3}$ alkyl;
R$^2$ is pyridine, pyridazine, pyrimidine, pyrazine, pyrazole, triazole, isoxazole, isothiazole or quinoline, each group substituted with 0-4 R$^{2a}$;
R$^{2a}$ at each occurrence is independently hydrogen, OH, halo, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;
R$^3$ is

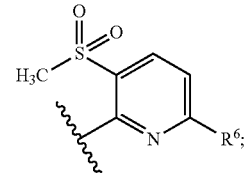

R$^6$ is hydrogen, halo, C$_{1-3}$ alkyl, C$_{1-3}$ alkyoxy or C$_{3-6}$ cycloalkyl;
R$^{11}$ at each occurrence is independently hydrogen, C$_{1-4}$ alkyl substituted with 0-3 R$^f$, CF$_3$, C$_{3-10}$ cycloalkyl substituted with 0-1 R$^f$, (CH$_2$)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;
R$^a$ at each occurrence are independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2; and r is 0, 1, 2, 3, or 4.

8. The compound according to claim 3 of the formula

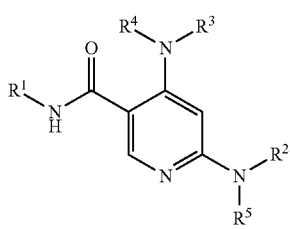

III or a stereoisomer or pharmaceutically acceptable salt thereof, wherein $R^1$ is H, $CD_3$ or $C_{1-3}$ alkyl;

$R^2$ is —$C(O)R^{2a}$; or $C_{1-6}$alkyl, —$(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is

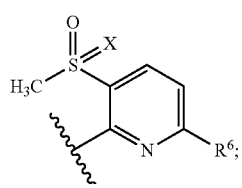

X is O;

$R^4$ and $R^5$ are independently hydrogen, $C_{1-4}$ alkyl substituted with 0-1 $R^f$, $(CH_2)_r$-phenyl substituted with 0-3 $R^d$ or a —$(CH_2)$-5-7 membered heterocycle containing 1-4 heteroatoms selected from N, O, and $S(O)_p$;

$R^6$ is hydrogen, halo, $C_{1-4}$ alkyl, $C_{1-4}$ haloalkyl, —$OC_{1-4}$ haloalkyl, $OC_{1-4}$ alkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ at each occurrence are independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2; and r is 0, 1, 2, 3, or 4.

9. The compound according to claim 8 of the formula

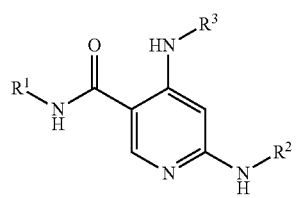

or a stereoisomer or pharmaceutically acceptable salt thereof, wherein $R^1$ is H, $CD_3$ or $C_{1-3}$ alkyl;

$R^2$ is —$C(O)R^{2a}$; or $C_{1-6}$alkyl, —$(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$;

$R^{2a}$ at each occurrence is independently hydrogen, OH, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle containing 1-4 heteroatoms selected from N, O, and S(O)ₚ substituted with 0-2 Rᵃ;

R³ is

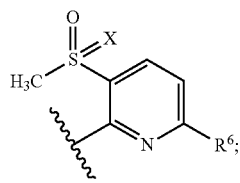

X is O;

R⁶ is hydrogen, halo, C₁₋₄ alkyl, C₁₋₄ haloalkyl, —OC₁₋₄ haloalkyl, OC₁₋₄ alkyl, CN, NO₂ or OH;

R¹¹ at each occurrence is independently hydrogen, C₁₋₄ alkyl substituted with 0-3 Rᶠ, CF₃, C₃₋₁₀ cycloalkyl substituted with 0-1 Rᶠ, (CH)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;

Rᵃ at each occurrence are independently hydrogen, F, Cl, Br, OCF₃, CF₃, CHF₂, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)Rᶜ, —S(O)₂Rᶜ, C₁₋₆ alkyl substituted with 0-3 Rᶠ, C₁₋₆ haloalkyl, C₂₋₆ alkenyl substituted with 0-3 Rᵃ, C₂₋₆ alkynyl substituted with 0-3 Rᵃ, —(CH₂)ᵣ-3-14 membered carbocycle or —(CH₂)ᵣ-5-7 membered heterocycle containing 1-4 heteroatoms selected from N, O, and S(O)ₚ substituted with 0-3 Rᶠ;

Rᵇ is hydrogen, C₁₋₆ alkyl substituted with 0-3 Rᵈ, C₁₋₆ haloalkyl, C₃₋₆ cycloalkyl substituted with 0-2 Rᵈ, or —(CH₂)ᵣ-5-7 membered heterocycle containing 1-4 heteroatoms selected from N, O, and S(O)ₚ substituted with 0-3 Rᶠ or (CH₂)ᵣ-phenyl substituted with 0-3 Rᵈ;

Rᶜ is C₁₋₆ alkyl substituted with 0-3 Rᶠ, (CH₂)ᵣ—C₃₋₆ cycloalkyl substituted with 0-3 Rᶠ or (CH₂)ᵣ-phenyl substituted with 0-3 Rᶠ;

Rᵈ at each occurrence is independently hydrogen, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₆ alkyl or (CH₂)ᵣ-phenyl substituted with 0-3 Rᶠ;

Rᵉ at each occurrence is independently selected from hydrogen, C₁₋₆ alkyl, C₃₋₆ cycloalkyl and (CH₂)ᵣ-phenyl substituted with 0-3 Rᶠ;

Rᶠ independently at each occurrence is hydrogen, halo, CN, NH₂, OH, C₃₋₆ cycloalkyl, CF₃, O(C₁₋₆ alkyl) or a —(CH₂)ᵣ-5-7 membered heterocycle containing 1-4 heteroatoms selected from N, O, and S(O)ₚ;

p is 0, 1, or 2; and r is 0, 1, 2, 3, or 4.

10. A pharmaceutical composition comprising one or more compounds according to claim 1 and a pharmaceutically acceptable carrier or diluent.

11. A compound which is 6-cyclopropaneamido-4-[(3-methanesulfonylpyridin-2-yl)amino]-N—(²H₃)methylpyridazine-3-carboxamide;

6-[(5-fluoropyridin-2-yl)amino]-4-[(3-methanesulfonylpyridin-2-yl)amino]-N—(²H₃)methylpyridazine-3-carboxamide;

4-[(3-methanesulfonylpyridin-2-yl)amino]-6-[(6-methoxypyridazin-3-yl)amino]-N—(²H₃)methylpyridazine-3-carboxamide;

4-[(3-methanesulfonylpyridin-2-yl)amino]-N—(²H₃)methyl-6-[(1-methyl-1H-pyrazol-3-yl)amino]pyridazine-3-carboxamide;

6-[(6-cyclopropyl-2-methylpyrimidin-4-yl)amino]-4-[(3-methanesulfonylpyridin-2-yl)amino]-N—(²H₃)methylpyridazine-3-carboxamide;

6-{[5-(2-hydroxypropan-2-yl)pyridin-2-yl]amino}-4-[(3-methanesulfonylpyridin-2-yl)amino]-N—(²H₃)methylpyridazine-3-carboxamide;

6-[(6-cyclopropylpyrimidin-4-yl)amino]-4-[(3-methanesulfonylpyridin-2-yl)amino]-N—(²H₃)methylpyridazine-3-carboxamide;

6-[(6-cyclopropylpyridazin-3-yl)amino]-4-[(3-methanesulfonylpyridin-2-yl)amino]-N—(²H₃)methylpyridazine-3-carboxamide;

6-[(1,5-dimethyl-1H-pyrazol-3-yl)amino]-4-[(3-methanesulfonylpyridin-2-yl)amino]-N—(²H₃)methylpyridazine-3-carboxamide;

4-[(3-methanesulfonylpyridin-2-yl)amino]-N—(²H₃)methyl-6-{[5-(trifluoromethyl)pyridin-2-yl]amino}pyridine-3-carboxamide;

4-[(3-methanesulfonylpyridin-2-yl)amino]-N—(²H₃)methyl-6-{[6-(trifluoromethyl)pyridazin-3-yl]amino}pyridazine-3-carboxamide;

4-[(3-methanesulfonylpyridin-2-yl)amino]-6-[(2-methoxypyrimidin-4-yl)amino]-N—(²H₃)methylpyridazine-3-carboxamide;

6-{[5-fluoro-4-(2-hydroxypropan-2-yl)pyridin-2-yl]amino}-4-[(3-methanesulfonylpyridin-2-yl)amino]-N—(²H₃)methylpyridazine-3-carboxamide;

6-{[5-(2-aminopropan-2-yl)pyridin-2-yl]amino}-4-[(3-methanesulfonylpyridin-2-yl)amino]-N—(²H₃)methylpyridazine-3-carboxamide;

4-[(3-methanesulfonylpyridin-2-yl)amino]-N—(²H₃)methyl-6-{[1-(2,2,2-trifluoroethyl)-1H-pyrazol-3-yl]amino}pyridazine-3-carboxamide;

4-[(3-methanesulfonylpyridin-2-yl)amino]-6-{[6-(²H₃)methoxypyridazin-3-yl]amino}-N—(²H₃)methylpyridazine-3-carboxamide;

6-[(5-cyanopyridin-2-yl)amino]-4-[(3-methanesulfonylpyridin-2-yl)amino]-N—(²H₃)methylpyridine-3-carboxamide;

methyl N-{2-[6-({5-[(3-methanesulfonylpyridin-2-yl)amino]-6-[(²H₃)methylcarbamoyl]pyridazin-3-yl}amino)pyridin-3-yl]propan-2-yl}carbamate;

6-{[5-(1-cyanocyclopropyl)pyridin-2-yl]amino}-4-[(3-methanesulfonylpyridin-2-yl)amino]-N—(²H₃)methylpyridazine-3-carboxamide;

4-[(3-methanesulfonylpyridin-2-yl)amino]-N—(²H₃)methyl-6-{[5-(morpholin-4-yl)pyridin-2-yl]amino}pyridazine-3-carboxamide;

6-[(5-cyclopropylpyrazin-2-yl)amino]-4-[(3-methanesulfonylpyridin-2-yl)amino]-N—(²H₃)methylpyridazine-3-carboxamide;

4-[(3-methanesulfonylpyridin-2-yl)amino]-N—(²H₃)methyl-6-[(6-methylpyridazin-3-yl)amino]pyridazine-3-carboxamide;

4-[(3-methanesulfonylpyridin-2-yl)amino]-N—($^2$H$_3$)methyl-6-{[5-(trifluoromethyl)pyridin-2-yl]amino}pyridazine-3-carboxamide;

4-[(3-methanesulfonylpyridin-2-yl)amino]-N—($^2$H$_3$)methyl-6-[(5-methylpyrazin-2-yl)amino]pyridazine-3-carboxamide;

4-[(3-methanesulfonylpyridin-2-yl)amino]-6-{[4-(methoxymethyl)pyridin-2-yl]amino}-N—($^2$H$_3$)methylpyridazine-3-carboxamide;

6-[(2,6-dimethylpyrimidin-4-yl)amino]-4-[(3-methanesulfonylpyridin-2-yl)amino]-N—($^2$H$_3$)methylpyridazine-3-carboxamide;

6-{[6-(2,6-difluorophenyl)pyridazin-3-yl]amino}-4-[(3-methanesulfonylpyridin-2-yl)amino]-N—($^2$H$_3$)methylpyridazine-3-carboxamide;

6-cyclopropaneamido-4-[(3-methanesulfonylpyridin-2-yl)amino]-N—($^2$H$_3$)methylpyridine-3-carboxamide;

6-[(1S,2R)-2-fluorocyclopropaneamido]-4-[(3-methanesulfonylpyridin-2-yl)amino]-N—($^2$H$_3$)methylpyridazine-3-carboxamide;

6-[(1S,2S)-2-fluorocyclopropaneamido]-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-[(1R,2R)-2-methylcyclopropaneamido]pyridazine-3-carboxamide;

4-[(3-methanesulfonylpyridin-2-yl)amino]-N—($^2$H$_3$)methyl-6-{spiro[2.2]pentane-1-amido}pyridazine-3-carboxamide;

4-[(3-methanesulfonylpyridin-2-yl)amino]-N—($^2$H$_3$)methyl-6-[(1R,2R)-2-methylcyclopropaneamido]pyridazine-3-carboxamide;

6-[(6-cyclopropylpyrimidin-4-yl)amino]-4-[(3-methanesulfonylpyridin-2-yl)amino]-N—($^2$H$_3$)methylpyridine-3-carboxamide;

4-[(3-methanesulfonylpyridin-2-yl)amino]-N—($^2$H$_3$)methyl-6-[(2-methyl-2H-1,2,3-triazol-4-yl)amino]pyridazine-3-carboxamide;

6-[(6-cyclopropyl-2-methylpyrimidin-4-yl)amino]-4-[(3-methanesulfonylpyridin-2-yl)amino]-N—($^2$H$_3$)methylpyridine-3-carboxamide;

6-{[5-(2-hydroxypropan-2-yl)pyridin-2-yl]amino}-4-[(3-methanesulfonyl-6-methylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[5-(trifluoromethoxy)pyridin-2-yl]amino}pyridazine-3-carboxamide;

4-[(3-methanesulfonylpyridin-2-yl)amino]-N—($^2$H$_3$)methyl-6-[(1S)-spiro[2.2]pentane-1-amido]pyridazine-3-carboxamide;

4-[(3-methanesulfonylpyridin-2-yl)amino]-N—($^2$H$_3$)methyl-6-[(1R)-spiro[2.2]pentane-1-amido]pyridazine-3-carboxamide;

6-{[4-chloro-5-(2-hydroxypropan-2-yl)pyridin-2-yl]amino}-4-[(3-methanesulfonyl-6-methylpyridin-2-yl)amino]-N—($^2$H$_3$)methylpyridazine-3-carboxamide;

6-cyclopropaneamido-4-[(3-methanesulfonyl-6-methylpyridin-2-yl)amino]-N—($^2$H$_3$)methylpyridine-3-carboxamide;

6-{[4-chloro-5-(2-hydroxypropan-2-yl)pyridin-2-yl]amino}-4-[(3-methanesulfonyl-6-methoxypyridin-2-yl)amino]-N—($^2$H$_3$)methylpyridazine-3-carboxamide;

6-[(2-cyclopropyl-6-methylpyrimidin-4-yl)amino]-4-[(3-methanesulfonylpyridin-2-yl)amino]-N—($^2$H$_3$)methylpyridazine-3-carboxamide;

6-{[6-fluoro-5-(2-hydroxypropan-2-yl)pyridin-2-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-6-{[5-(methoxymethyl)pyridin-2-yl]amino}-N—($^2$H$_3$)methylpyridazine-3-carboxamide;

4-[(3-methanesulfonylpyridin-2-yl)amino]-6-({5-[($^2$H$_3$)methoxymethyl]pyridin-2-yl}amino)-N—($^2$H$_3$)methylpyridazine-3-carboxamide;

6-{[6-(difluoromethoxy)pyridazin-3-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[6-(propan-2-yl)pyridazin-3-yl]amino}pyridazine-3-carboxamide;

6-[(6-tert-butylpyridazin-3-yl)amino]-4-[(3-methanesulfonylpyridin-2-yl)amino]-N—($^2$H$_3$)methylpyridazine-3-carboxamide;

6-{[6-(difluoromethyl)pyridazin-3-yl]amino}-4-[(3-methanesulfonylpyridin-2-yl)amino]-N—($^2$H$_3$)methylpyridazine-3-carboxamide;

4-[(3-methanesulfonylpyridin-2-yl)amino]-N—($^2$H$_3$)methyl-6-[(1S,2S)-2-methylcyclopropaneamido]pyridazine-3-carboxamide; or 6-cyclopropaneamido-4-[(3-methanesulfonyl-6-methylpyridin-2-yl)amino]-N—($^2$H$_3$)methylpyridazine-3-carboxamide;

or a stereoisomer or pharmaceutically acceptable salt thereof.

12. The compound according to claim 11 which is 6-cyclopropaneamido-4-[(3-methanesulfonylpyridin-2-yl)amino]-N—($^2$H$_3$)methylpyridazine-3-carboxamide;

6-[(6-cyclopropyl-2-methylpyrimidin-4-yl)amino]-4-[(3-methanesulfonylpyridin-2-yl)amino]-N—($^2$H$_3$)methylpyridazine-3-carboxamide;

6-[(6-cyclopropylpyrimidin-4-yl)amino]-4-[(3-methanesulfonylpyridin-2-yl)amino]-N—($^2$H$_3$)methylpyridazine-3-carboxamide;

6-[(6-cyclopropylpyridazin-3-yl)amino]-4-[(3-methanesulfonylpyridin-2-yl)amino]-N—($^2$H$_3$)methylpyridazine-3-carboxamide;

6-cyclopropaneamido-4-[(3-methanesulfonylpyridin-2-yl)amino]-N—($^2$H$_3$)methylpyridine-3-carboxamide;

4-[(3-methanesulfonylpyridin-2-yl)amino]-N—($^2$H$_3$)methyl-6-[(1R,2R)-2-methylcyclopropaneamido]pyridazine-3-carboxamide;

4-[(3-methanesulfonylpyridin-2-yl)amino]-N—($^2$H$_3$)methyl-6-{spiro[2.2]pentane-1-amido}pyridazine-3-carboxamide;

4-[(3-methanesulfonylpyridin-2-yl)amino]-N—($^2$H$_3$)methyl-6-[(1S,2S)-2-methylcyclopropaneamido]pyridazine-3-carboxamide;

6-cyclopropaneamido-4-[(3-methanesulfonyl-6-methylpyridin-2-yl)amino]-N—($^2$H$_3$)methylpyridazine-3-carboxamide;

4-[(3-methanesulfonylpyridin-2-yl)amino]-N—($^2$H$_3$)methyl-6-{[5-(trifluoromethoxy)pyridin-2-yl]amino}pyridazine-3-carboxamide;

4-[(3-methanesulfonylpyridin-2-yl)amino]-N—($^2$H$_3$)methyl-6-[(1S)-spiro[2.2]pentane-1-amido]pyridazine-3-carboxamide;

4-[(3-methanesulfonylpyridin-2-yl)amino]-N—($^2$H$_3$)methyl-6-[(1R)-spiro[2.2]pentane-1-amido]pyridazine-3-carboxamide; or 6-{[4-chloro-5-(2-hydroxypropan-2-yl)pyridin-2-yl]amino}-4-[(3-methanesulfonyl-6-methylpyridin-2-yl)amino]-N—($^2$H$_3$)methylpyridazine-3-carboxamide or a stereoisomer or pharmaceutically acceptable salt thereof.
13. A compound having the structure
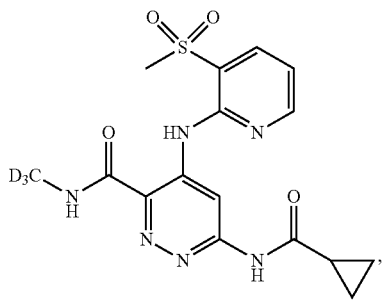 [SMILES: [2H]C([2H])([2H])NC(=O)c1nnc(NC(=O)C2CC2)cc1Nc1ncccc1S(C)(=O)=O]
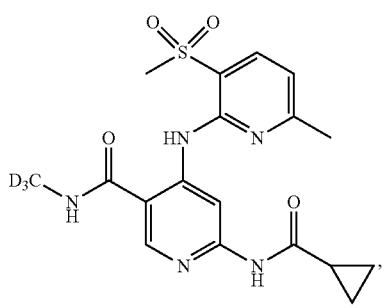
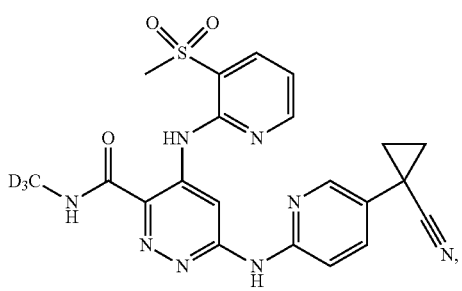
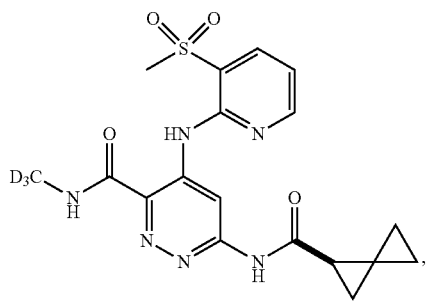
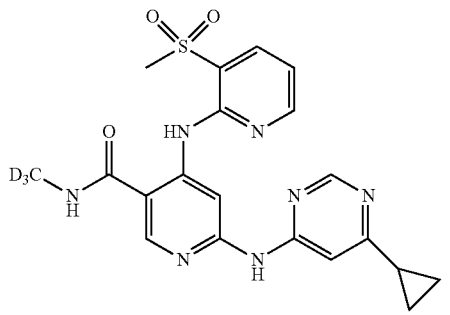
or
-continued
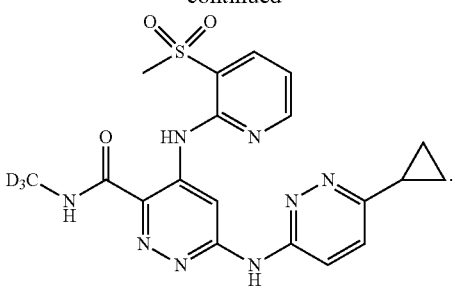
14. A pharmaceutical composition comprising the compound according to claim 13 and a pharmaceutically acceptable carrier or diluent.
15. A pharmaceutically acceptable salt of a compound having the structure
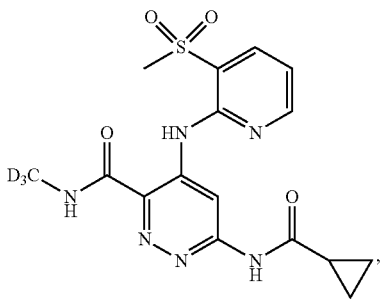
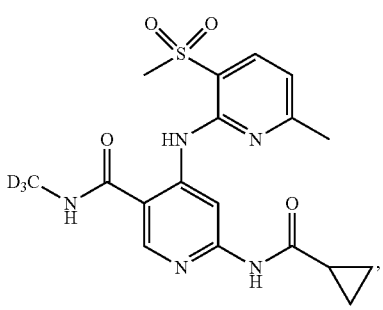
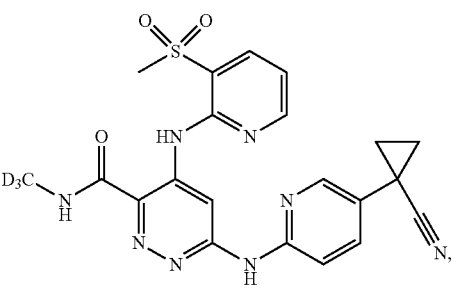

-continued

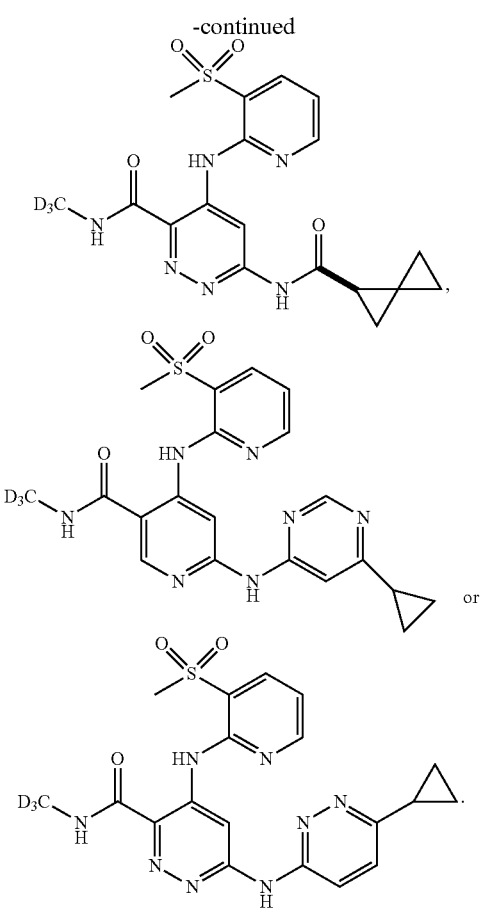

16. A pharmaceutical composition comprising the pharmaceutically acceptable salt according to claim 15 and a pharmaceutically acceptable carrier or diluent.

17. A compound having the structure

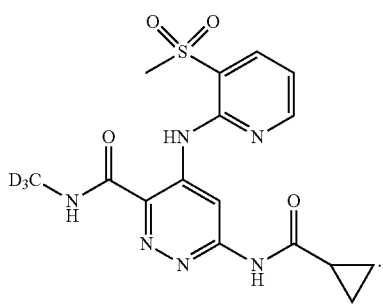 [SMILES: [2H]C([2H])([2H])NC(=O)c1nnc(NC(=O)C2CC2)cc1Nc1ncccc1S(C)(=O)=O]

18. A pharmaceutically acceptable salt of a compound having the structure

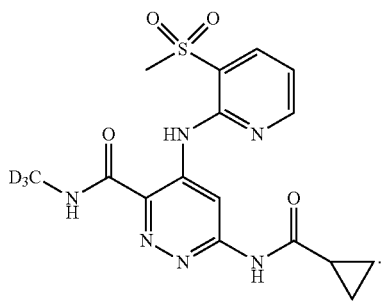

19. A compound having the structure

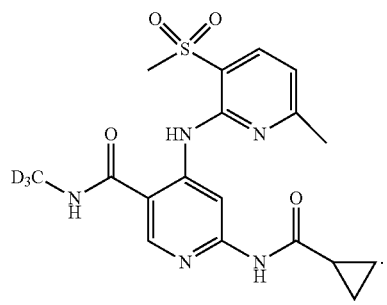 [SMILES: [2H]C([2H])([2H])NC(=O)c1cnc(NC(=O)C2CC2)cc1Nc1nc(C)ccc1S(C)(=O)=O]

20. A pharmaceutically acceptable salt of a compound having the structure

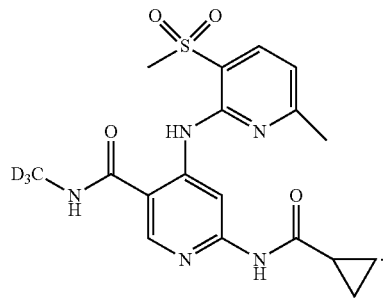 [SMILES: [2H]C([2H])([2H])NC(=O)c1cnc(NC(=O)C2CC2)cc1Nc1nc(C)ccc1S(C)(=O)=O]

21. A compound having the structure

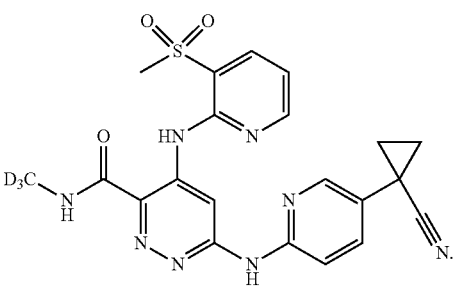 [SMILES: [2H]C([2H])([2H])NC(=O)c1nnc(Nc2ccc(C3(C#N)CC3)cn2)cc1Nc1ncccc1S(C)(=O)=O]

22. A pharmaceutically acceptable salt of a compound having the structure

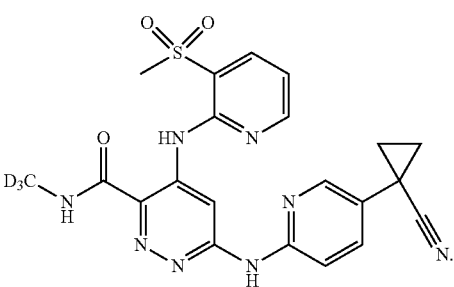 [SMILES: [2H]C([2H])([2H])NC(=O)c1nnc(Nc2ccc(C3(C#N)CC3)cn2)cc1Nc1ncccc1S(C)(=O)=O]

23. A compound having the structure
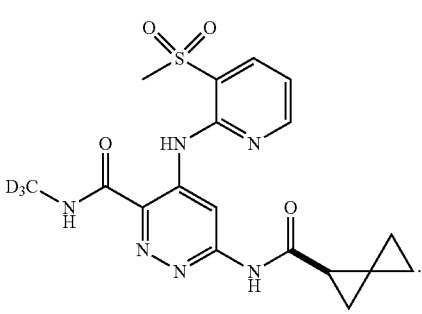 [SMILES: [2H]C([2H])([2H])NC(=O)c1nnc(NC(=O)[C@@H]2CC23CC3)cc1Nc1ncccc1S(C)(=O)=O]
24. A pharmaceutically acceptable salt of a compound having the structure
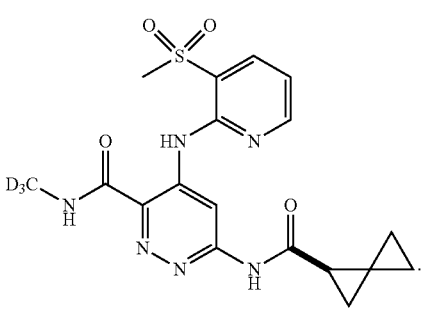 [SMILES: [2H]C([2H])([2H])NC(=O)c1nnc(NC(=O)[C@@H]2CC23CC3)cc1Nc1ncccc1S(C)(=O)=O]
25. A compound having the structure
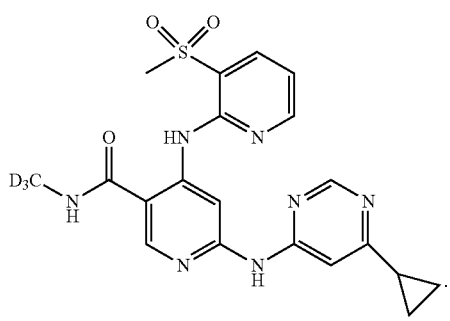 [SMILES: [2H]C([2H])([2H])NC(=O)c1cnc(Nc2cc(C3CC3)ncn2)cc1Nc1ncccc1S(C)(=O)=O]
26. A pharmaceutically acceptable salt of a compound having the structure
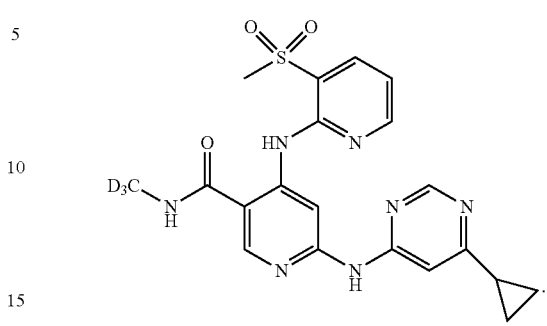
27. A compound having the structure
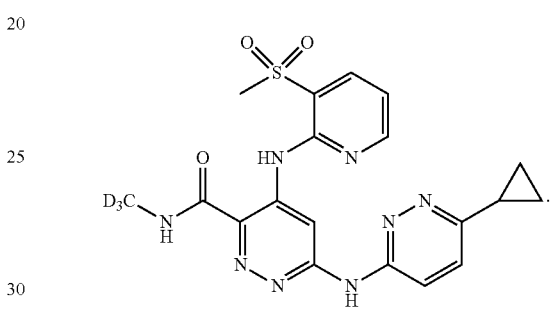
28. A pharmaceutically acceptable salt of a compound having the structure
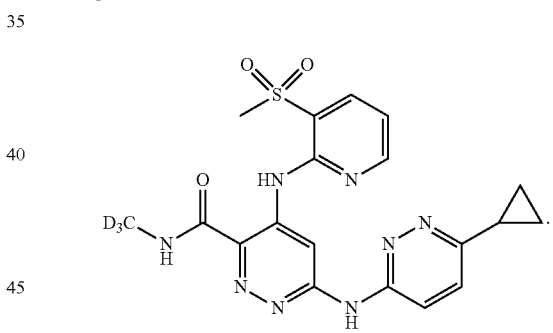
* * * * *

UNITED STATES PATENT AND TRADEMARK OFFICE
CERTIFICATE OF CORRECTION

PATENT NO. : 11,021,462 B2
APPLICATION NO. : 16/195951
DATED : June 1, 2021
INVENTOR(S) : Chunjian Liu et al.

It is certified that error appears in the above-identified patent and that said Letters Patent is hereby corrected as shown below:

In the Claims

In Claim 1, Column 138, Line 29 (2nd Occurrence), delete "—$(CH_2)_rNR^bC(O)R^c$," and insert -- —$(CH_2)_rNR^bC(O)OR^c$, --, therefor.

In Claim 1, Column 138, Line 30, delete "—$S(O)_pNR^{11}NR^{11}$," and insert -- —$S(O)_pNR^{11}R^{11}$, --, therefor.

In Claim 2, Column 139, Line 60, delete "—$S(O)_pNR^{11}NR^{11}$," and insert -- —$S(O)_pNR^{11}R^{11}$, --, therefor.

Signed and Sealed this
Eleventh Day of January, 2022

Drew Hirshfeld
*Performing the Functions and Duties of the
Under Secretary of Commerce for Intellectual Property and
Director of the United States Patent and Trademark Office*